(12) United States Patent
Yurke

(10) Patent No.: US 12,292,668 B2
(45) Date of Patent: May 6, 2025

(54) MOLECULAR AGGREGATE FOR OPTICALLY-PUMPED NONRECIPROCAL EXCITON DEVICES

(71) Applicant: Boise State University, Boise, ID (US)

(72) Inventor: Bernard Yurke, Boise, ID (US)

(73) Assignee: Boise State University, Boise, ID (US)

( * ) Notice: Subject to any disclaimer, the term of this patent is extended or adjusted under 35 U.S.C. 154(b) by 916 days.

(21) Appl. No.: 17/443,285

(22) Filed: Jul. 23, 2021

(65) Prior Publication Data

US 2023/0054578 A1   Feb. 23, 2023

(51) Int. Cl.
*G02F 1/35* (2006.01)
*C07H 21/04* (2006.01)
*G02B 1/04* (2006.01)
*G02F 1/361* (2006.01)

(52) U.S. Cl.
CPC .......... *G02F 1/3503* (2021.01); *C07H 21/04* (2013.01); *G02B 1/04* (2013.01); *G02F 1/3515* (2013.01); *G02F 1/3523* (2013.01); *G02F 1/3612* (2013.01); *G02F 1/3615* (2013.01)

(58) Field of Classification Search
CPC .... G02F 1/3503; G02F 1/3513; G02F 1/3523; G02F 1/3612; G02F 1/3615; G02B 1/04
See application file for complete search history.

(56) References Cited

U.S. PATENT DOCUMENTS 7,425,643 B1 * 9/2008 Jen ................. C07D 409/04
549/60
2010/0029953 A1 * 2/2010 Jen ................. G02F 1/3612
252/582

FOREIGN PATENT DOCUMENTS

CN      108440959 B  * 10/2019 ............ C08J 3/093
WO   WO-2021062491 A1 *  4/2021

* cited by examiner

*Primary Examiner* — Daniel Petkovsek
(74) *Attorney, Agent, or Firm* — McKee, Voorhees & Sease, PLC

(57) ABSTRACT

The present disclosure is directed to an optically active medium comprising dye aggregates and optionally a nucleotide oligomer or other nucleotide-based architecture, which may be used in in optical devices, in particular nonreciprocal devices (i.e., devices in which energy flows in one direction only), that can respond to differences in the polarization of light. An analysis is presented of the energy levels and the strengths of the optical transitions (changes in energy states) for a three-chromophore (dye) aggregate in which the chromophores are coupled with a J-like (i.e., end-to-end) stacking. Specific devices and methods of use are also disclosed herein.

37 Claims, 11 Drawing Sheets

MOLECULAR AGGREGATE FOR OPTICALLY-PUMPED NONRECIPROCAL EXCITON DEVICES

GRANT REFERENCE

This invention was made with government support under Grant No. N00014-19-1-2615, awarded by the Department of the Navy, Office of Naval Research. The Government has certain rights in the invention.

FIELD OF THE INVENTION

The invention relates generally to optical systems. More specifically, the invention relates to chromophores, which may be templated on nucleotides or covalently bound end-to-end to form J-like stacked aggregates, that act as optically active elements in response to the differences in the polarization of light in optical systems.

BACKGROUND OF THE INVENTION

Optical systems are becoming increasingly popular due to their high speed and high data capacity capabilities. Light has bidirectional transmission reciprocity in common dielectric materials. Breaking this reciprocity in the direction of light transmission is of great significance in classical and quantum information processing. Optical isolators, circulators, switches, and directional amplifiers are examples of non-reciprocal devices. Optical isolators are optical components which allow the transmission of light in only one direction and are typically used to prevent unwanted feedback into an optical oscillator. Optical circulators are three- or four-port optical devices designed such that light entering any of the ports exits from the next. Optical switches are devices which selectively direct optical signals from one channel to another. Optical directional amplifiers are devices which amplify an optical signal without first converting it into an electoral signal.

Most current optical isolators and circulators rely on a Faraday rotator to apply a longitudinal static magnetic field along the light source to create a Faraday effect to rotate the optical signal, or light, to change the state of the polarization. Other rotators include birefringent rotators using wave plates and prism rotators. As this change in state of the polarization is rotational, this results in a circular polarization of the light while typically not altering the frequency or amplitude of the signal. The rotation created by the Faraday rotator is a non-reciprocal optical propagation of the signal. Reflecting an already polarized beam back through the same Faraday rotator does not undo the polarization change but will typically double it. This doubly rotated signal may then be blocked by a polarizer or split using a birefringent wedge, allowing for undesired reflections or signals from disrupting upstream optical systems. Both optical isolators and circulators may use a Faraday rotator to take advantage of this property to prevent the undesired reflections.

However, current optical isolators and circulators are bulky and not specifically suitable to be used as integrated optical components as optical systems are getting smaller. They are also too bulky to integrate on chips. Therefore, smaller components are needed to be used in increasingly smaller systems.

BRIEF SUMMARY OF THE INVENTION

Applicants have created compositions of non-reciprocal optical devices comprising of aggregates of chromophores either attached to a nucleotide architecture or covalently bonded having a desired conformation. When two or more chromophores are spaced sufficiently close (nanospaced), near-field interactions, such as, but not limited to, electromagnetic dipole-dipole interactions form resulting in an increase in the coupling strength between two or more chromophores and a change in absorption of light relating to its polarization. The coupling strength between the two or more chromophore dipoles increases such that they are either weakly or strongly coupled opposed to being very weakly coupled or uncoupled. When the proximity of the chromophores is such that their orbitals overlap, in some cases this may result in an additional increase in coupling strength.

In an aspect, an optically active medium is made up of at least one chromophore or a population of aggregates of chromophores. In an embodiment, the optically active medium of a non-reciprocal optical device comprises chromophore aggregates coupled end-to-end in J-like stacking. In an embodiment, the chromophores are covalently linked end-to-end. In another embodiment, the chromophores are bonded to DNA which holds the chromophores in J-like stacking. In some embodiments, the aggregates are dimers of chromophores. In other embodiments, the aggregates are trimers of chromophores.

In another aspect, the optically active medium may be used as a component of an optical device because of its ability to absorb specific polarized light. In a preferred embodiment, the optical device is a non-reciprocal optical device. In a more preferred embodiment, the optical device is an optical isolator, circulator, switch, and/or directional amplifier. In a further embodiment, the optical device is a pumped nonreciprocal device.

In an aspect, the optically active medium exhibits a switchable circular dichroism which may be affected by the circular polarization of a pump light. In an embodiment, the optically active medium is pumped. In a preferred embodiment, the pump light is circularly polarized and induces circular dichroic activity in the optically active medium. In a preferred embodiment, at least a population of the planes of the aggregates are perpendicularly oriented to the direction of the propagation of the light beam. In a further embodiment, pump light is introduced to a signal light and mixed using dichroic mirrors prior to propagation through the optically active medium so that the optically active medium absorbs a single polarization of the mixed light.

While multiple embodiments are disclosed, still other embodiments of the present invention will become apparent to those skilled in the art from the following detailed descriptions, which show and describe illustrative embodiments of the invention. Accordingly, the figures and detailed description are to be regarded as illustrative in nature and not restrictive.

BRIEF DESCRIPTION OF THE DRAWINGS

FIG. 7 is a graphical representation of absorbance and fluorescence spectra corresponding to the immobile 4-arm junction (4AJ) templated Cy5 chromophores.

DETAILED DESCRIPTION

Figure 1:
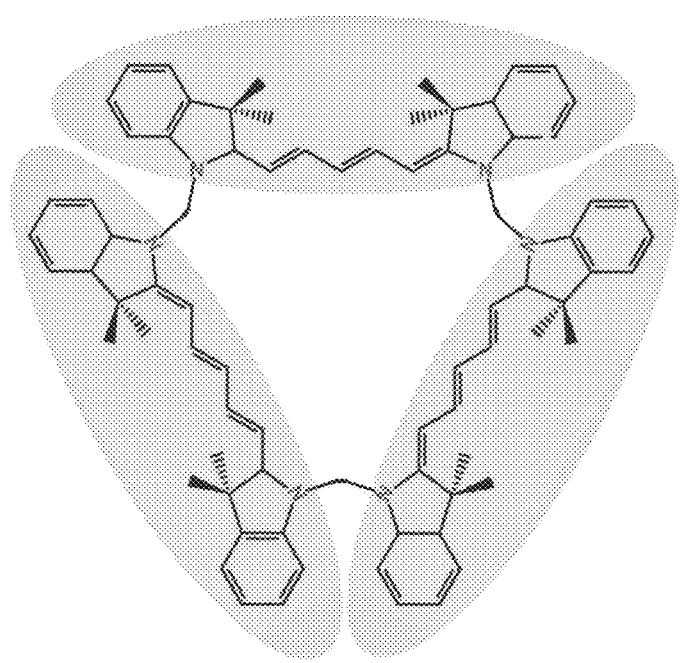
FIG. 1 shows an example of a chromophore aggregate trimer with three dyes covalently linked in a triangular arrangement. The ends of the dyes are in close proximity giving rise to J-like coupling. The dye depicted is the cyanine dye Cy5. The chromophore units are highlighted with the ellipses. Similar chromophore arrangements can be produced by DNA-based assembly, in which case the dyes are not necessarily covalently linked to each other; instead, they are covalently linked to the DNA or bound to the DNA by supramolecular means.

In the following detailed description, reference may made to the accompanying drawings, schemes, and structures which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). The embodiments of this disclosure are not limited to any specific compositions and methods which can vary and are understood by skilled artisans. It is further to be understood that all terminology used herein is for describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (i.e., 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

Definitions

The following terms, unless otherwise indicated, shall be understood to have the following meanings:

It should be noted that, as used in this specification and the appended claims, the singular forms "a," "an," "said," "another," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

Other than in the operating examples, or where otherwise indicated, all numbers expressing quantities of ingredients or reaction conditions used herein are to be understood as being modified in all instances by the term "about."

As used herein, the term "about" modifying the quantity or quality of an ingredient in the compositions of the invention or employed in the methods of the invention refers to variation in the numerical quantity that can occur, for example, through typical measuring errors; through inadvertent error in these procedures; through differences in the manufacture, source, or purity of the ingredients employed to make the compositions or carry out the methods; and the like. Whether or not modified by the term "about," the claims include equivalents to the quantities.

"Non-covalent" refers to any molecular interactions that are not covalent—i.e., the interaction does not involve the sharing of electrons. The term includes, for example, electrostatic, π-effects, van der Waals forces, and hydrophobic effects. "Covalent" refers to interactions involving the sharing of one or more electrons.

As used herein, a "brick" is a structural unit. A brick may be of any shape or size. The main body of a brick may be of any material composition. An example of a brick is a "nucleotide brick," which is a structural unit where the body of the brick is made of a nucleotide oligomer. An example of a nucleotide brick is a "DNA brick," which is a nucleotide brick where the body of the brick is made of a DNA oligomer.

As used herein, a "nucleotide" is any nucleoside linked to a phosphate group. The nucleoside may be natural, including but not limited to, any of cytidine, uridine, adenosine, guanosine, thymidine, inosine (hypoxanthine), or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, which acts as a linker group lacking a base or may be a nucleotide analog.

As used herein, "nucleotide duplex" is when two strands of complement nucleotide oligomers complementary bind to each other. The two strands may be part of the same nucleotide molecule or separate nucleotide molecules.

As used herein, "nucleotide origami" is two or more nucleotide bricks, where one brick is a "scaffold" and provides the main body of the overall structure and is bound by one or more "staple(s)."

As used herein, a "scaffold" is a single stranded nucleotide brick rationally-designed to self-assemble into hairpin loops, helical domains, and locking domains. The scaffold may use staples to direct the folding and to hold the final shape. Alternatively, the scaffold may use intrinsic self-complementary pairing to hold the final shape.

As used herein, a "staple" or "staple strand" is a nucleotide brick which pairs with a longer main body brick in nucleotide origami to help fold the main body brick into the desired shape.

As used herein, a "nanobreadboard," "breadboard," or "template" is a total or final structure of a DNA structure or shape. For example, a mobile or immobile 4-arm junction, DNA origami happy face, rectangular brick, or double stranded DNA (dsDNA) in its final structure.

As used herein, an "architecture" is a one-, two-, or three-dimensional structure built using one or more bricks. As used herein, a "nucleotide architecture" is a one-, two-, or three-dimensional structure built using one or more nucleotide bricks. Examples include nucleotide origami or molecular canvases.

As used herein, "self-assembly" refers to the ability of nucleotides to adhere to each other, in a sequence-specific manner, in a predicted manner and without external control.

As used herein, "sufficiently close" and "nanospaced" refers to a distance between two chromophores that allows one chromophore, when excited, to create an exciton whose excitation energy is shared with a second chromophore without a loss of energy (i.e., coherent energy transfer).

As used herein, a "breadboard" refers to a reusable solderless device used to build an excitonic circuit. The breadboard allows for temporary placement of different solutions, such as solutions containing chromophore-bound nucleotide architectures, in different arrangements.

As used herein, Förster resonance energy transfer (FRET), fluorescence resonance energy transfer (FRET), resonance energy transfer (RET), or electronic energy transfer (EET) refers to energy transfer between two light-sensitive molecules (donor and acceptor chromophores) or aggregates thereof in an incoherent process in which energy loss occurs.

As used herein, the terms "dye aggregate," "chromophore aggregate," or "aggregate" are used interchangeably unless otherwise specified. Aggregates are also referred to as mers of dyes. A dye aggregate comprised of two dyes is called a dimer, composed of three dyes is called a trimer, composed of four dyes is called a tetramer, and so on.

As used herein, the term "dye" refers to a molecule comprising a "chromophore" or a "fluorophore." As the chromophore or fluorophore may comprise the entire molecule, "dye", "chromophore", and "fluorophore" may be used interchangeably with each other unless otherwise specified.

As used herein, "substituted" refers to an organic group as defined below (i.e., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, 6, or more substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (i.e., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (i.e., cyclopropyl, cyclopentyl, cyclohexyl, cycloheptyl, cyclooctyl, etc.), branched-chain alkyl groups (i.e., isopropyl, tert-butyl, sec-butyl, isobutyl, etc.), and alkyl-substituted alkyl groups (i.e., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about 30 carbon atoms, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about 30 carbon atoms, and further including at least one triple bond. In some embodiments, an alkynyl group has from 2 to about 30 carbon atoms, or typically, from 2 to 10 carbon atoms. Alkynyl groups may be substituted or unsubstituted. Alkynyl groups may be substituted similarly to alkyl or alkenyl groups.

As used herein, the terms "alkylene", "cycloalkylene", "alkynylides", and "alkenylene", alone or as part of another substituent, refer to a divalent radical derived from an alkyl, cycloalkyl, or alkenyl group, respectively, as exemplified by —CH2CH2CH2-. For alkylene, cycloalkylene, alkynylene, and alkenylene groups, no orientation of the linking group is implied.

The term "ester" as used herein refers to —R30COOR31 group. R30 is absent, a substituted or unsubstituted alkylene, cycloalkylene, alkenylene, alkynylene, arylene, aralkylene, heterocyclylalkylene, or heterocyclylene group as defined herein. R31 is a substituted or unsubstituted alkyl, cycloalkyl, alkenyl, alkynyl, aryl, aralkyl, heterocyclylalkyl, or heterocyclyl group as defined herein.

The term "amine" (or "amino") as used herein refers to —R32NR33R34 groups. R32 is absent, a substituted or unsubstituted alkylene, cycloalkylene, alkenylene, alkynylene, arylene, aralkylene, heterocyclylalkylene, or heterocylylene group as defined herein. R33 and R34 are independently hydrogen, or a substituted or unsubstituted alkyl, cycloalkyl, alkenyl, alkynyl, aryl, aralkyl, heterocyclylalkyl, or heterocyclyl group as defined herein.

The term "amine" as used herein also refers to an independent compound. When an amine is a compound, it can be represented by a formula of R32'NR33'R34' groups, wherein R32', R33', and R34 are independently hydrogen, or a substituted or unsubstituted alkyl, cycloalkyl, alkenyl, alkynyl, aryl, aralkyl, heterocyclylalkyl, or heterocyclyl group as defined herein.

The term "alcohol" as used herein refers to —R35OH groups. R35 is absent, a substituted or unsubstituted alkylene, cycloalkylene, alkenylene, alkynylene, arylene, aralkylene, heterocyclylalkylene, or heterocyclylene group as defined herein.

The term "carboxylic acid" as used herein refers to —R36COOH groups. R36 is absent, a substituted or unsubstituted alkylene, cycloalkylene, alkenylene, alkynylene, arylene, aralkylene, heterocyclylalkylene, or heterocyclylene group as defined herein.

The term "ether" as used herein refers to —R37OR38 groups. R37 is absent, a substituted or unsubstituted alkylene, cycloalkylene, alkenylene, alkynylene, arylene, aralkylene, heterocyclylalkylene, or heterocyclylene group as defined herein. R38 is a substituted or unsubstituted alkyl, cycloalkyl, alkenyl, alkynyl, aryl, aralkyl, heterocyclylalkyl, or heterocyclyl group as defined herein.

Oligonucleotides

The dyes disclosed herein may be tethered to one, two, or more oligonucleotides. As used herein, an oligonucleotide can contain all the natural nucleotides found in nature or one, more, or all modified or synthetic nucleotides, in addition to the natural nucleotides and the nucleotides containing the donor, acceptor, or photochromic moiety. A modified or synthetic nucleotide in the oligonucleotides can differ from a natural occurring nucleotide in its base, sugar, and/or backbone moiety.

The oligonucleotide disclosed herein can be, but are not limited to, a peptide nucleic acid (PNA), a locked nucleic acid (LNA), an unlocked nucleic acid (UNA), a bridged nucleic acid polymer, or combination thereof.

PNA is an artificially synthesized polymer like DNA or RNA. While DNA and RNA have a deoxyribose and ribose sugar backbone, respectively, PNA's backbone is composed of repeating N-(2-aminoethyl)-glycine units linked by peptide bonds. The various purine and pyrimidine bases are linked to the backbone by a methylene bridge (—CH2-) and a carbonyl group (—(C=O)—).

PNA oligomers can show greater specificity in binding to complementary DNAs, with a PNA/DNA base mismatch being more destabilizing than a similar mismatch in a DNA/DNA duplex.

A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired and hybridize with DNA or RNA according to Watson-Crick base-pairing rules. LNA polymer are synthesized chemically and are commercially available. The locked ribose conformation enhances base stacking and backbone pre-organization. This significantly increases the hybridization properties (melting temperature) of oligonucleotides.

Bridged nucleic acids (BNAs) are modified RNA nucleotides. They are sometimes also referred to as constrained or inaccessible RNA molecules. BNA monomers can contain a five-membered, six-membered, or even a seven-membered bridged structure with a "fixed" C3'-endo sugar puckering. The bridge is synthetically incorporated at the 2', 4'-position of the ribose to afford a 2', 4'-BNA monomer. The monomers can be incorporated into oligonucleotide polymeric structures using standard phosphoramidite chemistry. BNAs are structurally rigid oligo-nucleotides with increased binding affinities and stability.

The nucleobase making up the oligomer may be natural, including but not limited to, any of cytosine, uracil, adenine, guanine, thymine, hypoxanthine, or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, or alternatively a nucleotide analog may be used.

Non-limiting examples of synthetic nucleobases and analogs include, but are not limited to methyl-substituted phenyl analogs, such as but not limited to mono-, di-, tri-, or tatramethylated benzene analogs; hydrophobic base analogs, such as but not limited to 7-propynyl isocarbostyril nucleoside, isocarbostyril nucleoside, 3-methylnapthalene, azaindole, bromo phenyl derivates at positions 2, 3, and 4, cyano derivatives at positions 2, 3, and 4, and fluoro derivates at position 2 and 3; purine/pyrimidine mimics, such as but not limited to azole hetercyclic carboxamides, such as but not limited to (1H)-1,2,3-triazole-4-carboxamide, 1,2,4-triazole-3-carboxamide, 1,2,3-triazole-4-carboxamide, or 1,2-pyrazole-3-carboxamide, or heteroatom-containing purine mimics, such as furo or theino pyridiones, such as but not limited to furo[2,3-c]pyridin-7(6H)-one, thieno[2,3-c]pyridin-7(6H)-one, furo[2,3-c]pyridin-7-thiol, furo[3,2-c]pyridin-4(5H)-one, thieno[3,2-c]pyridin-4(5H)-one, or furo[3,2-c]pyridin-4-thiol, or other mimics, such as but not limited to 5-phenyl-indolyl, 5-nitro-indolyl, 5-fluoro, 5-amino, 4-methylbenzimidazole, 6H,8H-3,4-dihydropropyrimido[4,5-c][1,2]oxazin-7-one, or $N^6$-methoxy-2,6-diaminopurine; isocytosine, isoquanosine; thymidine analogs, such as but not limited to 5-methylisocytosine, difluorotoluene, 3-toluene-1-β-D-deoxyriboside, 2,4-difluoro-5-toluene-1-β-D-deoxyriboside, 2,4-dichloro-5-toluene-1-β-D-deoxyriboside, 2,4-dibromo-5-toluene-1-β-D-deoxyriboside, 2,4-diiodo-5-toluene-1-β-D-deoxyriboside, 2-thiothymidine, 4-Se-thymidine; or fluorescent base analogs, such as but not limited to 2-aminopurine, 1,3-diaza-2-oxophenothiazine, 1,3-diaza-2-oxophenoxazine, pyrrolo-dC and derivatives, 3-MI, 6-MI, 6-MAP, or furan-modified bases.

Non-limiting examples of nucleotide analogs include, but are not limited to, phosporothioate nucleotides, 2'-O-methyl ribonucleotides, 2'-O-methoxy-ethyl ribonucleotides, peptide nucleotides (PNA), N3'-P5' phosphoramidate, 2'-fluoro-arabino nucleotides, locked nucleotides (LNA), unlocked nucleotides (UNA), bridge nucleotides (BNA), morpholino phosphoramidate, cyclohexene nucleotides, tricyclo-deoxynucleotides, or triazole-linked nucleotides.

A modified nucleotide can be, but is not limited to, d5SICS and dNaM that base pair with each other and dTPT3 also base pairs with dNaM (Floyd Romesberg), 2-amino-8-(2-thienyl)purine that base-pairs with pyridine-2-one (y), 7-(2-thienyl)imidazo[4,5-b]pyridine (Ds) that base-pairs with pyrrole-2-carbaldehyde (Pa), and Ds that base pairs with 4-[3-(6-aminohexanamido)-1-propynyl]-2-nitropyrrole (Px).

The oligonucleotide can be a single strand, which one or more dyes and can fold into such a conformation, so that the dyes are close enough to each other to allow energy transfer, such as a photochromic Förster resonance energy transfer (pcFRET), or exciton sharing or transfer can happen between the dyes. Preferably, exciton sharing or transfer happens between the dyes As used herein, Förster resonance energy transfer (FRET), fluorescence resonance energy transfer (FRET), resonance energy transfer (RET), or electronic energy transfer (EET) refers to energy transfer between two light-sensitive molecules, such as between two or more dyes, such as a fluorophore or a chromophore. A first dye, initially in its electronic excited state, may transfer energy to a second dye through nonradiative dipole-dipole coupling. The dipole-dipole coupling occurring in FRET is classified as a very weak coupling. The efficiency of this energy transfer is inversely proportional to the sixth power of the distance between the first and second chromophore, resulting in a loss of energy during the transfer.

In FRET, the excited chromophore, or doner chromophore, emits a virtual or undetectable photon that is instantly absorbed by a second chromophore, the acceptor chromophore. FRET does not change the absorbance spectrum or emittance spectrum of the individual chromophores involved in the energy transfer.

While FRET is the transfer of energy between two chromophores, a system of chromophores, comprising more than two chromophores, may each use FRET to transfer energy from one chromophore to the next along the system as long as the absorbance spectrum of the acceptor chromophore is within the emittance spectrum of the doner chromophore. Therefore, each chromophore may act as a doner chromophore and acceptor chromophore in the system.

Exciton transfer or sharing, or molecular excitation model, differs from FRET in several ways. While FRET is a very weak dipole-dipole coupling that transfers energy through a virtual photon, exciton transfer or sharing requires a strong or weak coupling of the dipoles of two or more chromophores and shares excitons within the aggregate. When two or more chromophore dipoles are weakly or strongly coupled, excitons may delocalize over the two or more chromophores. Also, the efficiency of coherent energy transfer is better than FRET and falls of as third power of the distance between the dyes. Therefore, the energy captured by the exciton is shared within the aggregate and so energy is not lost when the energy is transferred from chromophore to chromophore through the aggregate.

Also, unlike FRET, a weakly or strongly coupled aggregate of two or more chromophores may act as a single chromophore. This may be measured by detecting a change in the absorbance or emission spectrum of the system.

The DNA or RNA structure may be a duplex including two or more mostly matching or complementary oligonucleotides. In this situation, one of the two or more oligonucleotides can contain one of or all the dyes, and the other can contain the rest.

In some embodiments, two or more oligonucleotides form one duplex. In some embodiments, two or more oligonucleotides form two or more duplexes.

Nucleotide Architecture

The chromophores may optionally be attached to more complicated nucleotide architectures. Nucleotide nanotechnology can be used to form complicated one-, two-, and three-dimensional architectures. The nucleotide architectures may comprise of one or more nucleotide bricks. The nucleotide bricks are designed to use the Watson-Crick pairing of the nucleotides to cause the bricks to self-assemble into the final and predictable architectures. Any method of designing the architectures and self-assembly may be used, such as but not limited to nucleotide origami, nucleotide brick molecular canvases, single stranded tile techniques, or any other method of nucleotide folding or nanoassembly such as, but not limited to, using nucleotide tiles, nucleotide scaffolds, nucleotide lattices, four-armed junction, double-crossover structures, nanotubes, static nucleotide structures, dynamically changeable nucleotide structures, or any other synthetic biology technique (as described in U.S. Pat. No. 9,073,962, U.S. Pub. No.: US 2017/0190573, U.S. Pub. No.: US 2015/0218204, U.S. Pub. No.: US 2018/0044372, or International Publication Number WO 2014/018675, each of which is incorporated in its entirety by reference).

The nucleobase making up the bricks may be natural, including but not limited to, any of cytosine, uracil, adenine, guanine, thymine, hypoxanthine, or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, or alternatively a nucleotide analog may be used.

Non-limiting examples of synthetic nucleobases and analogs include, but are not limited to methyl-substituted phenyl analogs, such as but not limited to mono-, di-, tri-, or tatramethylated benzene analogs; hydrophobic base analogs, such as but not limited to 7-propynyl isocarbostyril nucleoside, isocarbostyril nucleoside, 3-methylnapthalene, azaindole, bromo phenyl derivates at positions 2, 3, and 4, cyano derivatives at positions 2, 3, and 4, and fluoro derivates at position 2 and 3; purine/pyrimidine mimics, such as but not limited to azole hetercyclic carboxamides, such as but not limited to (1H)-1,2,3-triazole-4-carboxamide, 1,2,4-triazole-3-carboxamide, 1,2,3-triazole-4-carboxamide, or 1,2-pyrazole-3-carboxamide, or heteroatom-containing purine mimics, such as furo or theino pyridiones, such as but not limited to furo[2,3-c]pyridin-7(6H)-one, thieno[2,3-c]pyridin-7(6H)-one, furo[2,3-c]pyridin-7-thiol, furo[3,2-c]pyridin-4(5H)-one, thieno[3,2-c]pyridin-4(5H)-one, or furo[3,2-c]pyridin-4-thiol, or other mimics, such as but not limited to 5-phenyl-indolyl, 5-nitro-indolyl, 5-fluoro, 5-amino, 4-methylbenzimidazole, 6H,8H-3,4-dihydropropyrimido[4,5-c][1,2]oxazin-7-one, or $N^6$-methoxy-2,6-diaminopurine; isocytosine, isoquanosine; thymidine analogs, such as but not limited to 5-methylisocytosine, difluorotoluene, 3-toluene-1-β-D-deoxyriboside, 2,4-difluoro-5-toluene-1-β-D-deoxyriboside, 2,4-dichloro-5-toluene-1-β-D-deoxyriboside, 2,4-dibromo-5-toluene-1-β-D-deoxyriboside, 2,4-diiodo-5-toluene-1-β-D-deoxyriboside, 2-thiothymidine, 4-Se-thymidine; or fluorescent base analogs, such as but not limited to 2-aminopurine, 1,3-diaza-2-oxophenothiazine, 1,3-diaza-2-oxophenoxazine, pyrrolo-dC and derivatives, 3-MI, 6-MI, 6-MAP, or furan-modified bases.

Non-limiting examples of nucleotide analogs include, but are not limited to, phosporothioate nucleotides, 2'-O-methyl ribonucleotides, 2'-O-methoxy-ethyl ribonucleotides, peptide nucleotides (PNA), N3'-P5' phosphoramidate, 2'-fluoro-arabino nucleotides, locked nucleotides (LNA), unlocked nucleotides (UNA), bridge nucleotides (BNA), morpholino phosphoramidate, cyclohexene nucleotides, tricyclo-deoxy-nucleotides, or triazole-linked nucleotides.

A modified nucleotide can be, but is not limited to, d5SICS and dNaM that base pair with each other and dTPT3 also base pairs with dNaM (Floyd Romesberg), 2-amino-8-(2-thienyl)purine that base-pairs with pyridine-2-one (y), 7-(2-thienyl)imidazo[4,5-b]pyridine (Ds) that base-pairs with pyrrole-2-carbaldehyde (Pa), and Ds that base pairs with 4-[3-(6-aminohexanamido)-1-propynyl]-2-nitropyrrole (Px).

The nucleotides can then be polymerized into oligomers. The design of the oligomers will depend on the design of the final architecture. Simple architectures may be designed by any methods. However, more complex architectures may be design using software such as, but not limited to, caDNAno (as described at http://cadnano.org/docs.html, and herein incorporated by reference), to minimize errors and time. The user may input the desired shape of the architecture into the software and once finalized, the software will provide the oligomer sequences of the bricks to create the desired architecture.

In some embodiments the architecture is comprised of nucleotide brick molecular canvases, wherein the canvases are made of 1 to 5,000 nucleotide bricks comprising of nucleotide oligomers of 24 to 48 nucleotides and will self-assemble in a single reaction, a "single-pot" synthesis, as described in U.S. Pub. No.: US 2015/0218204. In more preferable embodiments, the canvases are made of 1 to 1,000 nucleotide bricks, from 1 to 750 nucleotide bricks, from 1 to 500 nucleotide bricks, or from 1 to 250 nucleotide bricks. In other embodiments, the oligomers comprise of 24 to 42 nucleotides, from 24 to 36 nucleotides, or from 26 to 36 nucleotides.

In another embodiment the architecture is made step wise using a serial fluidic flow to build the final shape as described in U.S. Pat. No. 9,073,962.

In some embodiments, the architecture is assembled using the origami approach. With a DNA origami approach, for example, a long scaffold nucleic acid strand is folded to a predesigned shape through interactions with relatively shorter staple strands. Thus, in some embodiments, a single-stranded nucleic acid for assembly of a nucleic acid nanostructure has a length of at least 500 base pairs, at least 1 kilobase, at least 2 kilobases, at least 3 kilobases, at least 4 kilobases, at least 5 kilobases, at least 6 kilobases, at least 7 kilobases, at least 8 kilobases, at least 9 kilobases, or at least 10 kilobases. In some embodiments, a single-stranded nucleic acid for assembly of a nucleic acid nanostructure has a length of 500 base pairs to 10 kilobases, or more. In some embodiments, a single-stranded nucleic acid for assembly of a nucleic acid nanostructure has a length of 7 to 8 kilobases. In some embodiments, a single-stranded nucleic acid for assembly of a nucleic acid nanostructure comprises the M13 viral genome. In some embodiments, the number of staple strands is less than about 500 staple strands, less than about 400 staple strands, less than about 300 staple strands, less than about 200 staple strands, or less than about 100 staple strands.

In some embodiments, the architecture is assembled from single-stranded tiles (SSTs) (see, e.g., Wei B. et al. Nature 485: 626, 2012, incorporated by reference herein) or nucleic acid "bricks" (see, e.g., Ke Y. et al. Science 388:1177, 2012; International Publication Number WO 2014/018675 A1 each of which is incorporated by reference herein). For example, single-stranded 2- or 4-domain oligonucleotides self-assemble, through sequence-specific annealing, into two- and/or three-dimensional nanostructures in a predetermined (e.g., predicted) manner. As a result, the position of each oligonucleotide in the nanostructure is known. In this way, a nucleic acid nanostructure may be modified, for example, by adding, removing or replacing oligonucleotides at particular positions. The nanostructure may also be modified, for example, by attachment of moieties, at particular positions. This may be accomplished by using a modified oligonucleotide as a starting material or by modifying a particular oligonucleotide after the nanostructure is formed. Therefore, knowing the position of each of the starting oligonucleotides in the resultant nanostructure provides addressability to the nanostructure.

In some embodiments, the architecture is made from a single stranded oligomer, as described in U.S. Pub. No.: 2018/0044372 and herein incorporated by reference. A single strand of DNA used for assembling a nanostructure in accordance with the present disclosure may vary in length. In some embodiments, a single strand of DNA has a length of 500 nucleotides to 10,000 nucleotides, or more. For example, a single strand of DNA may have a length of 500 to 9000 nucleotides, 500 to 8000 nucleotides, 500 to 7000 nucleotides, 500 to 6000 nucleotides, 500 to 5000 nucleotides, 500 to 4000 nucleotides, 500 to 3000 nucleotides, 500 to 2000 nucleotides, 500 to 1000 nucleotides, 1000 to 10000 nucleotides, 1000 to 9000 nucleotides, 1000 to 8000 nucleotides, 1000 to 7000 nucleotides, 1000 to 6000 nucleotides, 1000 to 5000 nucleotides, 1000 to 4000 nucleotides, 1000 to 3000 nucleotides, 1000 to 2000 nucleotides, 2000 to 10000 nucleotides, 2000 to 9000 nucleotides, 2000 to 8000 nucleotides, 2000 to 7000 nucleotides, 2000 to 6000 nucleotides, 2000 to 5000 nucleotides, 2000 to 4000 nucleotides, or 2000 to 3000 nucleotides. In some embodiments, a single strand of DNA may have a length of at least 2000 nucleotides, at least 3000 nucleotides, at least 4000 nucleotides, or at least 5000 nucleotides. In some embodiments, a single strand of DNA may have a length of 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3100, 3200, 3300, 3400, 3500, 3600, 3700, 3800, 3900, 4100, 4200, 4300, 4400, 4500, 4600, 4700, 4800, 4900, 5100, 5200, 5300, 5400, 5500, 5600, 5700, 5800, 5900, 6600, 6200, 6300, 6400, 6500, 6600, 6700, 6800, 6900, 7100, 7200, 7300, 7400, 7500, 7600, 7700, 7800, 7900, 8100, 8200, 8300, 8400, 8500, 8600, 8700, 8800, 8900, 9100, 9200, 9300, 9400, 9500, 9600, 9700, 9800, 9900, or 10000 nucleotides.

In some embodiments, the architecture is two-dimensional and comprises a single layer of bricks or a single scaffold. The single layer of bricks may form a molecular canvas. In other embodiments, the architecture is three-dimensional and may contain 2, 3, 4, 5, 6, 7, 8, 9, 10, 20, 30, or more layers of two-dimensional structures depending on the desired final shape.

In some embodiments, the architecture is attached to a substrate, such as a glass slide, a silicon base, or a breadboard.

In other embodiments, the architecture remains in a solution. By altering aspects of the solution, such as but not limited to pH, salt concentrations, and cation charge, the aggregation of the bricks may be changed, which may change the orientation, as well as the absorbance spectra, of the chromophores.

Dyes

Any dye comprising at least one chromophore in which an exciton is created when excited is acceptable and may be used in any embodiment. A dye may be symmetrical or asymmetrical and may have additional modifications to change solubility, hydrophobicity, or symmetry in order to adjust the placement of the chromophore. By way of non-limiting examples, the dye may be one or more of a xanthene derivatives such as fluorescein, rhodamine, oregon green, eosin, and Texas red; cyanine derivatives such as cyanine, indocarbocyanine, oxacarbocyanine, thiacarbocyanine, and merocyanine; a squaraine derivative or ring-substituted squaraines such as Seta, SeTau, and Square dyes; a naphthalene derivative such as a dansyl or prodan derivative; a coumarin derivative; a oxadiazole derivative such as pyridyloxazole, nitrobenzoxadiazole and benzoxadiazole; an anthracene derivatives such as anthraquinones including DRAQS, DRAQ7 and CyTRAK Orange; a pyrene derivative such as cascade blue; an oxazine derivative such as Nile red, Nile blue, cresyl violet, oxazine 170; an acridine derivative such as proflavin, acridine orange, acridine yellow; and an arylmethine derivative such as auramine, crystal violet, and malachite green; a tetrapyrrole derivative such as porphin, phthalocyanine, and bilirubin. The aggregates may alternatively comprise one or more commercial dye(s), such as but not limited to Freedom™ Dye, Alexa Fluor® Dye, LI-COR IRDyes®, ATTO™ Dyes, Rhodamine Dyes, or WellRED Dyes; or any other dye. Examples of Freedom™ Dyes include 6-FAM, 6-FAM (Fluorescein), Fluorescein dT, Cy3™, TAMRA™, JOE, Cy5™, TAMRA, MAX, TET™, Cy5.5™, ROX, TYE™ 563, Yakima Yellow®, HEX, TEX 615, TYE™ 665, TYE 705, and Dyomic Dyes. Examples of Alexa Fluor® Dyes include Alexa Fluor® 488, 532, 546, 647, 660, and 750. Examples of LI-COR IRDyes® include 5' IRDye® 700, 800, and 800CW. Examples of ATTO™ Dyes include ATTO™ 488, 532, 550, 565, Rho101, 590, 633, 647N. Examples of Rhodamine Dyes include Rhodamine Green™-X, Rhodamine Red™-X, and 5-TAMRA™. Examples of WellREd Dyes include WellRED D4, D3, and D2. Examples of Dyomic Dyes include Dy-530, -547, -547P1, -548, -549, -549P1, -550, -554, -555, -556, -560, -590, -591, -594, -605, -610, -615, -630, -631, -632, -633, -634, -635, -636, -647, -647P1, -648, -648P1, -649, -649P1, -650, -651, -652, -654, -675, -676, -677, -678, -679P1, -680, -681, -682, -700, -701, -703, -704, -705, 730, -731, -732, -734, -749, -749P1, -750, -751, -752, 754, -756, -757, -758, -780, -781, -782, -800, -831, -480XL, -481XL, -485XL, -510XL, -511XL, -520XL, -521XL, -601XL. Examples of other dyes include squaraine, 6-FAM, Fluorescein, Texas Red®-X, and Lightcycler® 640.

In some embodiments, the dyes are bound to the 5' ends of the nucleotide bricks. In other embodiments, the dyes are bound to the 3' ends of the nucleotide bricks. In yet other embodiments, the dyes are bound internally within the nucleotide bricks. In still more embodiments, the dyes are bound to any mix of 5' ends, 3' ends, or internally. The position of the chromophore within the dye will depend on the desired final configuration. Methods of binding dyes to nucleotides is well known in the art.

In some embodiments, the dyes are bound to the same nucleotide duplex. In other embodiments, the dyes are bound to separate nucleotide duplexes.

In some embodiments, some of the dyes are covalently bound to the bricks while other of the dyes are bound to separate oligomers, a linker nucleotide oligomer, and the linker oligomers then Watson-Crick pair with exposed single strands of the bricks.

In some embodiments the dyes are not bound to DNA.

Dyes, commercially available, including custom dyes, or dyes produced in-house may also be modified to control their steric hindrance or their symmetry, as described in U.S. application Ser. No. 16/739,963 (herein incorporated in its entirety). For example, by substituting a ring structure like rotaxane around the chromophores their steric hindrance may be increased to prevent H-like aggregation or to hold them in a more desired configuration. The ring structure may be further substituted to increase steric hindrance. Further, the number of rings may be increased to increase steric hindrance.

Dye Aggregates

When two or more dyes are placed sufficiently close to each other to couple, they may form an aggregate. The stronger the coupling of the dye chromophores within the aggregate, the greater the peak shift relative to the monomer or the greater the Davydov splitting (i.e., splitting of the monomeric electronic energy levels) will be. Aggregates have different properties than the chromophores that make up the aggregate as can be seen in the differences between the Hamiltonians between an aggregate and a single chromophore.

The aggregate based excitonic quantum coherent effects may occur at room temperature in wet and noisy environments and the systems may be less than about 10 nm. These systems provide several large benefits over the currently available excitonic quantum coherent systems, which are much larger, measuring in the micrometer size, and require extreme operating conditions, such as cryogenic temperatures, external magnetic fields and/or large microwave pulses, and dry environments.

When dyes aggregate in high concentrations in solution, coherent exciton delocalization behavior (e.g., large Davydov splitting, exchange narrowing, circular dichroism, Cotton effects, or Stokes shifting) can be observed. The circular dichroism may be either right- or left-handed and so may absorb light having particular circular polarization.

Using the above architectures, one or more dyes, each comprising at least one chromophore or fluorophore, may be placed in precise distances from each other to create different coupling strengths of their dipoles unlike relying on high aggregation concentration in a solution. At sufficiently short distances on these architectures, the dipoles of two or more chromophores residing on one or more dyes may become weakly or strongly coupled and may form an aggregate for exciton sharing or transfer. Alternatively, the dipoles may be positioned to allow very weak coupling for FRET.

In some embodiments, using the above architectures, two or more dyes may be bound to the nucleotides in order to be precisely placed so that the chromophores create weakly or strongly coupled aggregates. When so placed, the aggregates may produce quantum coherent excitons, biexcitons, and triexcitons when excited by a light source. In some exemplary embodiments, the two or more dyes are covalently bound to the same nucleotides brick, and then the dye-bound brick and any non-bound bricks are allowed to self-assemble into the desired final one-, two-, or three-dimensional shape. In another embodiment, the two or more dyes are covalently bound to different nucleotide bricks and then the bricks are allowed to self-assemble into the desired final one-, two-, or three-dimensional shape. Another embodiment is combination thereof, in which some bricks have one while other bricks have multiple bound dyes. The bricks once assembled place the dyes within their aggregate.

In some embodiment, the bricks, which may already have bound dyes, are allowed to first self-assemble into the desired final one-, two-, or three-dimensional shape. Portions of the bricks may still be unpaired after assembly, allowing for further binding of complementary oligomers. The two or more chromophores are bound to at least one complementary oligomer which may then pair with the one or more unpaired portions of the bricks.

The orientation of the two or more chromophore transition dipole moments, occurring within the dyes, to each other may affect the absorbance and emission spectra of the aggregate. Depending on the orientation, a pair of chromophores (dimer) sufficiently close to allow weak to strong excitonic coupling will have different characteristics when compared to the monomer chromophore. When the dipoles are parallel in the dimer an "H-dimer" forms that shows H-like stacking, or H-like coupling, which is characterized by a blue-shift in absorbance due to having a higher excited energy state when compared to the monomer. When the dipoles are in a head-to-head orientation in a dimer, a "J-dimer" forms that shows J-like stacking, or J-like coupling, which is characterized by a red-shift in absorbance due to having a lower excited energy state when compared to a monomer. When the transition dipole moments of a dimer are about 90 degrees, the dimer is defined as an oblique dimer, in which an equally mixed "J/H-dimer" forms. Here, Davydov splitting is observed in the absorbance spectrum because both a higher and lower excited energy state are allowed by selection rules when compared to a monomer (see Cannon et al., *Coherent Exciton Delocalization in a Two-State DNA-Templated Dye Aggregate System*, 2017, J. Phys. Chem. A, 121: 6905-6916, herein incorporated by reference). For those dimers that are not purely J-like or H-like, nor purely oblique, both energy states are allowed to different degrees dependent on the angle between them. When weakly allowed, the states may not be optically observable in the absorbance spectrum.

As taught in U.S. patent application Ser. No. 16/100,052 (herein incorporated by reference in its entirety), the orientation of the chromophores within an aggregate on a linear oligomer is also affected by characteristics of the solution, including salt concentration, temperature, and cation concentration. The orientation may affect the absorbance spectra. Therefore, by altering the conditions of the solution, it is possible to fine tune the absorbance spectra of the aggregates. For example, as the salt concentration increases, a dimer aggregate may be fine-tuned to exhibit either J-dimer characteristics at lower salt concentrations or H-dimer characteristics at high salt concentrations. Also, altering both the temperature and salt concentrations, it is further possible to tune the chromophores for specific characteristics as not only the absorbance, but the emission may be altered by changing the concentration of salt in the solution.

Additionally, the absorbance spectrum of the aggregates on a linear oligomer is also affected by the spacing of the chromophores comprising the aggregate. As the distance increases between the chromophores, coupling is decreased which leads to diminished spectral absorbance shifts from that of the monomeric dyes and the absorbance spectrum approaches that of the monomer. In order for strong coupling to occur in dye aggregates, dyes must be closely spaced, but to prevent two aggregates behaving as a single aggregate, an aggregate must be spaced so that they are weakly coupled with another aggregate.

Taken together, by altering the composition of the solution surrounding the nucleotide architecture and by altering the distance between the chromophores and aggregates, one skilled in the art may alter the absorbance and emission spectra for an aggregate comprised of two or more chromophores bound to a nucleotide architecture.

In a preferred embodiment, an aggregate comprises at least two dyes are held by an architecture so that the chromophores are in a head-to-tail or head-to-head orientation to form a J-dimer. In another preferred embodiment, three dyes are held so that the chromophores are in a head-to-tail or head-to-head orientation to form a triangular J-trimer (FIG. 1).

Other embodiments comprising J-dimers may also be used. In another embodiment, the aggregate comprises at least two chromophores held oblique to each other by an architecture to form a mixed J/H-dimer.

In another embodiment, an aggregate comprises at least three chromophores are positioned within the architecture so that two of the three chromophores form a J-dimer, and two of the three chromophores form a H-dimer. In a different embodiment, an aggregate comprises chromophores positioned such that two form a J-dimer and the third forms two mixed J/H-dimers. In yet another embodiment, an aggregate comprises three chromophores with two chromophores forming a H-dimer and the third forms two mixed J/H-dimers.

In yet another embodiment, an aggregate comprises a tetramer of chromophores positioned within the architecture such that two H-dimers, two J-dimers are formed, and two mixed J/H-dimers form. In other embodiments, the tetramer can be position so that two H-dimers and four mixed J/H-dimers are formed. In yet another embodiment, the tetramer is positioned so that two J-dimers and four mixed J/H-dimers are formed.

In some embodiments, an aggregate comprises chromophores which all have the same optical transition energies. In other embodiments, the chromophores differ in their optical transition energies. The different optical transition energies allow the construction of a set phase shifter having desired values of absorbance and emittance.

In other embodiments, the basic configurations dimer, trimers, and tetramers as described above can be joined with other monomers, dimer, trimers, and tetramers in order to form more complex aggregates. An aggregate may comprise of any number of chromophores, for example an aggregate may comprise of 2 or more, 3 or more, 4 or more, 5 or more, 7 or more, 10 or more, or 15 or more chromophores. Preferably an aggregate may comprise from between 2 and 20 chromophores, from between 2 and 15 chromophores, from between 2 and 10 chromophores, or from between 2 and 5 chromophores. In a most preferred embodiment, the aggregate comprises of a dimer or trimer of chromophores.

In other embodiments, the chromophores are covalently bonded together chemically. In still further embodiments, the chromophores are both covalently bonded together and placed on a nucleotide architecture.

Optically Active Medium

A medium comprising of the chromophore aggregates with J-like stacking may be used in any optical system. Optically active medium comprising of chromophore aggregates are more amenable to the miniaturization required for integrated optics than current electric based systems. Current systems, such as those relying on magnetism or wave plates, are bulky and require microsized space for the components.

However, given the scale of the chromophore aggregates and the optional nucleotide architectures, together still on the nanometer scale, the optically active medium described herein requires little space and so may be more easily integrated into various optical devices.

In an embodiment, the optically active medium comprises one or more chromophore aggregate having J-like coupling. The optically active medium may further comprise salts and/or a nucleotide scaffolding to hold the chromophores in the proper orientation for J-like coupling within the aggregates. In preferred embodiments, the aggregates are chromophore dimers or trimers wherein the chromophores are arranged end-to-end, for example head-to-tail and/or head-to-head, to align their planes (FIG. 1).

The orientation of the plane of a population of aggregates within the medium to the direction of propagation of light will affect the amount of optical activity of the medium. Randomly orientated with an isotropic distribution within the medium will display optically activity while the more perpendicular the planes are to the direction of light propagation the stronger the optical activity will become. Therefore, depending on the desired strength of the optically active medium, the planes of a population of chromophore aggregates may vary within the media. In a preferred embodiment, the planes of the chromophore aggregates within the medium are held perpendicular to the propagation of light. Any percent of the population of the chromophore aggregates may be perpendicular to the propagation of light, for example up to about 1%, up to about 5%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, up to about 90%, up to about 95%, up to about 100%.

Optical Devices

The optically active medium may be used in any optical device. Preferable devices are nonreciprocal devices, such as optical isolators, circulators, and/or switches. Even more preferably, the devices are optically pumped and nonreciprocal devices (for example, see FIG. 2). Nonreciprocal devices, such as isolators and circulators, are well known in the art. For example, see U.S. Pat. Nos. 10,353,337, 9,164, 350, 6,553,156, 4,822,150, and Z. Shen et al. (Reconfigurable optomechanical circulator and directional amplifier, Nat. Commun. 9, 1797 (2018); DOI: 10.1038/s41467-018-04187-8) (all incorporated herein in their entirety).

In nonreciprocal pumped optical devices, it is preferable that the signal light be able to travel in both directions, the pump light is circularly polarized, and a first dichroic mirror is configured to collinearly combine the signal and pump lights prior to the optically active media and a second dichroic mirror is configured to separate the lights after the mixed light travels through the optically active media.

The pump light, having a circular polarization, induces circular dichroic activity in the optically active medium. Once activated, the optically active medium disclosed herein only permits the flow of signal light in one direction as the signal light traveling through the device will experience a differing amount of attenuation or phase shift depending on whether its circular polarization is left-handed or right-handed.

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

1 Introduction

Figure 2:
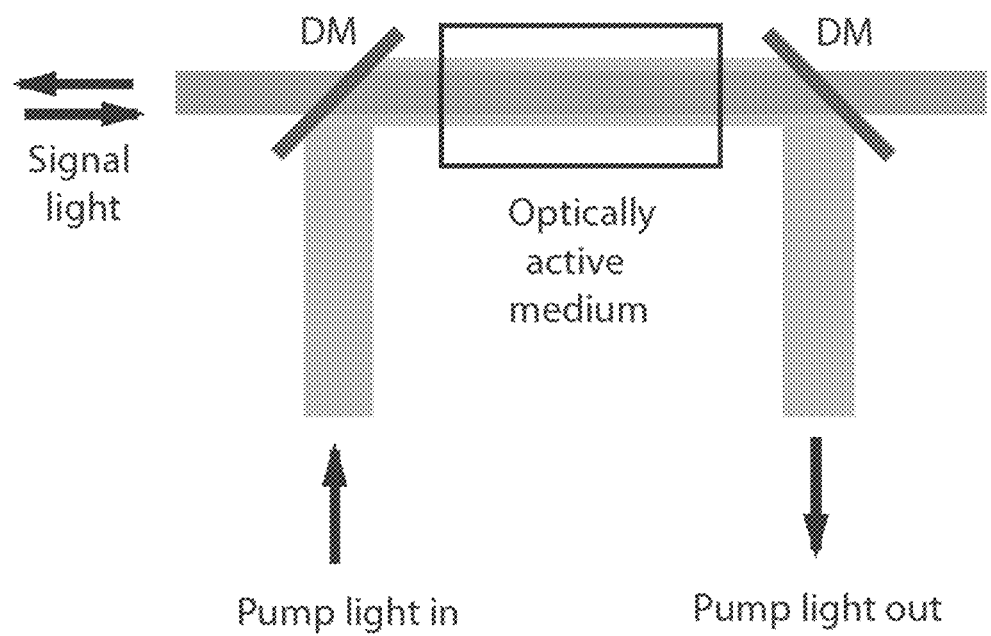
FIG. 2 shows an example of an optically pumped nonreciprocal device. Pump light and signal light are combined collinearly or separated via dichroic mirrors (DM). The signal light can propagate in either direction through the device. The pump beam is circularly polarized thereby inducing circular dichroic activity in the optically active medium. The medium consists of chromophore aggregates arranged end-to-end to create J-like coupling. Ideally the aggregates would all be oriented with their plane's perpendicular to the direction of propagation of the light beams; however, even if they are randomly oriented with an isotropic distribution, they will still display optical activity. Signal light passing through the device will experience a differing amount of attenuation or phase shift depending on whether its circular polarization is left-handed or right-handed. The effect on the two components of circular polarization depends on the direction with which the signal light propagates through the device, making the device nonreciprocal. This device can serve as an element of an isolator or circulator. Other device configurations are possible that take advantage of the optically pumped circular dichroism of the chromophore aggregate.

Here is presented an analysis of the energy levels and the strengths of the optical transitions for a three-site chromophore aggregate in which the chromophores are coupled with a J-like stacking. An example of such a chromophore aggregate is depicted in FIG. 1. The purpose of the analysis was to assess the suitability of such aggregates to serve as optically active elements in optically pumped nonreciprocal devices. An example of such a device is shown in FIG. 2. Nonreciprocal devices called isolators and circulators fined extensive use in radio-frequency microwave and optical systems. Isolators are often used to protect a transmitter from back reflection of the transmitted power. Such back reflection can lead to instabilities or degraded performance of the transmitter or laser and in high-power applications can lead to the failure of the transmitter or laser. Isolators only allow power to flow in one direction through them. Hence, they are nonreciprocal devices since what happens to the signal depends on which direction the signal passes through the device. Circulators are another example of a nonreciprocal device. This device is capable of directing power flow. For example, consider a three-port circulator and let the ports be numbered 1, 2, and 3. In such a circulator power (or signal) entering port 1 is delivered as output to port 2, power (or signal) entering port 2 is delivered as output to port 3, power (or signal) entering port 3 is delivered as output to port 1. Circulators are useful in separating signals propagating in opposite directions along a radio-frequency transmission line (coaxial cable for example), microwave waveguides, and optical numbers. This enables signals to be simultaneously sent in both directions along a transmission line. Other examples of the application of circulators include the separation of the input port from the output port of a reflection parametric amplifier or optical cavity-based devices having only one port. For the latter reason optical circulators could be extremely useful devices for optical computing, especially diamond color-center-based quantum computing in which optical cavities are used to couple light to the color centers.

Most isolators and circulators employ the Faraday rotation effect for their operation. This requires that a material medium through which the signal propagates be placed in an intense magnetic field. As a result, circulators and isolators are bulky devices and specifically not suitable as integrated optical components.

An alternative approach, more amenable to the miniaturization required for integrated optics, is to optically pump a material medium with circularly polarized light to induce nonreciprocal behavior. For this purpose, one would like a material in which a strong circular dichroic effect can be induced by optical pumping with circularly polarized light. The search for materials exhibiting such effects is an active area of research.

Recently, DNA nanotechnology has enabled the controlled assembly of dye aggregates. The optical properties of such aggregates are strongly influenced by the geometry of the aggregate. Such aggregates with the right geometry may make high quality optically active materials exhibiting a large circular dichroism effect when pumped with circularly polarized light.

Here an analysis is carried out of three-dye aggregates in which the dyes are coupled end-to-end in what is referred to as J coupling. The quantum of energy absorbed by a dye aggregate when illuminated by light is called an exciton. This quantum of energy behaves like a quantum mechanical particle and has both particle-like and wave-like properties. It becomes delocalized over the entire aggregate thereby altering the aggregate's optical properties from that of a single dye. In addition, excitons can interact with each other. If the dyes do not have an energy level close to twice the exciton energy, the excitons act like hard-core particles, that is, two excitons cannot reside on the same molecule at the same time.

Figure 3:
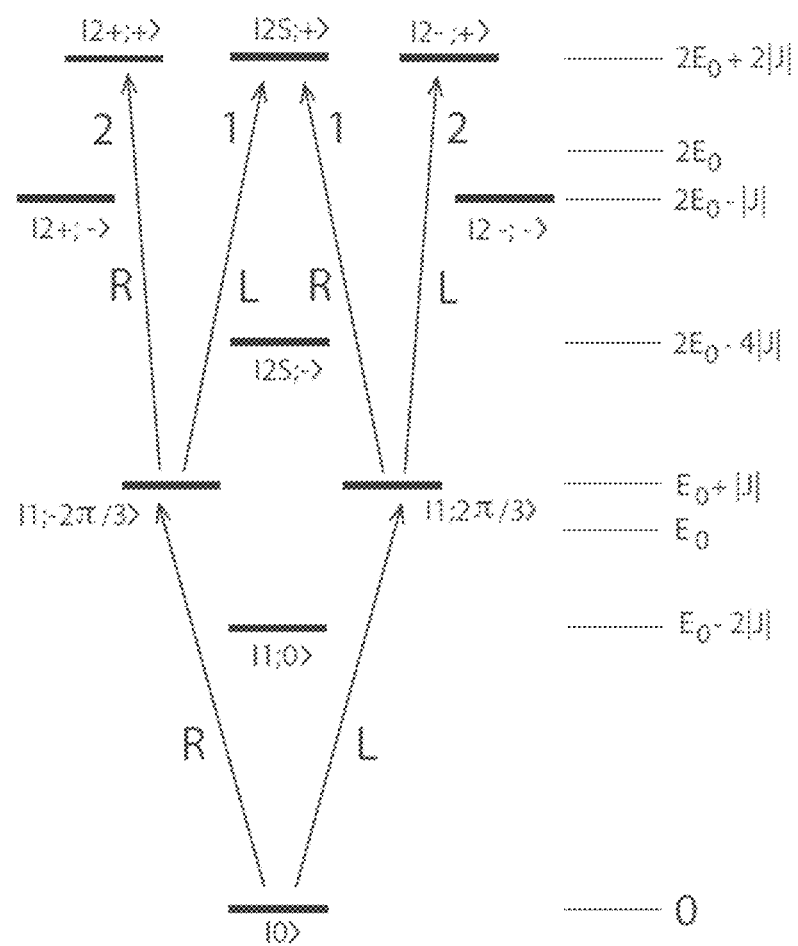
FIG. 3 shows a graphical depiction of the energy levels and allowed optical transitions starting from the ground state $|0\rangle$ for the case when $K=\Delta=0$ and the plane of the aggregate is perpendicular to the direction of light propagation. L and R denote transitions involving left-handed or right-handed circularly polarized light. The numbers 1 and 2 on the transition arrows from the one-exciton states to the two-exciton states indicate the relative transition rates. An undesirable aspect of this system of energy levels is that the transition energy of the optically allowed transitions from the ground state to the one-exciton states are the same as the optically allowed transitions from these one-exciton states to the two-exciton states, namely, that transition energy is $E_0+|J|$. This makes separation of the pump and signal difficult.
Figure 4:
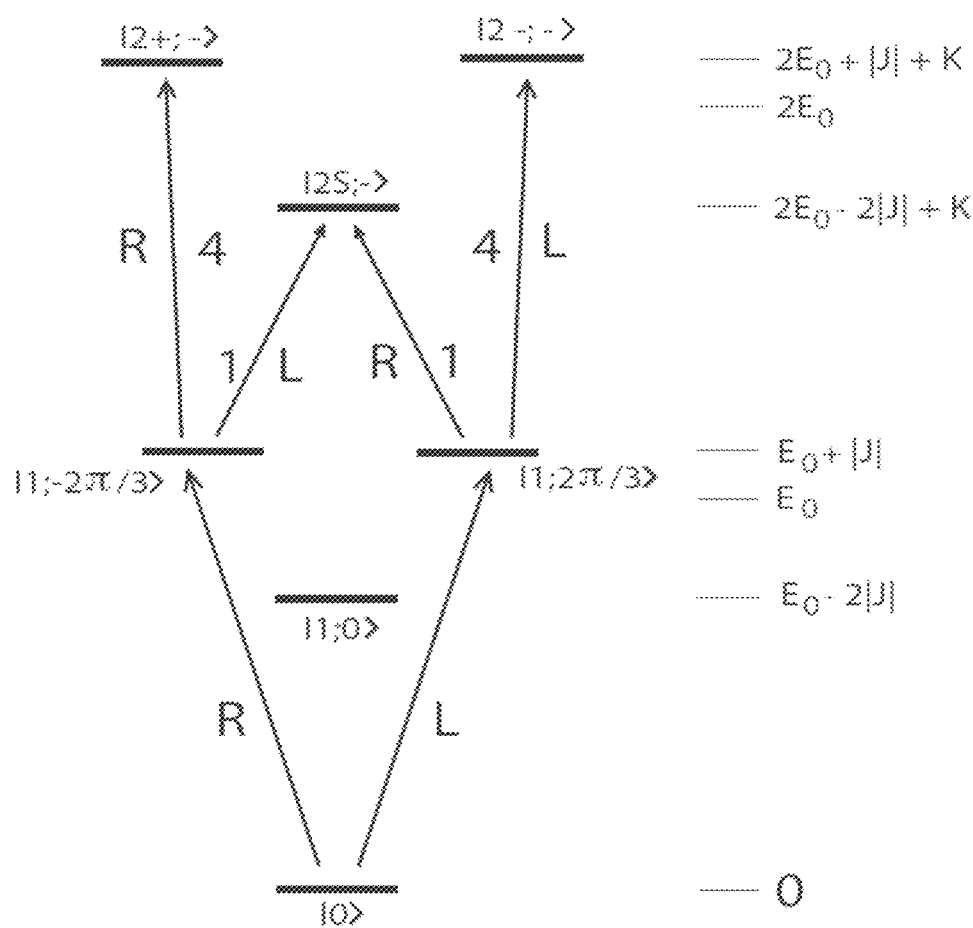
FIG. 4 shows a graphical depiction of the energy levels and allowed optical transitions starting from the ground state $|0\rangle$ for the case when the anharmonicity parameter $\Delta=\infty$ and the plane of the aggregate is perpendicular to the direction of light propagation. In this case the excitons are behaving as hard-core bosons and satisfy Paulion statistics. L and R denote transitions involving left-handed or right-handed circularly polarized light. The numbers 1 and 4 on the transition arrows from the one-exciton states to the two-exciton states indicate the relative transition rates. In contrast to the case when $\Delta=K=0$, where K=the inter-site two-exciton interaction parameter, the degeneracy has been broken between the optically allowed transition energy from the ground state to the single-exciton excited states and the optically allowed transition energies from the single-exciton excited states to the optically allowed two-exciton excited states. In particular, the transition energy from $|0\rangle$ to $|1; -2\pi/3\rangle$ is $E_0+|J|$, whereas the transition energy from $|1; -2\pi/3\rangle$ to $|2S; -\rangle$ is $E_0-3|J|+K$ and the transition from $|1; -2\pi/3\rangle$ to $|2+; -\rangle$ is $E_0+K$. As a consequence, the laser beam exciting from the ground state to the first excited state can be left on while light at a one-exciton to two-exciton transition is applied. Note that only one polarization of this applied light will be absorbed. Hence, a collection of such oriented dyes will exhibit a strong circular dichroism that is switchable by changing the circular polarization of the pump light from one circular polarization state to the other. The system also will behave as a non-reciprocal device in which the circular polarization state attenuated depends on whether the applied light is propagating along in the same direction as the pump light or in the opposite direction.
Figure 5:
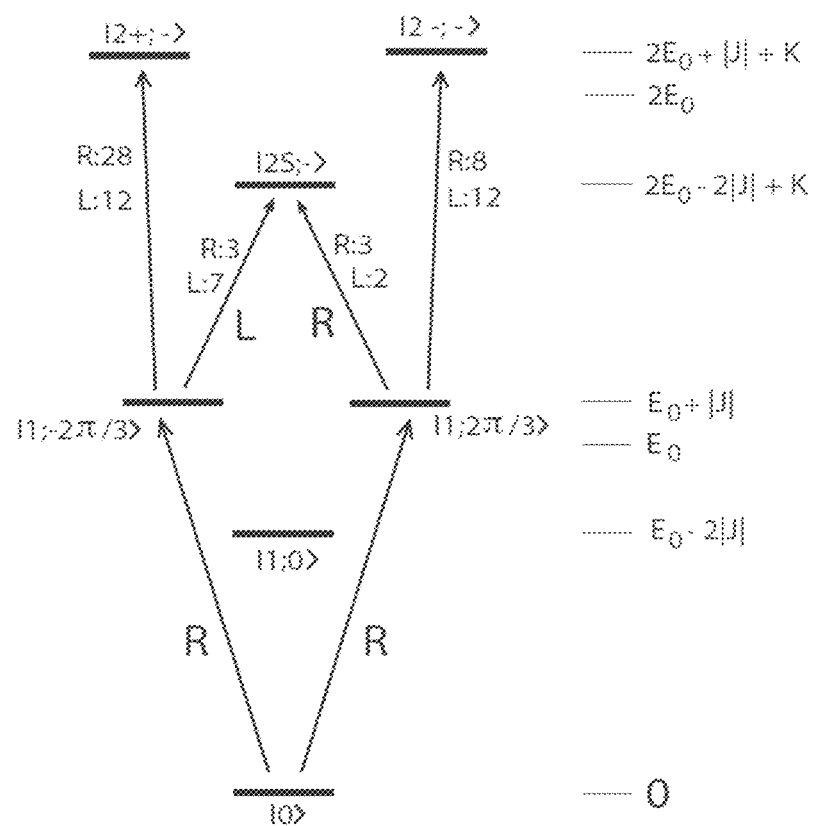
FIG. 5 shows a graphical depiction of the energy levels and allowed optical transitions starting from the ground $|0\rangle$ for the case when $\Delta=\infty$ and the aggregates are randomly oriented with an isotropic distribution, such as would be the case if the aggregates were in solution. Here is depicted the case when the pump is right-hand circularly polarized. Because the aggregates are randomly oriented, both the $|1; -2\pi/3\rangle$ and the $|1; 2\pi/3\rangle$ states are excited by the pump, but in different ratios if the pump light is not of sufficient intensity to saturate the transitions. The R:x and L:y indicate the relative absorbance x and y for right R and L circularly polarized light, respectively, when none of the transitions are saturated. For example, consider the case of a signal light having the energy $E_0+K$. The ratio of absorbance of right-handed to left-handed circularly polarized light is R:L=(28+8):(12+12)=3:2. That is, the absorbance of right-hand circularly polarized light is 1.5 times greater than that of left-hand circularly polarized light. Similarly, for the transitions to the $|2S; -\rangle$ state, R:L=(3+3):(7+2)=2:3. Hence, when the aggregates in the system have an isotropic distribution one still has a substantial circular dichroism effect.

Frenkel-exciton theory has been highly successful in predicting the optical properties of dye aggregates. This theory has been used in the analysis presented here. The analysis proceeds by first computing the energy levels (energy eigenvalues) of the aggregate. This is done by diagonalizing the Frenkel Hamiltonian governing exciton behavior. Since one is considering an optically pumped system, an analysis must be carried out in which both the one-exciton and two-exciton states are evaluated. Once the energy eigenvectors and energy eigenvalues have been computed, the strength of the optical transitions between the states are computed. The results are summarized in FIGS. 3,

4, and 5. The suitability of the dye aggregates as the active material for optically pumped nonreciprocal devices can then be judged.

1.1 Major Conclusions

1. A system of chromophores in which the excitons do not interact is not well suited for the applications being discussed because the signal and pump frequencies (wavelengths) would have to be close, potentially causing interference of the pump light with the signal light if the pump light pulse overlaps the signal light pulse.
2. Both the one-site two-exciton interaction parameterized by the anhamonicity parameter $\Delta$ and the inter-site two-exciton interaction parameterized by K can break the degeneracy between the signal frequency and the pump frequency to eliminate spectral overlap.
3. For the case of hard core excitons $\Delta=\infty$ one gets ideal performance in that signal with a given circular polarization will propagate through the medium unattenuated while signal with the opposite circular polarization is strongly attenuated. This is ideal isolator performance. Achieving this performance requires all the aggregates to be oriented with their planes perpendicular to the direction of light propagation. Such anisotropic materials can be constructed using liquid-crystal ordering techniques to align all the aggregates.
4. Even for the case when the aggregates are isotropically oriented as in the case when they are dispersed in a fluid, the system will still exhibit circular dichroism although with reduced contrast. It was calculated that the ratio of attenuation of signal light for the states of circular polarization is 3 to 2.

1.2 Caveats

The analysis did not include vibronic effects. It is known that molecular vibrations have a significant effect on the optical spectra of dyes and dye aggregates. Such effects can be modeled using the Holstein Hamiltonian, but the computations are more complex and generally require numerical computation. It is possible that vibronic effects will degrade performance. However, it is still likely that the aggregate will exhibit optically pumped circular dichroic effects of sufficient strength to be useful in device applications.

2 A Rotationally-Symmetric Aggregate System with J-Like Stacking, General Case

Here we consider the three-site problem system governed by the Frenkel Hamiltonian $$H = H_0 + H_J + H_\Delta + H_K, \tag{1}$$

where $$H_0 = \sum_{r=1}^{3} E_0 a_r^\dagger a_r, \tag{2}$$

$$H_J = J(a_1^\dagger a_2 + a_2^\dagger a_1 + a_2^\dagger a_3 + a_3^\dagger a_2 + a_3^\dagger a_1 + a_1^\dagger a_3), \tag{3}$$

$$H_\Delta = \sum_{r=1}^{3} \frac{\Delta}{2} a_r^\dagger a_r^\dagger a_r a_r, \tag{4}$$

and $$H_K = K(a_1^\dagger a_2^\dagger a_2 a_1 + a_2^\dagger a_3^\dagger a_3 a_2 + a_3^\dagger a_1^\dagger a_1 a_3). \tag{5}$$

3 Single Exciton Energy Eigenstates

The symmetry adapted single exciton energy eigenstates are $$|1;0\rangle = \frac{1}{\sqrt{3}}(a_1^\dagger + a_2^\dagger + a_3^\dagger)|0\rangle, \tag{6}$$

$$|1;2\pi/3\rangle = \frac{1}{\sqrt{3}}(a_1^\dagger + e^{i2\pi/3} a_2^\dagger + e^{i4\pi/3} a_3^\dagger)|0\rangle \tag{7}$$

and $$|1;-2\pi/3\rangle = \frac{1}{\sqrt{3}}(a_1^\dagger + e^{-i2\pi/3} a_2^\dagger + e^{-i4\pi/3} a_3^\dagger)|0\rangle. \tag{8}$$

One has $$e^{i2\pi/3} = \cos(2\pi/3) + i\sin(2\pi/3) = -\frac{1}{2} + i\frac{\sqrt{3}}{2} \tag{9}$$

and $$e^{i4\pi/3} = \cos(4\pi/3) + i\sin(4\pi/3) = -\frac{1}{2} - i\frac{\sqrt{3}}{2}. \tag{10}$$

One has $$H|1;0\rangle = (E_0+2J)|1;0\rangle \tag{11}$$

$$H|1;2\pi/3\rangle = (E_0-J)|1;2\pi/3\rangle \tag{12}$$

$$H|1;-2\pi/3\rangle = (E_0-J)|1;-2\pi/3\rangle. \tag{13}$$

We now introduce the annihilation operators $$b_0 = \frac{1}{\sqrt{3}}(\alpha_1 + a_2 + a_3), \tag{14}$$

$$b_{2\pi/3} = \frac{1}{\sqrt{3}}(\alpha_1 + e^{-i2\pi/3} a_2 + e^{-i4\pi/3} \alpha_3), \tag{15}$$

and $$b_{-2\pi/3} = \frac{1}{\sqrt{3}}(a_1 + e^{i2\pi/3} a_2 + e^{i4\pi/3} a_3). \tag{16}$$

The inverse transformation is $$a_1 = \frac{1}{\sqrt{3}}(b_0 + b_{2\pi/3} + b_{-2\pi/3}), \tag{17}$$

$$\alpha_2 = \frac{1}{\sqrt{3}}(b_0 + e^{i2\pi/3} b_{2\pi/3} + e^{i4\pi/3} b_{-2\pi/3}), \tag{18}$$

and $$a_3 = \frac{1}{\sqrt{3}}(b_0 + e^{-i2\pi/3} b_{2\pi/3} + e^{-i4\pi/3} b_{-2\pi/3}). \tag{19}$$

One has $$a_1^\dagger a_1 + a_2^\dagger a_2 + a_3^\dagger a_3 = b_0^\dagger b_0 + b_{2\pi/3}^\dagger b_{2\pi/3} + b_{-2\pi/3}^\dagger b_{-2\pi/3} \tag{20}$$

and $$a_1^\dagger a_2 + a_2^\dagger a_1 + a_2^\dagger a_3 + a_3^\dagger a_2 + a_3^\dagger a_1 + a_1^\dagger a_3 = 2b_0^\dagger b_0 - b_{2\pi/3}^\dagger b_{2\pi/3} - b_{-2\pi/3}^\dagger b_{-2\pi/3}. \tag{21}$$

Hence, if $$\Delta = K = 0, \tag{22}$$

then $$H = (E_0+2J) b_0^\dagger b_0 + (E_0-J) b_{2\pi/3}^\dagger b_{2\pi/3} + (E_0-J) b_{-2\pi/3}^\dagger b_{-2\pi/3}. \tag{23}$$

In this case the single particle energy eigenstates are $$|1;0\rangle = b_0^\dagger |0\rangle \tag{24}$$

$$|1;2\pi/3\rangle = b_{2\pi/3}^\dagger |0\rangle \tag{25}$$

$$|1;-2\pi/3\rangle = b_{-2\pi/3}^\dagger |0\rangle. \tag{26}$$

The corresponding energy eigenvalues are $$E_{1;0} = E_0 + 2J \tag{27}$$

$$E_{1;2\pi/3} = E_0 - J \tag{28}$$

$$E_{1;-2\pi/3} = E_0 - J. \tag{29}$$

The two particle energy eigenstates are $$|2;0,0\rangle = b_0^\dagger b_0^\dagger |0\rangle, \tag{30}$$

$$|2;0,2\pi/3\rangle = b_0^\dagger b_{2\pi/3}^\dagger |0\rangle, \tag{31}$$

$$|2;0,-2\pi/3\rangle = b_0^\dagger b_{-2\pi/3}^\dagger |0\rangle, \tag{32}$$

$$|2;2\pi/3,-2\pi/3\rangle = b_{2\pi/3}^\dagger b_{-2\pi/3}^\dagger |0\rangle, \tag{33}$$

$$|2;2\pi/3,2\pi/3\rangle = b_{2\pi/3}^\dagger b_{2\pi/3}^\dagger |0\rangle, \tag{34}$$

$$|2;-2\pi/3,-2\pi/3\rangle = b_{-2\pi/3}^\dagger b_{-2\pi/3}^\dagger |0\rangle. \tag{35}$$

The corresponding energy eigenvalues are $$E_{2;0,0} = 2E_0 + 4J, \tag{36}$$

$$E_{2;0,2\pi/3} = 2E_0 + J, \tag{37}$$

$$E_{2;0,-2\pi/3} = 2E_0 + J, \tag{38}$$

$$E_{2;2\pi/3,-2\pi/3} = 2E_0 - 2J, \tag{39}$$

$$E_{2;2\pi/3,2\pi/3} = 2E_0 - 2J, \tag{40}$$

$$E_{2;-2\pi/3,-2\pi/3} = 2E_0 - 2J. \tag{41}$$

4 Two Exciton Energy Eigenstates

The symmetry adapted two exciton states are $$|2Sa\rangle = \frac{1}{\sqrt{6}} \left( a_1^\dagger a_1^\dagger + a_2^\dagger a_2^\dagger + a_3^\dagger a_3^\dagger \right) |0\rangle, \tag{42}$$

$$|2Sb\rangle = \frac{1}{\sqrt{3}} \left( a_1^\dagger a_2^\dagger + a_2^\dagger a_3^\dagger + a_3^\dagger a_1^\dagger \right) |0\rangle, \tag{43}$$

$$|2a+\rangle = \frac{1}{\sqrt{6}} \left( a_1^\dagger a_1^\dagger + e^{i2\pi/3} a_2^\dagger a_2^\dagger + e^{i4\pi/3} a_3^\dagger a_3^\dagger \right) |0\rangle, \tag{44}$$

$$|2b+\rangle = \frac{1}{\sqrt{3}} \left( a_1^\dagger a_2^\dagger + e^{i2\pi/3} a_2^\dagger a_3^\dagger + e^{i4\pi/3} a_3^\dagger a_1^\dagger \right) |0\rangle, \tag{45}$$

$$|2a-\rangle = \frac{1}{\sqrt{6}} \left( a_1^\dagger a_1^\dagger + e^{-i2\pi/3} a_2^\dagger a_2^\dagger + e^{-i4\pi/3} a_3^\dagger a_3^\dagger \right) |0\rangle, \tag{46}$$

$$|2b-\rangle = \frac{1}{\sqrt{3}} \left( a_1^\dagger a_2^\dagger + e^{-i2\pi/3} a_2^\dagger a_3^\dagger + e^{-i4\pi/3} a_3^\dagger a_1^\dagger \right) |0\rangle. \tag{47}$$

One has $$H|2Sa\rangle = 2E_0|2Sa\rangle + 2\sqrt{2}J|2Sb\rangle + \Delta|2Sa\rangle, \tag{48}$$

$$H|2Sb\rangle = 2E_0|2Sb\rangle + 2J|2Sb\rangle + 2\sqrt{2}J|2Sa\rangle + K|2Sb\rangle. \tag{49}$$

Hence on the $|2Sa\rangle$, $|2Sb\rangle$ subspace the Hamiltonian has the matrix form $$H = \begin{bmatrix} 2E_0 + \Delta & 2\sqrt{2}J \\ 2\sqrt{2}J & 2E_0 + 2J + K \end{bmatrix}. \tag{50}$$

The energy eigenvalues of this Hamiltonian are $$E = 2E_0 + J + \frac{\Delta + K}{2} \pm \frac{1}{2}\sqrt{(2J + K - \Delta)^2 + 32J^2}. \tag{51}$$

When $$\Delta = K = 0 \tag{52}$$

the energy eigenvalues become $$E_+ = 2E_0 + 4J, \tag{53}$$

$$E_- = 2E_0 - 2J. \tag{54}$$

One has $$H|2a+\rangle = 2E_0|2a+\rangle + \sqrt{2}J(1+e^{i2\pi/3})|2b+\rangle + \Delta|2a+\rangle \tag{55}$$

and $$H|2b+\rangle = 2E_0|2b+\rangle - J|2b+\rangle + \sqrt{2}J(1+e^{-i2\pi/3})|2a+\rangle + K|2b+\rangle. \tag{56}$$

Hence on the $|2a+\rangle$, $|2b+\rangle$ subspace the Hamiltonian has the matrix representation $$H = \begin{bmatrix} 2E_0 + \Delta & \sqrt{2}J(1+e^{i2\pi/3}) \\ \sqrt{2}J(1+e^{-i2\pi/3}) & 2E_0 - J + K \end{bmatrix}. \tag{57}$$

The energy eigenvalues of this Hamiltonian are $$E = 2E_0 + \frac{-J + K + \Delta}{2} \pm \frac{1}{2}\sqrt{(-J + K - \Delta)^2 + 8J^2}. \tag{58}$$

When $$\Delta = K = 0 \tag{59}$$

the energy eigenvalues become $$E_+ = 2E_0 + J, \tag{60}$$

$$E_- = 2E_0 - 2J. \tag{61}$$

One has $$H|2a-\rangle = 2E_0|2a-\rangle + \sqrt{2}J(1+e^{-i2\pi/3})|2b-\rangle + \Delta|2a-\rangle \tag{62}$$

and $$H|2b-\rangle = 2E_0|2b-\rangle - J|2b-\rangle + \sqrt{2}J(1+e^{i2\pi/3})|2a-\rangle + K|2b-\rangle. \tag{63}$$

Hence on the $|2a-\rangle$, $|2b-\rangle$ subspace the Hamiltonian has the matrix representation $$H = \begin{bmatrix} 2E_0 + \Delta & \sqrt{2}J(1+e^{-i2\pi/3}) \\ \sqrt{2}J(1+e^{i2\pi/3}) & 2E_0 - J + K \end{bmatrix}. \tag{64}$$

The energy eigenvalues of this Hamiltonian are $$E = 2E_0 + \frac{-J + \Delta + K}{2} \pm \frac{1}{2}\sqrt{(-J + K - \Delta)^2 + 8J^2}, \tag{65}$$

When $$\Delta = K = 0 \tag{66}$$

the energy eigenvalues become $$E_+ = 2E_0 + J, \tag{67}$$

$$E_- = 2E_0 - 2J. \tag{68}$$

5 Dipole Vectors

The orientation vectors of the molecules are taken to be $$n_1 = i, \tag{69}$$

$$n_2 = -\frac{1}{2}i + \frac{\sqrt{3}}{2}j, \tag{70}$$

$$n_3 = -\frac{1}{2}i - \frac{\sqrt{3}}{2}j. \tag{71}$$

The polarization vector of the aggregate is $$\mu = \mu \sum_{i=1}^{3} (a_i^\dagger + a_i) n_i \tag{72}$$

We write this as $$\mu = \mu^+ + \mu^- \tag{73}$$

where $$\mu^+ = \mu \sum_{i=1}^{3} a_i^\dagger n_i \tag{74}$$

and $$\mu^- = \mu \sum_{i=1}^{3} a_i n_i \tag{75}$$

Using Eqs. (69) though (71) one obtains $$\mu^- = \mu\left[\left(a_1 - \frac{1}{2}a_2 - \frac{1}{2}a_3\right)i + \frac{\sqrt{3}}{2}(a_2 - a_3)j\right]. \tag{76}$$

From Eqs. (17) though (19) one has $$a_1 - \frac{1}{2}a_2 - \frac{1}{2}a_3 = \frac{\sqrt{3}}{2}(b_{2\pi/3} + b_{-2\pi/3}) \tag{77}$$

and $$a_2 - a_3 = i(b_{2\pi/3} - b_{-2\pi/3}). \tag{78}$$

Hence $$\mu^- = \frac{\sqrt{3}}{2}\mu[(i + ij)b_{2\pi/3} + (i - ij)b_{-2\pi/3}]. \tag{79}$$

6 Aggregate in Arbitrary Orientation
6.1 Rotation Around the z-Axis

Here we consider the case where the aggregate is rotated about the z-axis by an angle. One has $$i = \cos(\omega)i' + \sin(\omega)j' \tag{80}$$

$$j = -\sin(\psi)i' + \cos(\psi)j'. \tag{81}$$

On then has $$i - ij = e^{i\psi(i'-ij')} \tag{82}$$

$$i + ij = e^{-i\psi(i'+ij')}. \tag{83}$$

Equation (79) now becomes $$\mu^- = \frac{\sqrt{3}}{2}\mu e^{-i\psi}(i' + ij')b_{2\pi/3} + \frac{\sqrt{3}}{2}\mu e^{i\psi}(i' - ij')b_{-2\pi/3}. \tag{84}$$

6.2 Transforming to a New z-Axis

We now rotate about the y-axis by an angle θ

$$i' = \cos(\theta)i'' - \sin(\theta)k'' \tag{85}$$

$$j' = j'' \tag{86}$$

$$k' = \sin(\theta)i'' + \cos(\theta)k''. \tag{87}$$

Rotating about the k" axis by θ yields $$i'' = \cos(\phi)i''' + \sin(\phi)j''' \tag{88}$$

$$j'' = -\sin(\phi)i''' + \cos(\phi)j''' \tag{89}$$

$$k'' = k'''. \tag{90}$$

The overall transformation is thus $$i' = \cos(\theta)\cos(\phi)i''' + \cos(\theta)\sin(\phi)j''' - \sin(\theta)k''' \tag{91}$$

$$j' = -\sin(\phi)i''' + \cos(\phi)j''' \tag{92}$$

$$k' = \sin(\theta)\cos(\phi)i''' + \sin(\theta)\sin(\phi)j''' + \cos(\theta)k'''. \tag{93}$$

One can show that if $$i''' \times j''' = k''', \tag{94}$$

then $$i' \times j' = k'. \tag{95}$$

This provides a consistency check.
One now has $$i' - ij' = [\cos(\theta)\cos(\phi) + i\sin(\theta)]i''' + [\cos(\theta)\sin(\phi) - i\cos(\phi)]j''' - \sin(\theta)k''' \tag{96}$$

and $$i' + ij' = [\cos(\theta)\cos(\phi) - i\sin(\phi)]i''' + [\cos(\theta)\sin(\phi) + i\cos(\phi)]j''' - \sin(\theta)k''' \tag{97}$$

These last two equations yield $$i' - ij' = \tag{98}$$

$$\frac{1}{2}e^{i\phi}[1 + \cos(\theta)](i''' - ij''') - \frac{1}{2}e^{i\phi}[1 - \cos(\theta)](i''' + ij''') - \sin(\theta)k'''$$

$$i' + ij' = \tag{99}$$

$$-\frac{1}{2}e^{i\phi}[1 - \cos(\theta)](i''' - ij''') + \frac{1}{2}e^{-i\phi}[1 + \cos(\theta)](i''' + ij''') - \sin(\theta)k'''$$

Substituting Eqs. (98) and (99) yields $$\mu^- = \frac{\sqrt{3}}{4}\mu e^{-i\psi}e^{-i\phi}[1+\cos(\theta)](i'''+ij''')b_{2\pi/3} - \qquad(100)$$
$$\frac{\sqrt{3}}{4}\mu e^{-i\psi}e^{i\phi}[1-\cos(\theta)](i'''-ij''')b_{2\pi/3} - \frac{\sqrt{3}}{2}\mu e^{-i\psi}\sin(\theta)k'''b_{2\pi/3} -$$
$$\frac{\sqrt{3}}{4}\mu e^{i\psi}e^{i\phi}[1+\cos(\theta)](i'''-ij''')b_{-2\pi/3} - \frac{\sqrt{3}}{2}\mu e^{i\psi}\sin(\theta)k'''b_{-2\pi/3}.$$

We now have the aggregate dipole moment for any orientation of the aggregate.

To keep the notation simple, we now relabel the coordinate systems so that the triple prime system, which is the lab system, will be the unprimed system, that is Eq. (100) becomes $$\mu^- = \frac{\sqrt{3}}{4}\mu e^{-i\psi}e^{-i\phi}[1+\cos(\theta)](i+ij)b_{2\pi/3} - \qquad(101)$$
$$\frac{\sqrt{3}}{4}\mu e^{-i\psi}e^{i\phi}[1-\cos(\theta)](i-ij)b_{2\pi/3} - \frac{\sqrt{3}}{2}\mu e^{-i\psi}\sin(\theta)kb_{2\pi/3} -$$
$$\frac{\sqrt{3}}{4}\mu e^{i\psi}e^{i\phi}[1+\cos(\theta)](i-ij)b_{-2\pi/3} - \frac{\sqrt{3}}{2}\mu e^{i\psi}\sin(\theta)kb_{-2\pi/3}.$$

where now i, j, and k are the unit vectors for the lab coordinate system.

7 Circularly Polarized Light

We now consider a circularly polarized plane wave propagating along the z-axis. For right-hand circular polarization the electric field has the form $$E_R = E_0[i\cos(kz-\omega_0 t+\delta) + j\sin(kz-i\omega_0 t+\delta)]. \qquad(102)$$

Similarly, for left-hand circular polarization the electric filed has the form $$E_L = E_0[i\cos(kz-\omega_0 t+\delta) - j\sin(kz-i\omega_0 t+\delta)]. \qquad(103)$$

Here $\omega_0$ is the optical frequency, $\delta$ is a phase shift, $E_0$ is the electric field strength, and $$k = \frac{2\pi}{\lambda} \qquad(104)$$

where $\lambda$ is the wavelength of light. Equations (102) and (103) can be written as $$E_R = \frac{1}{2}E_0 e^{i\delta}(i-ij)e^{i(kz-\omega_0 t)} + \frac{1}{2}E_0 e^{-i\delta}(i+ij)e^{-i(kz-\omega_0 t)} \qquad(105)$$

and $$E_L = \frac{1}{2}E_0 e^{i\delta}(i+ij)e^{i(kz-\omega_0 t)} + \frac{1}{2}E_0 e^{-i\delta}(i-ij)e^{-i(kz-\omega_0 t)}. \qquad(106)$$

Using Glauber's convention for the positive and negative frequency components of the electromagnetic filed, one has $$E_R^{(+)} = \frac{1}{2}E_0 e^{i\delta}(i-ij)e^{i(kz-\omega_0 t)}, \qquad(107)$$

$$E_R^{(-)} = \frac{1}{2}E_0 e^{-i\delta}(i+ij)e^{-i(kz-\omega_0 t)}, \qquad(108)$$

-continued $$E_L^{(+)} = \frac{1}{2}E_0 e^{i\delta}(i+ij)e^{i(kz-\omega_0 t)}, \qquad(109)$$

and $$E_L^{(-)} = \frac{1}{2}E_0 e^{-i\delta}(i-ij)e^{-i(kz-\omega_0 t)}. \qquad(110)$$

We consider the case when the wavelength of light is long compared to the size of the aggregate and we consider the case when the aggregate is located at the origin. In this case, the Hamiltonian for the interaction of the aggregate with right-hand circularly polarized light is $$H_R = \mu^+ \cdot E_R^{(+)} + \mu^- \cdot E_R^{(-)} \qquad(111)$$

The Hamiltonian for the interaction of the aggregate with left-hand circularly polarized light is $$H_L = \mu^+ \cdot E_L^{(+)} + \mu^- \cdot E_L^{(-)} \qquad(112)$$

We now note that $$(i-ij)\cdot(i-ij) = (i+ij)\cdot(i+ij) = 0 \qquad(113)$$

and $$(i+ij)\cdot(i-ij) = 2. \qquad(114)$$

Using Eq. (101) one now obtains $$\mu^- \cdot E_R^{(-)} = -\frac{\sqrt{3}}{4}\mu E_0 e^{-i\psi}e^{i\phi}e^{-i\delta}e^{i\omega_0 t}[1-\cos(\theta)]b_{2\pi/3} + \qquad(115)$$
$$\frac{\sqrt{3}}{4}\mu E_0 e^{i\psi}e^{i\phi}e^{-i\delta}e^{i\omega_0 t}[1+\cos(\theta)]b_{-2\pi/3} \text{ and}$$

$$\mu^- \cdot E_L^{(-)} = \frac{\sqrt{3}}{4}\mu E_0 e^{-i\psi}e^{-i\phi}e^{-i\delta}e^{i\omega_0 t}[1+\cos(\theta)]b_{2\pi/3} - \qquad(116)$$
$$\frac{\sqrt{3}}{4}\mu E_0 e^{i\psi}e^{-i\phi}e^{-i\delta}e^{i\omega_0 t}[1-\cos(\theta)]b_{-2\pi/3}.$$

The Hermitian conjugates of these two equations are $$\mu^+ \cdot E_R^{(+)} = -\frac{\sqrt{3}}{4}\mu E_0 e^{i\psi}e^{-i\phi}e^{i\delta}e^{-i\omega_0 t}[1-\cos(\theta)]b_{2\pi/3}^\dagger + \qquad(117)$$
$$\frac{\sqrt{3}}{4}\mu E_0 e^{-i\psi}e^{-i\phi}e^{i\delta}e^{-i\omega_0 t}[1+\cos(\theta)]b_{-2\pi/3}^\dagger \text{ and}$$

$$\mu^+ \cdot E_L^{(+)} = \frac{\sqrt{3}}{4}\mu E_0 e^{i\psi}e^{i\phi}e^{i\delta}e^{-i\omega_0 t}[1+\cos(\theta)]b_{2\pi/3}^\dagger - \qquad(118)$$
$$\frac{\sqrt{3}}{4}\mu E_0 e^{-i\psi}e^{i\phi}e^{i\delta}e^{-i\omega_0 t}[1-\cos(\theta)]b_{-2\pi/3}^\dagger.$$

8 Transitions Amplitudes Between the Ground State and the One Exciton States

One has $$\langle 1;0|b_{2\pi/3}|0\rangle = 0 \qquad(119)$$

$$\langle 1;2\pi/3|b_{2\pi/3}^\dagger|0\rangle = 1 \qquad(120)$$

$$\langle 1;-2\pi/3|b_{2\pi/3}^\dagger|0\rangle = 0 \qquad(121)$$

and $$\langle 1;0|b_{-2\pi/3}^\dagger|0\rangle = 0 \qquad(122)$$

$$\langle 1;2\pi/3|b_{-2\pi/3}^\dagger|0\rangle = 0 \qquad(123)$$

$$\langle 1;-2\pi/3|b_{-2\pi/3}^\dagger|0\rangle = 1 \qquad(124)$$

9 Two Exciton State Vectors Evaluated

Consider Eq. (50) and (51) we have the following eigenvalue eigenvector pairs:

$$E_{2S;+} = 2E_0 + J + \frac{\Delta+K}{2} + \frac{1}{2}\sqrt{(2J+K-\Delta)^2 + 32J^2} \quad (125)$$

$$|2S;+\rangle = N\{4\sqrt{2}J|2Sa\rangle + [2J+K-\Delta+\sqrt{(2J+K-\Delta)^2+32J^2}]|2Sb\rangle\} \text{ and} \quad (126)$$

$$E_{2S;-} = 2E_0 + J + \frac{\Delta+K}{2} - \frac{1}{2}\sqrt{(2J+K-\Delta)^2 + 32J^2} \quad (127)$$

$$|2S;-\rangle = N_S\{-[2J+K-\Delta+\sqrt{(2J+K-\Delta)^2+32J^2}]|2Sa\rangle + 4\sqrt{2}J|2Sb\rangle\}. \quad (128)$$

Let $$\alpha_{2S} = 4\sqrt{2}N_S J \quad (129)$$

and $$\beta_{2S} = N_S[2J+K-\Delta+\sqrt{(2J+K-\Delta)^2+32J^2}] \quad (130)$$

then $$|2S;+\rangle = \alpha_{2S}|2Sa\rangle + \beta_{2S}|2Sb\rangle \quad (131)$$

and $$|2S;-\rangle = -\beta_{2S}|2Sa\rangle + \alpha_{2S}|2Sb\rangle. \quad (132)$$

Now from Eqs. (57) and (58) we have $$E_{2+;+} = 2E_0 + \frac{-J+K+\Delta}{2} + \frac{1}{2}\sqrt{(-J+K-\Delta)^2 + 8J^2} \quad (133)$$

$$|2+;+\rangle = N_+\{[J-K+\Delta+\sqrt{(-J+K-\Delta)^2+8J^2}]|2a+\rangle + 2\sqrt{2}J(1+e^{-i2\pi/3})|2b+\rangle\} \text{ and} \quad (134)$$

$$E_{2+;-} = 2E_0 + \frac{-J+K+\Delta}{2} - \frac{1}{2}\sqrt{(-J+K-\Delta)^2 + 8J^2} \quad (135)$$

$$|2+;-\rangle = N_+\{-2\sqrt{2}J(1+e^{-i2\pi/3})|2a+\rangle + [J-K+\Delta+\sqrt{(-J+K-\Delta)^2+8J^2}]|2b+\rangle\} \quad (136)$$

Let $$\alpha_{2+} N_+[J-K+\Delta+\sqrt{(-J+K-\Delta)^2+8J^2}] \quad (137)$$

and $$\beta_{2+} = N_+ 2\sqrt{2}J(1+e^{-i2\pi/3}), \quad (138)$$

then $$|2+;-\rangle = \alpha_{2+}|2a+\rangle + \beta_{2+}|2b+\rangle \quad (139)$$

and $$|2+;-\rangle = -\beta_{2+}|2a+\rangle + \alpha_{2+}|2b+\rangle. \quad (140)$$

From Eqs. (64) and (5) we have $$E_{2-;+} = 2E_0 + \frac{-J+\Delta+K}{2} + \frac{1}{2}\sqrt{(-J+K-\Delta)^2 + 8J^2} \quad (141)$$

$$|2-;+\rangle = N_2 - \{[J-K+\Delta+\sqrt{(-J+K-\Delta)^2+8J^2}]|2a-\rangle + 2\sqrt{2}J(1+e^{i2\pi/3})|2b-\rangle\} \text{ and} \quad (142)$$

$$E_{2-;-} = 2E_0 + \frac{-J+\Delta+K}{2} - \frac{1}{2}\sqrt{(-J+K-\Delta)^2 + 8J^2} \quad (143)$$

$$|2-;-\rangle = N_-\{-2\sqrt{2}J(1+e^{i2\pi/3})|2a-\rangle + [J-K+\Delta+\sqrt{(-J+K-\Delta)^2+8J^2}]|2b-\rangle\} \quad (144)$$

Introducing $$\alpha_{2-} = N_-[J-K+\Delta+\sqrt{(-J+K-\Delta)^2+8J^2}] \quad (145)$$

and $$\beta_{2-} = N_- 2\sqrt{2}J(1+e^{i2\pi/3}), \quad (146)$$

one has $$|2-;+\rangle = \alpha_{2-}|2a-\rangle + \beta_{2-}|2b-\rangle \quad (147)$$

and $$|2-;-\rangle = -\beta_{2-}|2a-\rangle + \alpha_{2-}|2b-\rangle. \quad (148)$$

We note that $$E_{2+;+} = E_{2-;+} \quad (149)$$

$$E_{2+;-} = E_{2-;-} \quad (150)$$

$$N_+ = N_- \quad (151)$$

$$\alpha_{2+} = \alpha_{2-} \quad (152)$$

$$\beta_{2+} = \beta_{2-} \quad (153)$$

One also has $$N_+^2 = N_-^2 = [J-K+\Delta+\sqrt{(-J+K-\Delta)^2+8J^2}]^2 + 8J^2 \quad (154)$$

10 Transition Amplitudes to the Two-Exciton States Form the One Exciton States We have $$b^\dagger_{2\pi/3}|1;0\rangle = \sqrt{\frac{2}{3}}|2a+\rangle + \frac{1}{\sqrt{3}}(1+e^{i2\pi/3})|2b+\rangle \quad (155)$$

$$\langle 2Sa|b^\dagger_{2\pi/3}|1;0\rangle = 0 \quad (156)$$

$$\langle 2Sb|b^\dagger_{2\pi/3}|1;0\rangle = 0 \quad (157)$$

$$\langle 2a+|b^\dagger_{2\pi/3}|1;0\rangle = 0 \quad (158)$$

$$\langle 2b+|b^\dagger_{2\pi/3}|1;0\rangle = 0 \quad (159)$$

$$\langle 2a-|b^\dagger_{2\pi/3}|1;0\rangle = \sqrt{\frac{2}{3}} \quad (160)$$

$$\langle 2b-|b^\dagger_{2\pi/3}|1;0\rangle = \frac{1}{\sqrt{3}}(1+e^{i2\pi/3}) \quad (161)$$

$$b^\dagger_{-2\pi/3}|1;0\rangle = \sqrt{\frac{2}{3}}|2a-\rangle + \frac{1}{\sqrt{3}}(1+e^{-i2\pi/3})|2b-\rangle \quad (162)$$

$$\langle 2Sa|b^\dagger_{-2\pi/3}|1;0\rangle = 0 \quad (163)$$

$$\langle 2Sb|b^\dagger_{-2\pi/3}|1;0\rangle = 0 \quad (164)$$

-continued $$\langle 2a+|b^\dagger_{-2\pi/3}|1;0\rangle = \sqrt{\frac{2}{3}}$$ (165)

$$\langle 2b+|b^\dagger_{-2\pi/3}|1;0\rangle = \frac{1}{\sqrt{3}}(1+e^{-i2\pi/3})$$ (166)

$$\langle 2a-|b^\dagger_{-2\pi/3}|1;0\rangle = 0$$ (167)

$$\langle 2b-|b^\dagger_{-2\pi/3}|1;0\rangle = 0.$$ (168)

We also have $$b^\dagger_{2\pi/3}|1;2\pi/3\rangle = \sqrt{\frac{2}{3}}|2a-\rangle + \frac{2}{\sqrt{3}}e^{i2\pi/3}|2b-\rangle$$ (169)

$$\langle 2Sa|b^\dagger_{2\pi/3}|1;2\pi/3\rangle = 0$$ (170)

$$\langle 2Sb|b^\dagger_{2\pi/3}|1;2\pi/3\rangle = 0$$ (171)

$$\langle 2a+|b^\dagger_{2\pi/3}|1;2\pi/3\rangle = 0$$ (172)

$$\langle 2b+|b^\dagger_{2\pi/3}|1;2\pi/3\rangle = 0$$ (173)

$$\langle 2a-|b^\dagger_{2\pi/3}|1;2\pi/3\rangle = \sqrt{\frac{2}{3}}$$ (174)

$$\langle 2b-|b^\dagger_{2\pi/3}|1;2\pi/3\rangle = \frac{2}{\sqrt{3}}e^{i2\pi/3}$$ (175)

$$b^\dagger_{-2\pi/3}|1;2\pi/3\rangle = \sqrt{\frac{2}{3}}|2Sa\rangle - \frac{1}{\sqrt{3}}|2Sb\rangle$$ (176)

$$\langle 2Sa|b^\dagger_{-2\pi/3}|1;2\pi/3\rangle = \sqrt{\frac{2}{3}}$$ (177)

$$\langle 2Sb|b^\dagger_{-2\pi/3}|1;2\pi/3\rangle = -\frac{1}{\sqrt{3}}$$ (178)

$$\langle 2a+|b^\dagger_{-2\pi/3}|1;2\pi/3\rangle = 0$$ (179)

$$\langle 2b+|b^\dagger_{-2\pi/3}|1;2\pi/3\rangle = 0$$ (180)

$$\langle 2a-|b^\dagger_{-2\pi/3}|1;2\pi/3\rangle = 0$$ (181)

$$\langle 2b-|b^\dagger_{-2\pi/3}|1;2\pi/3\rangle = 0.$$ (182)

We also have $$b^\dagger_{2\pi/3}|1;-2\pi/3\rangle = \sqrt{\frac{2}{3}}|2Sa\rangle - \frac{1}{\sqrt{3}}|2Sb\rangle$$ (183)

$$\langle 2Sa|b^\dagger_{2\pi/3}|1;-2\pi/3\rangle = \sqrt{\frac{2}{3}}$$ (184)

$$\langle 2Sb|b^\dagger_{2\pi/3}|1;-2\pi/3\rangle = -\frac{1}{\sqrt{3}}$$ (185)

$$\langle 2a+|b^\dagger_{2\pi/3}|1;-2\pi/3\rangle = 0$$ (186)

$$\langle 2b+|b^\dagger_{2\pi/3}|1;-2\pi/3\rangle = 0$$ (187)

$$\langle 2a-|b^\dagger_{2\pi/3}|1;-2\pi/3\rangle = 0$$ (188)

$$\langle 2b-|b^\dagger_{2\pi/3}|1;-2\pi/3\rangle = 0$$ (189)

$$b^\dagger_{-2\pi/3}|1;-2\pi/3\rangle = \sqrt{\frac{2}{3}}|2a+\rangle + \frac{2}{\sqrt{3}}e^{-i2\pi/3}|2b+\rangle$$ (190)

$$\langle 2Sa|b^\dagger_{-2\pi/3}|1;-2\pi/3\rangle = 0$$ (191)

$$\langle 2Sb|b^\dagger_{-2\pi/3}|1;-2\pi/3\rangle = 0$$ (192)

$$\langle 2a+|b^\dagger_{-2\pi/3}|1;-2\pi/3\rangle = \sqrt{\frac{2}{3}}$$ (193)

$$\langle 2b+|b^\dagger_{-2\pi/3}|1;-2\pi/3\rangle = \frac{2}{\sqrt{3}}e^{-i2\pi/3}$$ (194)

$$\langle 2a-|b^\dagger_{-2\pi/3}|1;-2\pi/3\rangle = 0$$ (195)

$$\langle 2b-|b^\dagger_{-2\pi/3}|1;-2\pi/3\rangle = 0.$$ (196)

10.1 Energy Eigenstate Matrix Elements $$\langle 2S;+|b^\dagger_{2\pi/3}|1;2\pi/3\rangle = 0$$ (197)

$$\langle 2S;-|b^\dagger_{2\pi/3}|1;2\pi/3\rangle = 0$$ (198)

$$\langle 2+;+|b^\dagger_{2\pi/3}|1;2\pi/3\rangle = 0$$ (199)

$$\langle 2+;-|b^\dagger_{2\pi/3}|1;2\pi/3\rangle = 0$$ (200)

$$\langle 2-;+|b^\dagger_{2\pi/3}|1;2\pi/3\rangle = \sqrt{\frac{2}{3}}\alpha^*_{2-} + \frac{2}{\sqrt{3}}e^{i2\pi/3}\beta^*_{2-}$$ (201)

$$\langle 2-;-|b^\dagger_{2\pi/3}|1;2\pi/3\rangle = -\sqrt{\frac{2}{3}}\beta^*_{2-} + \frac{2}{\sqrt{3}}e^{i2\pi/3}\alpha^*_{2-}$$ (202)

$$\langle 2S;+|b^\dagger_{2\pi/3}|1;-2\pi/3\rangle = \sqrt{\frac{2}{3}}\alpha^*_{2S} - \frac{1}{\sqrt{3}}\beta^*_{2S}$$ (203)

$$\langle 2S;-|b^\dagger_{2\pi/3}|1;-2\pi/3\rangle = -\sqrt{\frac{2}{3}}\beta^*_{2S} - \frac{1}{\sqrt{3}}\alpha^*_{2S}$$ (204)

$$\langle 2+;+|b^\dagger_{2\pi/3}|1;-2\pi/3\rangle = 0$$ (205)

$$\langle 2+;-|b^\dagger_{2\pi/3}|1;-2\pi/3\rangle = 0$$ (206)

$$\langle 2-;+|b^\dagger_{2\pi/3}|1;-2\pi/3\rangle = 0$$ (207)

$$\langle 2-;-|b^\dagger_{2\pi/3}|1;-2\pi/3\rangle = 0$$ (208)

$$\langle 2S;+|b^\dagger_{-2\pi/3}|1;2\pi/3\rangle = \sqrt{\frac{2}{3}}\alpha^*_{2S} - \frac{1}{\sqrt{3}}\beta^*_{2S}$$ (209)

$$\langle 2S;-|b^\dagger_{-2\pi/3}|1;2\pi/3\rangle = -\sqrt{\frac{2}{3}}\beta^*_{2S} - \frac{1}{\sqrt{3}}\alpha^*_{2S}$$ (210)

$$\langle 2+;+|b^\dagger_{-2\pi/3}|1;2\pi/3\rangle = 0$$ (211)

$$\langle 2+;-|b^\dagger_{-2\pi/3}|1;2\pi/3\rangle = 0$$ (212)

$$\langle 2-;+|b^\dagger_{-2\pi/3}|1;2\pi/3\rangle = 0$$ (213)

$$\langle 2-;-|b^\dagger_{-2\pi/3}|1;2\pi/3\rangle = 0$$ (214)

$$\langle 2S;+|b^\dagger_{-2\pi/3}|1;-2\pi/3\rangle = 0$$ (215)

$$\langle 2S;-|b^\dagger_{-2\pi/3}|1;-2\pi/3\rangle = 0$$ (216)

$$\langle 2+;+|b^\dagger_{-2\pi/3}|1;-2\pi/3\rangle = \sqrt{\frac{2}{3}}\alpha^*_{2+} + \frac{2}{\sqrt{3}}e^{-i2\pi/3}\beta^*_{2+}$$ (217)

$$\langle 2+;-|b^\dagger_{-2\pi/3}|1;-2\pi/3\rangle = -\sqrt{\frac{2}{3}}\beta^*_{2+} + \frac{2}{\sqrt{3}}e^{-i2\pi/3}\alpha^*_{2+}$$ (218)

$$\langle 2-;+|b^\dagger_{-2\pi/3}|1;-2\pi/3\rangle = 0$$ (219)

$$\langle 2-;-|b^\dagger_{-2\pi/3}|1;-2\pi/3\rangle = 0$$ (220)

11 Circular Polarized Light Induced Transition Amplitudes $$\langle 2S; +|\mu^+ \cdot E_R^{(+)}|1; 2\pi/3\rangle = \tag{221}$$
$$\frac{\sqrt{3}}{4}\mu E_0 e^{-i\psi}e^{-i\phi}e^{i\delta}e^{-i\omega_0 t}[1+\cos(\theta)]\left(\sqrt{\frac{2}{3}}\alpha_{2S}^* - \frac{1}{\sqrt{3}}\beta_{2S}^*\right)$$

$$\langle 2S; -|\mu^+ \cdot E_R^{(+)}|1; 2\pi/3\rangle = \tag{222}$$
$$\frac{\sqrt{3}}{4}\mu E_0 e^{-i\psi}e^{-i\phi}e^{i\delta}e^{-i\omega_0 t}[1+\cos(\theta)]\left(-\sqrt{\frac{2}{3}}\beta_{2S}^* - \frac{1}{\sqrt{3}}\alpha_{2S}^*\right)$$

$$\langle 2+; +|\mu^+ \cdot E_R^{(+)}|1; 2\pi/3\rangle = 0 \tag{223}$$

$$\langle 2+; -|\mu^+ \cdot E_R^{(+)}|1; 2\pi/3\rangle = 0 \tag{224}$$

$$\langle 2-; +|\mu^+ \cdot E_R^{(+)}|1; 2\pi/3\rangle = \tag{225}$$
$$-\frac{\sqrt{3}}{4}\mu E_0 e^{i\psi}e^{-i\phi}e^{i\delta}e^{-i\omega_0 t}[1-\cos(\theta)]\left(\sqrt{\frac{2}{3}}\alpha_{2-}^* + \frac{2}{\sqrt{3}}e^{i2\pi/3}\beta_{2-}^*\right)$$

$$\langle 2-; -|\mu^+ \cdot E_R^{(+)}|1; 2\pi/3\rangle = \tag{226}$$
$$-\frac{\sqrt{3}}{4}\mu E_0 e^{i\psi}e^{-i\phi}e^{i\delta}e^{-i\omega_0 t}[1-\cos(\theta)]\left(-\sqrt{\frac{2}{3}}\beta_{2-}^* + \frac{2}{\sqrt{3}}e^{i2\pi/3}\alpha_{2-}^\dagger\right)$$

$$\langle 2S; +|\mu^+ \cdot E_L^{(+)}|1; 2\pi/3\rangle = \tag{227}$$
$$-\frac{\sqrt{3}}{4}\mu E_0 e^{-i\psi}e^{i\phi}e^{i\delta}e^{-i\omega_0 t}[1-\cos(\theta)]\left(\sqrt{\frac{2}{3}}\alpha_{2S}^* - \frac{1}{\sqrt{3}}\beta_{2S}^*\right)$$

$$\langle 2S; -|\mu^+ \cdot E_L^{(+)}|1; 2\pi/3\rangle = \tag{228}$$
$$-\frac{\sqrt{3}}{4}\mu E_0 e^{-i\psi}e^{i\phi}e^{i\delta}e^{-i\omega_0 t}[1-\cos(\theta)]\left(-\sqrt{\frac{2}{3}}\beta_{2S}^* - \frac{1}{\sqrt{3}}\alpha_{2S}^*\right)$$

$$\langle 2+; +|\mu^+ \cdot E_L^{(+)}|1; 2\pi/3\rangle = 0 \tag{229}$$

$$\langle 2+; -|\mu^+ \cdot E_L^{(+)}|1; 2\pi/3\rangle = 0 \tag{230}$$

$$\langle 2-; +|\mu^+ \cdot E_L^{(+)}|1; 2\pi/3\rangle = \tag{231}$$
$$\frac{\sqrt{3}}{4}\mu E_0 e^{i\psi}e^{i\phi}e^{i\delta}e^{-i\omega_0 t}[1+\cos(\theta)]\left(\sqrt{\frac{2}{3}}\alpha_{2-}^* + \frac{2}{\sqrt{3}}e^{i2\pi/3}\beta_{2-}^*\right)$$

$$\langle 2-; -|\mu^+ \cdot E_L^{(+)}|1; 2\pi/3\rangle = \tag{232}$$
$$\frac{\sqrt{3}}{4}\mu E_0 e^{i\psi}e^{i\phi}e^{i\delta}e^{-i\omega_0 t}[1+\cos(\theta)]\left(-\sqrt{\frac{2}{3}}\beta_{2-}^* + \frac{2}{\sqrt{3}}e^{i2\pi/3}\alpha_{2-}^*\right)$$

$$\langle 2S; +|\mu^+ \cdot E_R^{(+)}|1; -2\pi/3\rangle = \tag{233}$$
$$-\frac{\sqrt{3}}{4}\mu E_0 e^{i\psi}e^{-i\phi}e^{i\delta}e^{-i\omega_0 t}[1-\cos(\theta)]\left(\sqrt{\frac{2}{3}}\alpha_{2S}^* - \frac{1}{\sqrt{3}}\beta_{2S}^*\right)$$

$$\langle 2S; -|\mu^+ \cdot E_R^{(+)}|1; -2\pi/3\rangle = \tag{234}$$
$$-\frac{\sqrt{3}}{4}\mu E_0 e^{i\psi}e^{-i\phi}e^{i\delta}e^{-i\omega_0 t}[1-\cos(\theta)]\left(-\sqrt{\frac{2}{3}}\beta_{2S}^* - \frac{1}{\sqrt{3}}\alpha_{2S}^*\right)$$

$$\langle 2+; +|\mu^+ \cdot E_R^{(+)}|1; -2\pi/3\rangle = \tag{235}$$
$$\frac{\sqrt{3}}{4}\mu E_0 e^{-i\psi}e^{-i\phi}e^{i\delta}e^{-i\omega_0 t}[1+\cos(\theta)]\left(\sqrt{\frac{2}{3}}\alpha_{2+}^* + \frac{2}{\sqrt{3}}e^{-i2\pi/3}\beta_{2+}^*\right)$$

$$\langle 2+; -|\mu^+ \cdot E_R^{(+)}|1; -2\pi/3\rangle = \tag{236}$$
$$\frac{\sqrt{3}}{4}\mu E_0 e^{-i\psi}e^{-i\phi}e^{i\delta}e^{-i\omega_0 t}[1+\cos(\theta)]\left(-\sqrt{\frac{2}{3}}\beta_{2S}^* + \frac{2}{\sqrt{3}}e^{-i2\pi/3}\alpha_{2+}^*\right)$$

$$\langle 2-; +|\mu^+ \cdot E_R^{(+)}|1; -2\pi/3\rangle = 0 \tag{237}$$

$$\langle 2-; -|\mu^+ \cdot E_R^{(+)}|1; -2\pi/3\rangle = 0 \tag{238}$$

$$\langle 2S; +|\mu^+ \cdot E_L^{(+)}|1; -2\pi/3\rangle = \tag{239}$$
$$\frac{\sqrt{3}}{4}\mu E_0 e^{i\psi}e^{i\phi}e^{i\delta}e^{-i\omega_0 t}[1+\cos(\theta)]\left(\sqrt{\frac{2}{3}}\alpha_{2S}^* - \frac{1}{\sqrt{3}}\beta_{2S}^*\right)$$

$$\langle 2S; -|\mu^+ \cdot E_L^{(+)}|1; -2\pi/3\rangle = \tag{240}$$
$$\frac{\sqrt{3}}{4}\mu E_0 e^{i\psi}e^{i\phi}e^{i\delta}e^{-i\omega_0 t}[1+\cos(\theta)]\left(-\sqrt{\frac{2}{3}}\beta_{2S}^* - \frac{1}{\sqrt{3}}\alpha_{2S}^*\right)$$

$$\langle 2+; +|\mu^+ \cdot E_L^{(+)}|1; -2\pi/3\rangle = \tag{241}$$
$$-\frac{\sqrt{3}}{4}\mu E_0 e^{-i\psi}e^{i\phi}e^{i\delta}e^{-i\omega_0 t}[1-\cos(\theta)]\left(\sqrt{\frac{2}{3}}\alpha_{2+}^* + \frac{2}{\sqrt{3}}e^{-i2\pi/3}\beta_{2+}^*\right)$$

$$\langle 2+; -|\mu^+ \cdot E_L^{(+)}|1; -2\pi/3\rangle = \tag{242}$$
$$-\frac{\sqrt{3}}{4}\mu E_0 e^{-i\psi}e^{i\phi}e^{i\delta}e^{-i\omega_0 t}[1-\cos(\theta)]\left(-\sqrt{\frac{2}{3}}\beta_{2+}^* + \frac{2}{\sqrt{3}}e^{-i2\pi/3}\alpha_{2+}^*\right)$$

$$\langle 2-; +|\mu^+ \cdot E_L^{(+)}|1; -2\pi/3\rangle = 0 \tag{243}$$

$$\langle 2-; -|\mu^+ \cdot E_L^{(+)}|1; -2\pi/3\rangle = 0 \tag{244}$$

12 Norm Squared Transition Amplitudes $$|\langle 2S; +|\mu^+ \cdot E_R^{(+)}|1; 2\pi/3\rangle|^2 = \tag{245}$$
$$\frac{3}{16}\mu^2 E_0^2 [1+\cos(\theta)]^2 \left|\sqrt{\frac{2}{3}}\alpha_{2S}^* - \frac{1}{\sqrt{3}}\beta_{2S}^*\right|^2$$

$$|\langle 2S; -|\mu^+ \cdot E_R^{(+)}|1; 2\pi/3\rangle|^2 = \tag{246}$$
$$\frac{3}{16}\mu^2 E_0^2 [1+\cos(\theta)]^2 \left|-\sqrt{\frac{2}{3}}\beta_{2S}^* - \frac{1}{\sqrt{3}}\alpha_{2S}^*\right|^2$$

$$|\langle 2+; +|\mu^+ \cdot E_R^{(+)}|1; 2\pi/3\rangle|^2 = 0 \tag{247}$$

$$|\langle 2+; -|\mu^+ \cdot E_R^{(+)}|1; 2\pi/3\rangle|^2 = 0 \tag{248}$$

$$|\langle 2-; +|\mu^+ \cdot E_R^{(+)}|1; 2\pi/3\rangle|^2 = \tag{249}$$
$$\frac{3}{16}\mu^2 E_0^2 [1-\cos(\theta)]^2 \left|\sqrt{\frac{2}{3}}\alpha_{2-}^* + \frac{1}{\sqrt{3}}e^{i2\pi/3}\beta_{2-}^*\right|^2$$

$$|\langle 2-; -|\mu^+ \cdot E_R^{(+)}|1; 2\pi/3\rangle|^2 = \tag{250}$$
$$\frac{3}{16}\mu^2 E_0^2 [1-\cos(\theta)]^2 \left|-\sqrt{\frac{2}{3}}\beta_{2-}^* + \frac{1}{\sqrt{3}}e^{i2\pi/3}\alpha_{2-}^\dagger\right|^2$$

$$|\langle 2S; +|\mu^+ \cdot E_L^{(+)}|1; 2\pi/3\rangle|^2 = \tag{251}$$

-continued $$\frac{3}{16}\mu^2 E_0^2[1-\cos(\theta)]^2\left|\sqrt{\frac{2}{3}}\alpha_{2S}^* - \frac{1}{\sqrt{3}}\beta_{2S}^*\right|^2$$

$$|\langle 2S; -|\mu^+ \cdot E_L^{(+)}|1; 2\pi/3\rangle|^2 = \tag{252}$$

$$\frac{3}{16}\mu^2 E_0^2[1-\cos(\theta)]^2\left|-\sqrt{\frac{2}{3}}\beta_{2S}^* - \frac{1}{\sqrt{3}}\alpha_{2S}^*\right|^2$$

$$|\langle 2+; +|\mu^+ \cdot E_L^{(+)}|1; 2\pi/3\rangle|^2 = 0 \tag{253}$$

$$|\langle 2+; -|\mu^+ \cdot E_L^{(+)}|1; 2\pi/3\rangle|^2 = 0 \tag{254}$$

$$|\langle 2-; +|\mu^+ \cdot E_L^{(+)}|1; 2\pi/3\rangle|^2 = \tag{255}$$

$$\frac{3}{16}\mu^2 E_0^2[1+\cos(\theta)]^2\left|\sqrt{\frac{2}{3}}\alpha_{2-}^* + \frac{2}{\sqrt{3}}e^{i2\pi/3}\beta_{2-}^*\right|^2$$

$$|\langle 2-; -|\mu^+ \cdot E_L^{(+)}|1; 2\pi/3\rangle|^2 = \tag{256}$$

$$\frac{3}{16}\mu^2 E_0^2[1+\cos(\theta)]^2\left|-\sqrt{\frac{2}{3}}\beta_{2-}^* + \frac{2}{\sqrt{3}}e^{i2\pi/3}\alpha_{2-}^*\right|^2$$

$$|\langle 2S; +|\mu^+ \cdot E_R^{(+)}|1; -2\pi/3\rangle|^2 = \tag{257}$$

$$\frac{3}{16}\mu^2 E_0^2[1-\cos(\theta)]^2\left|\sqrt{\frac{2}{3}}\alpha_{2S}^* - \frac{1}{\sqrt{3}}\beta_{2S}^*\right|^2$$

$$|\langle 2S; -|\mu^+ \cdot E_R^{(+)}|1; -2\pi/3\rangle|^2 = \tag{258}$$

$$\frac{3}{16}\mu^2 E_0^2[1-\cos(\theta)]^2\left|-\sqrt{\frac{2}{3}}\beta_{2S}^* - \frac{1}{\sqrt{3}}\alpha_{2S}^*\right|^2$$

$$|\langle 2+; +|\mu^+ \cdot E_R^{(+)}|1; -2\pi/3\rangle|^2 = \tag{259}$$

$$\frac{3}{16}\mu^2 E_0^2[1+\cos(\theta)]^2\left|\sqrt{\frac{2}{3}}\alpha_{2+}^* + \frac{2}{\sqrt{3}}e^{-i2\pi/3}\beta_{2+}^*\right|^2$$

$$|\langle 2+; -|\mu^+ \cdot E_R^{(+)}|1; -2\pi/3\rangle|^2 = \tag{260}$$

$$\frac{3}{16}\mu^2 E_0^2[1+\cos(\theta)]^2\left|-\sqrt{\frac{2}{3}}\beta_{2S}^* + \frac{2}{\sqrt{3}}e^{-i2\pi/3}\alpha_{2+}^*\right|^2$$

$$|\langle 2-; +|\mu^+ \cdot E_R^{(+)}|1; -2\pi/3\rangle|^2 = 0 \tag{261}$$

$$|\langle 2-; -|\mu^+ \cdot E_R^{(+)}|1; -2\pi/3\rangle|^2 = 0 \tag{262}$$

$$|\langle 2S; +|\mu^+ \cdot E_L^{(+)}|1; -2\pi/3\rangle|^2 = \tag{263}$$

$$\frac{3}{16}\mu^2 E_0^2[1+\cos(\theta)]^2\left|\sqrt{\frac{2}{3}}\alpha_{2S}^* - \frac{1}{\sqrt{3}}\beta_{2S}^*\right|^2$$

$$|\langle 2S; -|\mu^+ \cdot E_L^{(+)}|1; -2\pi/3\rangle|^2 = \tag{264}$$

$$\frac{3}{16}\mu^2 E_0^2[1+\cos(\theta)]^2\left|-\sqrt{\frac{2}{3}}\beta_{2S}^* - \frac{1}{\sqrt{3}}\alpha_{2S}^*\right|^2$$

$$|\langle 2+; +|\mu^+ \cdot E_L^{(+)}|1; -2\pi/3\rangle|^2 = \tag{265}$$

$$\frac{3}{16}\mu^2 E_0^2[1-\cos(\theta)]^2\left|\sqrt{\frac{2}{3}}\alpha_{2+}^* + \frac{2}{\sqrt{3}}e^{-i2\pi/3}\beta_{2+}^*\right|^2$$

$$|\langle 2+; -|\mu^+ \cdot E_L^{(+)}|1; -2\pi/3\rangle|^2 = \tag{266}$$

$$\frac{3}{16}\mu^2 E_0^2[1-\cos(\theta)]^2\left|-\sqrt{\frac{2}{3}}\beta_{2+}^* + \frac{2}{\sqrt{3}}e^{-i2\pi/3}\alpha_{2+}^*\right|^2$$

$$|\langle 2-; +|\mu^+ \cdot E_L^{(+)}|1; -2\pi/3\rangle|^2 = 0 \tag{267}$$

$$|\langle 2-; -|\mu^+ \cdot E_L^{(+)}|1; -2\pi/3\rangle|^2 = 0 \tag{268}$$

Note that the quantities Eq. (245) through (268) do not depend on the parameters, $\phi$, $\delta$, and $\omega_0 t$. Hence, for incoherent processes those parameters could be neglected or set to zero. Thus, the system response does not depend on how the molecule is rotated about its axis or about the lab z-axis or the phase of the incoming polarized light.

13 Special Case when the Plane of the Molecule is Perpendicular to the Direction of the Light Beam Here we consider the case when the plane of the molecule is perpendicular to the direction of the light beam (the lab z-axis), that is, $$\theta = 0. \tag{269}$$

One then has $$\cos(\theta) = 1. \tag{270}$$

Equations (245) though (268) then reduce to $$|\langle 2S; +|\mu^+ \cdot E_R^{(+)}|1; 2\pi/3\rangle|^2 = \frac{3}{4}\mu^2 E_0^2\left|\sqrt{\frac{2}{3}}\alpha_{2S}^* - \frac{1}{\sqrt{3}}\beta_{2S}^*\right|^2 \tag{271}$$

$$|\langle 2S; -|\mu^+ \cdot E_R^{(+)}|1; 2\pi/3\rangle|^2 = \frac{3}{4}\mu^2 E_0^2\left|-\sqrt{\frac{2}{3}}\beta_{2S}^* - \frac{1}{\sqrt{3}}\alpha_{2S}^*\right|^2 \tag{272}$$

$$|\langle 2+; +|\mu^+ \cdot E_R^{(+)}|1; 2\pi/3\rangle|^2 = 0 \tag{273}$$

$$|\langle 2+; -|\mu^+ \cdot E_R^{(+)}|1; 2\pi/3\rangle|^2 = 0 \tag{274}$$

$$|\langle 2-; +|\mu^+ \cdot E_R^{(+)}|1; 2\pi/3\rangle|^2 = 0 \tag{275}$$

$$|\langle 2-; -|\mu^+ \cdot E_R^{(+)}|1; 2\pi/3\rangle|^2 = 0 \tag{276}$$

$$|\langle 2S; +|\mu^+ \cdot E_L^{(+)}|1; 2\pi/3\rangle|^2 = 0 \tag{277}$$

$$|\langle 2S; -|\mu^+ \cdot E_L^{(+)}|1; 2\pi/3\rangle|^2 = 0 \tag{278}$$

$$|\langle 2+; +|\mu^+ \cdot E_L^{(+)}|1; 2\pi/3\rangle|^2 = 0 \tag{279}$$

$$|\langle 2+; -|\mu^+ \cdot E_L^{(+)}|1; 2\pi/3\rangle|^2 = 0 \tag{280}$$

$$|\langle 2-; +|\mu^+ \cdot E_L^{(+)}|1; 2\pi/3\rangle|^2 = \frac{3}{4}\mu^2 E_0^2\left|\sqrt{\frac{2}{3}}\alpha_{2-}^* + \frac{2}{\sqrt{3}}e^{i2\pi/3}\beta_{2-}^*\right|^2 \tag{281}$$

$$|\langle 2-; -|\mu^+ \cdot E_L^{(+)}|1; 2\pi/3\rangle|^2 = \frac{3}{4}\mu^2 E_0^2\left|-\sqrt{\frac{2}{3}}\beta_{2-}^* + \frac{2}{\sqrt{3}}e^{i2\pi/3}\alpha_{2-}^*\right|^2 \tag{282}$$

$$|\langle 2S; +|\mu^+ \cdot E_R^{(+)}|1; -2\pi/3\rangle|^2 = 0 \tag{283}$$

$$|\langle 2S; -|\mu^+ \cdot E_R^{(+)}|1; -2\pi/3\rangle|^2 = 0 \tag{284}$$

$$|\langle 2+; +|\mu^+ \cdot E_R^{(+)}|1; -2\pi/3\rangle|^2 = \frac{3}{4}\mu^2 E_0^2\left|\sqrt{\frac{2}{3}}\alpha_{2+}^* + \frac{2}{\sqrt{3}}e^{-i2\pi/3}\beta_{2+}^*\right|^2 \tag{285}$$

$$|\langle 2+; -|\mu^+ \cdot E_R^{(+)}|1; -2\pi/3\rangle|^2 = \frac{3}{4}\mu^2 E_0^2\left|-\sqrt{\frac{2}{3}}\beta_{2S}^* + \frac{2}{\sqrt{3}}e^{-i2\pi/3}\alpha_{2+}^*\right|^2 \tag{286}$$

$$|\langle 2-; +|\mu^+ \cdot E_R^{(+)}|1; -2\pi/3\rangle|^2 = 0 \tag{287}$$

$$|\langle 2-; -|\mu^+ \cdot E_R^{(+)}|1; -2\pi/3\rangle|^2 = 0 \tag{288}$$

-continued $$|\langle 2S; +|\mu^+ \cdot E_L^{(+)}|1; -2\pi/3\rangle|^2 = \frac{3}{4}\mu^2 E_0^2 \left|\sqrt{\frac{2}{3}}\alpha_{2S}^* - \frac{1}{\sqrt{3}}\beta_{2S}^*\right|^2 \quad (289)$$

$$|\langle 2S; -|\mu^+ \cdot E_L^{(+)}|1; -2\pi/3\rangle|^2 = \frac{3}{4}\mu^2 E_0^2 \left|-\sqrt{\frac{2}{3}}\beta_{2S}^* - \frac{1}{\sqrt{3}}\alpha_{2S}^*\right|^2 \quad (290)$$

$$|\langle 2+; +|\mu^+ \cdot E_L^{(+)}|1; -2\pi/3\rangle|^2 = 0 \quad (291)$$

$$|\langle 2+; -|\mu^+ \cdot E_L^{(+)}|1; -2\pi/3\rangle|^2 = 0 \quad (292)$$

$$|\langle 2-; +|\mu^+ \cdot E_L^{(+)}|1; -2\pi/3\rangle|^2 = 0 \quad (293)$$

$$|\langle 2-; -|\mu^+ \cdot E_L^{(+)}|1; -2\pi/3\rangle|^2 = 0 \quad (294)$$

14 Single Exciton Transitions

Here we consider the transitions from the ground state $|0\rangle$ to the single exciton states. The matrix element needed are already given in Eqs. (119) through (124). One finds $$\langle 1; 0|\mu^+ \cdot E_R^{(+)}|0\rangle = 0 \quad (295)$$

$$\langle 1; 2\pi/3|\mu^+ \cdot E_R^{(+)}|0\rangle = -\frac{\sqrt{3}}{4}\mu E_0 e^{i\psi} e^{-i\phi} e^{i\delta} e^{-i\omega_0 t}[1 - \cos(\theta)] \quad (296)$$

$$\langle 1; -2\pi/3|\mu^+ \cdot E_R^{(+)}|0\rangle = \frac{\sqrt{3}}{4}\mu E_0 e^{-i\psi} e^{-i\phi} e^{i\delta} e^{-i\omega_0 t}[1 + \cos(\theta)] \quad (297)$$

$$\langle 1; 0|\mu^+ \cdot E_L^{(+)}|0\rangle = 0 \quad (298)$$

$$\langle 1; 2\pi/3|\mu^+ \cdot E_L^{(+)}|0\rangle = \frac{\sqrt{3}}{4}\mu E_0 e^{i\psi} e^{i\phi} e^{i\delta} e^{-i\omega_0 t}[1 + \cos(\theta)] \quad (299)$$

$$\langle 1; -2\pi/3|\mu^+ \cdot E_L^{(+)}|0\rangle = -\frac{\sqrt{3}}{4}\mu E_0 e^{-i\psi} e^{i\phi} e^{i\delta} e^{-i\omega_0 t}[1 - \cos(\theta)] \quad (300)$$

The norm squared of these quantities is given by $$|\langle 1; 0|\mu^+ \cdot E_R^{(+)}|0\rangle|^2 = 0 \quad (301)$$

$$|\langle 1; 2\pi/3|\mu^+ \cdot E_R^{(+)}|0\rangle|^2 = \frac{3}{16}\mu^2 E_0^2[1 - \cos(\theta)]^2 \quad (302)$$

$$|\langle 1; -2\pi/3|\mu^+ \cdot E_R^{(+)}|0\rangle|^2 = \frac{3}{16}\mu^2 E_0^2[1 + \cos(\theta)]^2 \quad (303)$$

$$|\langle 1; 0|\mu^+ \cdot E_L^{(+)}|0\rangle|^2 = 0 \quad (304)$$

$$|\langle 1; 2\pi/3|\mu^+ \cdot E_L^{(+)}|0\rangle|^2 = \frac{3}{16}\mu^2 E_0^2[1 + \cos(\theta)]^2 \quad (305)$$

$$|\langle 1; -2\pi/3|\mu^+ \cdot E_L^{(+)}|0\rangle|^2 = -\frac{3}{16}\mu^2 E_0^2[1 - \cos(\theta)]^2 \quad (306)$$

For the special case when $$\theta = 0 \quad (307)$$

This last set of equations reduces to $$|\langle 1; 0|\mu^+ \cdot E_R^{(+)}|0\rangle|^2 = 0 \quad (308)$$

$$|\langle 1; 2\pi/3|\mu^+ \cdot E_R^{(+)}|0\rangle|^2 = 0 \quad (309)$$

$$|\langle 1; -2\pi/3|\mu^+ \cdot E_R^{(+)}|0\rangle|^2 = \frac{3}{4}\mu^2 E_0^2 \quad (310)$$

$$|\langle 1; 0|\mu^+ \cdot E_L^{(+)}|0\rangle|^2 = 0 \quad (311)$$

$$|\langle 1; 2\pi/3|\mu^+ \cdot E_L^{(+)}|0\rangle|^2 = \frac{3}{4}\mu^2 E_0^2 \quad (312)$$

$$|\langle 1; -2\pi/3|\mu^+ \cdot E_L^{(+)}|0\rangle|^2 = 0 \quad (313)$$

15 Case of Randomly Oriented Molecules with the Pump Light Having a Right-Handed Polarization From Eqs. (245) through (268) one has $$|\langle 2S; +|\mu^+ \cdot E_R^{(+)}|1; 2\pi/3\rangle|^2|\langle 1; 2\pi/3|\mu^+ \cdot E_{Rp}^{(+)}|0\rangle|^2 = \quad (314)$$
$$\frac{3}{16}\mu^2 E_0^2 \frac{3}{16}\mu^2 E_p^2[1 - \cos(\theta)]^2[1 + \cos(\theta)]^2 \left|\sqrt{\frac{2}{3}}\alpha_{2S}^* - \frac{1}{\sqrt{3}}\beta_{2S}^*\right|^2$$

$$|\langle 2S; -|\mu^+ \cdot E_R^{(+)}|1; 2\pi/3\rangle|^2|\langle 1; 2\pi/3|\mu^+ \cdot E_{Rp}^{(+)}|0\rangle|^2 = \quad (315)$$
$$\frac{3}{16}\mu^2 E_0^2 \frac{3}{16}\mu^2 E_p^2[1 - \cos(\theta)]^2[1 + \cos(\theta)]^2 \left|-\sqrt{\frac{2}{3}}\beta_{2S}^* - \frac{1}{\sqrt{3}}\alpha_{2S}^*\right|^2$$

$$|\langle 2+; +|\mu^+ \cdot E_R^{(+)}|1; 2\pi/3\rangle|^2|\langle 1; 2\pi/3|\mu^+ \cdot E_{Rp}^{(+)}|0\rangle|^2 = 0 \quad (316)$$

$$|\langle 2+; -|\mu^+ \cdot E_R^{(+)}|1; 2\pi/3\rangle|^2|\langle 1; 2\pi/3|\mu^+ \cdot E_{Rp}^{(+)}|0\rangle|^2 = 0 \quad (317)$$

$$|\langle 2-; +|\mu^+ \cdot E_R^{(+)}|1; 2\pi/3\rangle|^2|\langle 1; 2\pi/3|\mu^+ \cdot E_{Rp}^{(+)}|0\rangle|^2 = 0 = \quad (318)$$
$$\frac{3}{16}\mu^2 E_0^2 \frac{3}{16}\mu^2 E_p^2[1 - \cos(\theta)]^2[1 - \cos(\theta)]^2 \left|\sqrt{\frac{2}{3}}\alpha_{2-}^* + \frac{2}{\sqrt{3}}e^{i2\pi/3}\beta_{2-}^*\right|^2$$

$$|\langle 2-; -|\mu^+ \cdot E_R^{(+)}|1; 2\pi/3\rangle|^2|\langle 1; 2\pi/3|\mu^+ \cdot E_{Rp}^{(+)}|0\rangle|^2 = \quad (319)$$
$$\frac{3}{16}\mu^2 E_0^2 \frac{3}{16}\mu^2 E_p^2[1 - \cos(\theta)]^2[1 - \cos(\theta)]^2 \left|-\sqrt{\frac{2}{3}}\beta_{2-}^* + \frac{2}{\sqrt{3}}e^{i2\pi/3}\alpha_{2-}^\dagger\right|^2$$

$$|\langle 2S; +|\mu^+ \cdot E_L^{(+)}|1; 2\pi/3\rangle|^2|\langle 1; 2\pi/3|\mu^+ \cdot E_{Rp}^{(+)}|0\rangle|^2 = \quad (320)$$
$$\frac{3}{16}\mu^2 E_0^2 \frac{3}{16}\mu^2 E_p^2[1 - \cos(\theta)]^2[1 - \cos(\theta)]^2 \left|\sqrt{\frac{2}{3}}\alpha_{2S}^* - \frac{1}{\sqrt{3}}\beta_{2S}^*\right|^2$$

$$|\langle 2S; -|\mu^+ \cdot E_L^{(+)}|1; 2\pi/3\rangle|^2|\langle 1; 2\pi/3|\mu^+ \cdot E_{Rp}^{(+)}|0\rangle|^2 = \quad (321)$$
$$\frac{3}{16}\mu^2 E_0^2 \frac{3}{16}\mu^2 E_p^2[1 - \cos(\theta)]^2[1 - \cos(\theta)]^2 \left|-\sqrt{\frac{2}{3}}\beta_{2S}^* - \frac{1}{\sqrt{3}}\alpha_{2S}^*\right|^2$$

$$|\langle 2+; +|\mu^+ \cdot E_L^{(+)}|1; 2\pi/3\rangle|^2|\langle 1; 2\pi/3|\mu^+ \cdot E_{Rp}^{(+)}|0\rangle|^2 = 0 \quad (322)$$

$$|\langle 2+; -|\mu^+ \cdot E_L^{(+)}|1; 2\pi/3\rangle|^2|\langle 1; 2\pi/3|\mu^+ \cdot E_{Rp}^{(+)}|0\rangle|^2 = 0 \quad (323)$$

$$|\langle 2-; +|\mu^+ \cdot E_L^{(+)}|1; 2\pi/3\rangle|^2|\langle 1; 2\pi/3|\mu^+ \cdot E_{Rp}^{(+)}|0\rangle|^2 = \quad (324)$$
$$\frac{3}{16}\mu^2 E_0^2 \frac{3}{16}\mu^2 E_p^2[1 - \cos(\theta)]^2[1 + \cos(\theta)]^2 \left|\sqrt{\frac{2}{3}}\alpha_{2-}^* + \frac{2}{\sqrt{3}}e^{i2\pi/3}\beta_{2-}^*\right|^2$$

$$|\langle 2-; -|\mu^+ \cdot E_L^{(+)}|1; 2\pi/3\rangle|^2|\langle 1; 2\pi/3|\mu^+ \cdot E_{Rp}^{(+)}|0\rangle|^2 = \quad (325)$$
$$\frac{3}{16}\mu^2 E_0^2 \frac{3}{16}\mu^2 E_p^2[1 - \cos(\theta)]^2[1 + \cos(\theta)]^2 \left|-\sqrt{\frac{2}{3}}\beta_{2-}^* + \frac{2}{\sqrt{3}}e^{i2\pi/3}\alpha_{2-}^*\right|^2$$

$$|\langle 2S; +|\mu^+ \cdot E_R^{(+)}|1; -2\pi/3\rangle|^2|\langle 1; -2\pi/3|\mu^+ \cdot E_{Rp}^{(+)}|0\rangle|^2 = \quad (326)$$
$$\frac{3}{16}\mu^2 E_0^2 \frac{3}{16}\mu^2 E_p^2[1 + \cos(\theta)]^2[1 - \cos(\theta)]^2 \left|\sqrt{\frac{2}{3}}\alpha_{2S}^* - \frac{1}{\sqrt{3}}\beta_{2S}^*\right|^2$$

-continued $$|\langle 2S; -|\mu^+ \cdot E_R^{(+)}|1; -2\pi/3\rangle|^2 |\langle 1; -2\pi/3|\mu^+ \cdot E_{Rp}^{(+)}|0\rangle|^2 = \tag{327}$$

$$\frac{3}{16}\mu^2 E_0^2 \frac{3}{16}\mu^2 E_p^2 [1+\cos(\theta)]^2 [1-\cos(\theta)]^2 \left|-\sqrt{\frac{2}{3}}\beta_{2S}^* - \frac{1}{\sqrt{3}}\beta_{2S}^*\right|^2$$

$$|\langle 2+; +|\mu^+ \cdot E_R^{(+)}|1; -2\pi/3\rangle|^2 |\langle 1; -2\pi/3|\mu^+ \cdot E_{Rp}^{(+)}|0\rangle|^2 = \tag{328}$$

$$\frac{3}{16}\mu^2 E_0^2 \frac{3}{16}\mu^2 E_p^2 [1+\cos(\theta)]^2 [1+\cos(\theta)]^2 \left|\sqrt{\frac{2}{3}}\alpha_{2+}^* + \frac{2}{\sqrt{3}}e^{-i2\pi/3}\beta_{2+}^*\right|^2$$

$$|\langle 2+; -|\mu^+ \cdot E_R^{(+)}|1; -2\pi/3\rangle|^2 |\langle 1; -2\pi/3|\mu^+ \cdot E_{Rp}^{(+)}|0\rangle|^2 = \frac{3}{16}\mu^2 E_0^2 \tag{329}$$

$$\frac{3}{16}\mu^2 E_p^2 [1+\cos(\theta)]^2 [1+\cos(\theta)]^2 \left|-\sqrt{\frac{2}{3}}\beta_{2S}^* + \frac{2}{\sqrt{3}}e^{-i2\pi/3}\alpha_{2+}^*\right|^2$$

$$|\langle 2-; +|\mu^+ \cdot E_R^{(+)}|1; -2\pi/3\rangle|^2 |\langle 1; -2\pi/3|\mu^+ \cdot E_{Rp}^{(+)}|0\rangle|^2 = 0 \tag{330}$$

$$|\langle 2-; -|\mu^+ \cdot E_R^{(+)}|1; -2\pi/3\rangle|^2 |\langle 1; -2\pi/3|\mu^+ \cdot E_{Rp}^{(+)}|0\rangle|^2 = 0 \tag{331}$$

$$|\langle 2S; +|\mu^+ \cdot E_L^{(+)}|1; -2\pi/3\rangle|^2 |\langle 1; -2\pi/3|\mu^+ \cdot E_{Rp}^{(+)}|0\rangle|^2 = \tag{332}$$

$$\frac{3}{16}\mu^2 E_0^2 \frac{3}{16}\mu^2 E_p^2 [1+\cos(\theta)]^2 [1+\cos(\theta)]^2 \left|\sqrt{\frac{2}{3}}\alpha_{2S}^* - \frac{1}{\sqrt{3}}\beta_{2S}^*\right|^2$$

$$|\langle 2S; -|\mu^+ \cdot E_L^{(+)}|1; -2\pi/3\rangle|^2 |\langle 1; -2\pi/3|\mu^+ \cdot E_{Rp}^{(+)}|0\rangle|^2 = \tag{333}$$

$$\frac{3}{16}\mu^2 E_0^2 \frac{3}{16}\mu^2 E_p^2 [1+\cos(\theta)]^2 [1+\cos(\theta)]^2 \left|-\sqrt{\frac{2}{3}}\beta_{2S}^* - \frac{1}{\sqrt{3}}\alpha_{2S}^*\right|^2$$

$$|\langle 2+; +|\mu^+ \cdot E_L^{(+)}|1; -2\pi/3\rangle|^2 |\langle 1; -2\pi/3|\mu^+ \cdot E_{Rp}^{(+)}|0\rangle|^2 = \tag{334}$$

$$\frac{3}{16}\mu^2 E_0^2 \frac{3}{16}\mu^2 E_p^2 [1+\cos(\theta)]^2 [1-\cos(\theta)]^2 \left|\sqrt{\frac{2}{3}}\alpha_{2+}^* + \frac{2}{\sqrt{3}}e^{-i2\pi/3}\beta_{2+}^*\right|^2$$

$$|\langle 2+; -|\mu^+ \cdot E_L^{(+)}|1; -2\pi/3\rangle|^2 |\langle 1; -2\pi/3|\mu^+ \cdot E_{Rp}^{(+)}|0\rangle|^2 = \frac{3}{16}\mu^2 E_0^2 \tag{335}$$

$$\frac{3}{16}\mu^2 E_p^2 [1+\cos(\theta)]^2 [1-\cos(\theta)]^2 \left|-\sqrt{\frac{2}{3}}\beta_{2+}^* + \frac{2}{\sqrt{3}}e^{-i2\pi/3}\alpha_{2+}^*\right|^2$$

$$|\langle 2-; +|\mu^+ \cdot E_L^{(+)}|1; -2\pi/3\rangle|^2 |\langle 1; -2\pi/3|\mu^+ \cdot E_{Rp}^{(+)}|0\rangle|^2 = 0 \tag{336}$$

$$|\langle 2-; -|\mu^+ \cdot E_L^{(+)}|1; -2\pi/3\rangle|^2 |\langle 1; -2\pi/3|\mu^+ \cdot E_{Rp}^{(+)}|0\rangle|^2 = 0 \tag{337}$$

We now average over all orientations. This averaging is performed according to $$\langle F \rangle = \frac{1}{4\pi}\int_0^{2\pi} d\phi \int_0^{\pi} \sin(\theta)d\theta F(\theta, \phi). \tag{338}$$

One finds $$\langle [1+\cos^2(\theta)][1+\cos^2(\theta)]\rangle = \frac{28}{15} = \frac{4\cdot 7}{3\cdot 5} \tag{339}$$

$$\langle [1+\cos^2(\theta)][1-\cos^2(\theta)]\rangle = \frac{4}{5} \tag{340}$$

$$\langle [1-\cos^2(\theta)][1-\cos^2(\theta)]\rangle = \frac{8}{15}. \tag{341}$$

Hence, one has $$\langle |\langle 2S; +|\mu^+ \cdot E_R^{(+)}|1; 2\pi/3\rangle|^2 |\langle 1; 2\pi/3|\mu^+ \cdot E_{Rp}^{(+)}|0\rangle|^2 \rangle = \tag{342}$$

$$\frac{3}{16}\mu^2 E_0^2 \frac{3}{16}\mu^2 E_p^2 \frac{4}{5} \left|\sqrt{\frac{2}{3}}\alpha_{2S}^* - \frac{1}{\sqrt{3}}\beta_{2S}^*\right|^2$$

$$\langle |\langle 2S; -|\mu^+ \cdot E_R^{(+)}|1; 2\pi/3\rangle|^2 |\langle 1; 2\pi/3|\mu^+ \cdot E_{Rp}^{(+)}|0\rangle|^2 \rangle = \tag{343}$$

$$\frac{3}{16}\mu^2 E_0^2 \frac{3}{16}\mu^2 E_p^2 \frac{4}{5} \left|-\sqrt{\frac{2}{3}}\beta_{2S}^* - \frac{1}{\sqrt{3}}\alpha_{2S}^*\right|^2$$

$$\langle |\langle 2+; +|\mu^+ \cdot E_R^{(+)}|1; 2\pi/3\rangle|^2 |\langle 1; 2\pi/3|\mu^+ \cdot E_{Rp}^{(+)}|0\rangle|^2 \rangle = 0 \tag{344}$$

$$\langle |\langle 2+; -|\mu^+ \cdot E_R^{(+)}|1; 2\pi/3\rangle|^2 |\langle 1; 2\pi/3|\mu^+ \cdot E_{Rp}^{(+)}|0\rangle|^2 \rangle = 0 \tag{345}$$

$$\langle |\langle 2-; +|\mu^+ \cdot E_R^{(+)}|1; 2\pi/3\rangle|^2 |\langle 1; 2\pi/3|\mu^+ \cdot E_{Rp}^{(+)}|0\rangle|^2 \rangle = \tag{346}$$

$$\frac{3}{16}\mu^2 E_0^2 \frac{3}{16}\mu^2 E_p^2 \frac{8}{15} \left|\sqrt{\frac{2}{3}}\alpha_{2-}^* + \frac{2}{\sqrt{3}}e^{i2\pi}\beta_{2-}^*\right|^2$$

$$\langle |\langle 2-; -|\mu^+ \cdot E_R^{(+)}|1; 2\pi/3\rangle|^2 |\langle 1; 2\pi/3|\mu^+ \cdot E_{Rp}^{(+)}|0\rangle|^2 \rangle = \tag{347}$$

$$\frac{3}{16}\mu^2 E_0^2 \frac{3}{16}\mu^2 E_p^2 \frac{8}{15} \left|-\sqrt{\frac{2}{3}}\beta_{2-}^* + \frac{2}{\sqrt{3}}e^{i2\pi}\alpha_{2-}^*\right|^2$$

$$\langle |\langle 2S; +|\mu^+ \cdot E_L^{(+)}|1; 2\pi/3\rangle|^2 |\langle 1; 2\pi/3|\mu^+ \cdot E_{Rp}^{(+)}|0\rangle|^2 \rangle = \tag{348}$$

$$\frac{3}{16}\mu^2 E_0^2 \frac{3}{16}\mu^2 E_p^2 \frac{8}{15} \left|\sqrt{\frac{2}{3}}\alpha_{2S}^* - \frac{1}{\sqrt{3}}\beta_{2S}^*\right|^2$$

$$\langle |\langle 2S; -|\mu^+ \cdot E_L^{(+)}|1; 2\pi/3\rangle|^2 |\langle 1; 2\pi/3|\mu^+ \cdot E_{Rp}^{(+)}|0\rangle|^2 \rangle = \tag{349}$$

$$\frac{3}{16}\mu^2 E_0^2 \frac{3}{16}\mu^2 E_p^2 \frac{8}{15} \left|-\sqrt{\frac{2}{3}}\beta_{2S}^* - \frac{1}{\sqrt{3}}\alpha_{2S}^*\right|^2$$

$$\langle |\langle 2+; +|\mu^+ \cdot E_L^{(+)}|1; 2\pi/3\rangle|^2 |\langle 1; 2\pi/3|\mu^+ \cdot E_{Rp}^{(+)}|0\rangle|^2 \rangle = 0 \tag{350}$$

$$\langle |\langle 2+; -|\mu^+ \cdot E_L^{(+)}|1; 2\pi/3\rangle|^2 |\langle 1; 2\pi/3|\mu^+ \cdot E_{Rp}^{(+)}|0\rangle|^2 \rangle = 0 \tag{351}$$

$$\langle |\langle 2-; +|\mu^+ \cdot E_L^{(+)}|1; 2\pi/3\rangle|^2 |\langle 1; 2\pi/3|\mu^+ \cdot E_{Rp}^{(+)}|0\rangle|^2 \rangle = \tag{352}$$

$$\frac{3}{16}\mu^2 E_0^2 \frac{3}{16}\mu^2 E_p^2 \frac{4}{5} \left|\sqrt{\frac{2}{3}}\alpha_{2-}^* + \frac{2}{\sqrt{3}}e^{i2\pi}\beta_{2-}^*\right|^2$$

$$\langle |\langle 2-; -|\mu^+ \cdot E_L^{(+)}|1; 2\pi/3\rangle|^2 |\langle 1; 2\pi/3|\mu^+ \cdot E_{Rp}^{(+)}|0\rangle|^2 \rangle = \tag{353}$$

$$\frac{3}{16}\mu^2 E_0^2 \frac{3}{16}\mu^2 E_p^2 \frac{4}{5} \left|-\sqrt{\frac{2}{3}}\beta_{2-}^* + \frac{2}{\sqrt{3}}e^{i2\pi}\alpha_{2-}^*\right|^2$$

$$\langle |\langle 2S; +|\mu^+ \cdot E_R^{(+)}|1; -2\pi/3\rangle|^2 |\langle 1; -2\pi/3|\mu^+ \cdot E_{Rp}^{(+)}|0\rangle|^2 \rangle = \tag{354}$$

$$\frac{3}{16}\mu^2 E_0^2 \frac{3}{16}\mu^2 E_p^2 \frac{4}{5} \left|\sqrt{\frac{2}{3}}\alpha_{2S}^* - \frac{1}{\sqrt{3}}\beta_{2S}^*\right|^2$$

$$\langle |\langle 2S; -|\mu^+ \cdot E_R^{(+)}|1; -2\pi/3\rangle|^2 |\langle 1; -2\pi/3|\mu^+ \cdot E_{Rp}^{(+)}|0\rangle|^2 \rangle = \tag{355}$$

$$\frac{3}{16}\mu^2 E_0^2 \frac{3}{16}\mu^2 E_p^2 \frac{4}{5} \left|-\sqrt{\frac{2}{3}}\alpha_{2S}^* - \frac{1}{\sqrt{3}}\beta_{2S}^*\right|^2$$

$$\langle |\langle 2+; +|\mu^+ \cdot E_R^{(+)}|1; -2\pi/3\rangle|^2 |\langle 1; -2\pi/3|\mu^+ \cdot E_{Rp}^{(+)}|0\rangle|^2 \rangle = \tag{356}$$

-continued $$\frac{3}{16}\mu^2 E_0^2 \frac{3}{16}\mu^2 E_p^2 \frac{28}{15}\left|\sqrt{\frac{2}{3}}\alpha_{2+}^* + \frac{2}{\sqrt{3}}e^{-i2\pi/3}\beta_{2+}^*\right|^2$$

(357)

$$\langle|\langle 2+;-|\mu^+ \cdot E_R^{(+)}|1;-2\pi/3\rangle|^2 |\langle 1;-2\pi/3|\mu^+ \cdot E_{Rp}^{(+)}|0\rangle|^2\rangle =$$

$$\frac{3}{16}\mu^2 E_0^2 \frac{3}{16}\mu^2 E_p^2 \frac{28}{15}\left|-\sqrt{\frac{2}{3}}\beta_{2+}^* + \frac{2}{\sqrt{3}}e^{-i2\pi/3}\alpha_{2+}^*\right|^2$$

$$\langle|\langle 2-;+|\mu^+ \cdot E_R^{(+)}|1;-2\pi/3\rangle|^2 |\langle 1;-2\pi/3|\mu^+ \cdot E_{Rp}^{(+)}|0\rangle|^2\rangle = 0 \quad (358)$$

$$\langle|\langle 2-;-|\mu^+ \cdot E_R^{(+)}|1;-2\pi/3\rangle|^2 |\langle 1;-2\pi/3|\mu^+ \cdot E_{Rp}^{(+)}|0\rangle|^2\rangle = 0 \quad (359)$$

$$\langle|\langle 2S;+|\mu^+ \cdot E_L^{(+)}|1;-2\pi/3\rangle|^2 |\langle 1;-2\pi/3|\mu^+ \cdot E_{Rp}^{(+)}|0\rangle|^2\rangle = \quad (360)$$

$$\frac{3}{16}\mu^2 E_0^2 \frac{3}{16}\mu^2 E_p^2 \frac{28}{15}\left|\sqrt{\frac{2}{3}}\alpha_{2S}^* - \frac{1}{\sqrt{3}}\beta_{2S}^*\right|^2$$

$$\langle|\langle 2S;-|\mu^+ \cdot E_L^{(+)}|1;-2\pi/3\rangle|^2 |\langle 1;-2\pi/3|\mu^+ \cdot E_{Rp}^{(+)}|0\rangle|^2\rangle = \quad (361)$$

$$\frac{3}{16}\mu^2 E_0^2 \frac{3}{16}\mu^2 E_p^2 \frac{28}{15}\left|-\sqrt{\frac{2}{3}}\beta_{2S}^* - \frac{1}{\sqrt{3}}\alpha_{2S}^*\right|^2$$

$$\langle|\langle 2+;+|\mu^+ \cdot E_L^{(+)}|1;-2\pi/3\rangle|^2 |\langle 1;-2\pi/3|\mu^+ \cdot E_{Rp}^{(+)}|0\rangle|^2\rangle = \quad (362)$$

$$\frac{3}{16}\mu^2 E_0^2 \frac{3}{16}\mu^2 E_p^2 \frac{4}{5}\left|\sqrt{\frac{2}{3}}\alpha_{2+}^* + \frac{2}{\sqrt{3}}e^{-i2\pi/3}\beta_{2+}^*\right|^2$$

$$\langle|\langle 2+;-|\mu^+ \cdot E_L^{(+)}|1;-2\pi/3\rangle|^2 |\langle 1;-2\pi/3|\mu^+ \cdot E_{Rp}^{(+)}|0\rangle|^2\rangle = \quad (363)$$

$$\frac{3}{16}\mu^2 E_0^2 \frac{3}{16}\mu^2 E_p^2 \frac{4}{5}\left|-\sqrt{\frac{2}{3}}\beta_{2+}^* + \frac{2}{\sqrt{3}}e^{-i2\pi/3}\alpha_{2+}^*\right|^2$$

$$\langle|\langle 2-;+|\mu^+ \cdot E_L^{(+)}|1;-2\pi/3\rangle|^2 |\langle 1;-2\pi/3|\mu^+ \cdot E_{Rp}^{(+)}|0\rangle|^2\rangle = 0 \quad (364)$$

$$\langle|\langle 2-;-|\mu^+ \cdot E_L^{(+)}|1;-2\pi/3\rangle|^2 |\langle 1;-2\pi/3|\mu^+ \cdot E_{Rp}^{(+)}|0\rangle|^2\rangle = 0 \quad (365)$$

16 Special Case Δ=K=0

Here we consider the case $$\Delta = K = 0. \quad (366)$$

This is the noninteracting exciton case. In addition, we restrict our attention to the case when J is negative ("J" stacking), that is $$J = -|J| \quad (367)$$

Equations (125) and (126) yield $$E_{2S;+} = 2E_0 + 2|J| \quad (368)$$

$$|2S;+\rangle = -\frac{\sqrt{2}}{3}|2Sa\rangle + \frac{1}{3}|2Sb\rangle \quad (369)$$

$$\alpha_{2S} = -\frac{\sqrt{2}}{3} \quad (370)$$

$$\beta_{2S} = \frac{1}{3}. \quad (371)$$

Equations (127) and (128) yield $$E_{2S;-} = 2E_0 - 4|J| \quad (372)$$

$$|2S;-\rangle = -\frac{1}{3}|2Sa\rangle - \frac{\sqrt{2}}{3}|2Sb\rangle \quad (373)$$

Equations (133) and (134) yield $$E_{2+;+} = 2E_0 + 2|J| \quad (374)$$

$$|2+;+\rangle = \frac{1}{\sqrt{3}}|2a+\rangle - \sqrt{\frac{2}{3}}\left(1 + e^{-i2\pi/3}\right)|2b+\rangle \quad (375)$$

$$\alpha_{2+} = \frac{1}{\sqrt{3}} \quad (376)$$

$$\beta_{2+} = -\sqrt{\frac{2}{3}}\left(1 + e^{-i2\pi/3}\right) \quad (377)$$

Equations (135) and (136) yield $$E_{2+;-} = 2E_0 - |J| \quad (378)$$

$$|2+;-\rangle = \sqrt{\frac{2}{3}}\left(1 + e^{-i2\pi}\right)|2a+\rangle + \frac{1}{\sqrt{3}}|2b+\rangle \quad (379)$$

Equations (141) and (142) yield $$E_{2-;+} = 2E_0 + 2|J| \quad (380)$$

$$|2-;+\rangle = \frac{1}{\sqrt{3}}|2a-\rangle - \sqrt{\frac{2}{3}}\left(1 + e^{i2\pi/3}\right)|2b-\rangle \quad (381)$$

$$\alpha_{2-} = \frac{1}{\sqrt{3}} \quad (382)$$

$$\beta_{2-} = -\sqrt{\frac{2}{3}}\left(1 + e^{i2\pi/3}\right). \quad (383)$$

Equations (143) and (144) yield $$E_{2-;-} = 2E_0 - |J| \quad (384)$$

$$|2-;-\rangle = \sqrt{\frac{2}{3}}\left(1 + e^{i2\pi/3}\right)|2a-\rangle + \frac{1}{\sqrt{3}}|2b-\rangle. \quad (385)$$

Using Eqs. (370), (371), (376), (377), (382) and (383) one obtains $$\left|\sqrt{\frac{2}{3}}\alpha_{2S} - \frac{1}{\sqrt{3}}\beta_{2S}\right|^2 = \frac{1}{3} \quad (386)$$

$$\left|-\sqrt{\frac{2}{3}}\beta_{2S} - \frac{1}{\sqrt{3}}\alpha_{2S}\right|^2 = 0 \quad (387)$$

$$\left|\sqrt{\frac{2}{3}}\alpha_{2-} + \frac{2}{\sqrt{3}}e^{-i2\pi/3}\beta_{2-}\right|^2 = \frac{2}{3} \quad (388)$$

$$\left|-\sqrt{\frac{2}{3}}\beta_{2-} + \frac{2}{\sqrt{3}}e^{-i2\pi/3}\alpha_{2-}\right|^2 = 0 \quad (389)$$

$$\left|\sqrt{\frac{2}{3}}\alpha_{2+} + \frac{2}{\sqrt{3}}e^{i2\pi/3}\beta_{2+}\right|^2 = \frac{2}{3} \quad (390)$$

$$\left|-\sqrt{\frac{2}{3}}\beta_{2+} + \frac{2}{\sqrt{3}}e^{i2\pi/3}\alpha_{2+}\right|^2 = 0 \quad (391)$$

16.1 Special Case when the Plane of the Molecule is Perpendicular to the Direction of the Light Beam Here we consider the case of Eqs. (369) through (394) and list only the norm squared transition amplitudes that are nonzero.

$$|\langle 2S;+|\mu^+ \cdot E_R^{(+)}|1; 2\pi/3\rangle|^2 = \frac{1}{4}\mu^2 E_0^2 \tag{392}$$

$$|\langle 2-;+|\mu^+ \cdot E_L^{(+)}|1; 2\pi/3\rangle|^2 = \frac{1}{2}\mu^2 E_0^2 \tag{393}$$

$$|\langle 2+;+|\mu^+ \cdot E_R^{(+)}|1; -2\pi/3\rangle|^2 = \frac{1}{2}\mu^2 E_0^2 \tag{394}$$

$$|\langle 2S;+|\mu^+ \cdot E_L^{(+)}|1; -2\pi/3\rangle|^2 = \frac{1}{4}\mu^2 E_0^2. \tag{395}$$

17 the Case when $\Delta = \infty$

Here we consider the case when the limit $\Delta \to \infty$ is taken. From Eqs. (125) and (126) one has $$\lim_{\Delta \to \infty} E_{2S;+} = \infty \tag{396}$$

$$\lim_{\Delta \to \infty} |2S;+\rangle = |2a\rangle \tag{397}$$

$$\lim_{\Delta \to \infty} \alpha_{2S} = 1 \tag{398}$$

$$\lim_{\Delta \to \infty} \beta_{2S} = 0. \tag{399}$$

From Eqs. (127) and (128) on has $$\lim_{\Delta \to \infty} E_{2S;-} = 2E_0 + 2J + K \tag{400}$$

$$\lim_{\Delta \to \infty} |2S;-\rangle = |2Sb\rangle. \tag{401}$$

From Eqs. (133) and (134) one has $$\lim_{\Delta \to \infty} E_{2+;+} = \infty \tag{402}$$

$$\lim_{\Delta \to \infty} |2+;+\rangle = |2a+\rangle \tag{403}$$

$$\lim_{\Delta \to \infty} \alpha_{2+} = 1 \tag{404}$$

$$\lim_{\Delta \to \infty} \beta_{2+} = 0. \tag{405}$$

From Eqs. (135) and (136) on has $$\lim_{\Delta \to \infty} E_{2+;-} = 2E_0 - J + K \tag{406}$$

$$\lim_{\Delta \to \infty} |2+;-\rangle = |2b+\rangle. \tag{407}$$

From Eqs. (141) and (142) one has $$\lim_{\Delta \to \infty} E_{2-;+} = \infty \tag{408}$$

$$\lim_{\Delta \to \infty} |2-;+\rangle = |2a-\rangle \tag{409}$$

$$\lim_{\Delta \to \infty} \alpha_{2-} = 1 \tag{410}$$

$$\lim_{\Delta \to \infty} \beta_{2-} = 0. \tag{411}$$

From Eqs. (143) and (144) one has $$\lim_{\Delta \to \infty} E_{2-;-} = 2E_0 - J + K \tag{412}$$

$$\lim_{\Delta \to \infty} |2-;-\rangle = |2b-\rangle \tag{413}$$

Remembering that the chromophores are in a J aggregate configures, J is negative, that is, $$J = -|J|. \tag{414}$$

The spectrum of energy eigenvalues for this system is thus $$E_{2S;+} = \infty \tag{415}$$

$$E_{2+;+} = \infty \tag{416}$$

$$E_{2-;+} = \infty \tag{417}$$

$$E_{2+;-} = 2E_0 + |J| + K \tag{418}$$

$$E_{2-;-} = 2E_0 + |J| + K \tag{419}$$

$$E_{2S;-} = 2E_0 - 2|J| + K. \tag{420}$$

The states that have infinite energy cannot be accessed. Hence, in the analysis of optically allowed transitions it is only necessary to consider transitions to the states $$|2S;-\rangle, |2+;-\rangle, |2-;-\rangle. \tag{421}$$

17.1 Case when the Plane of the Aggregate is Perpendicular to the Direction of Light Propagation From Eqs. (271) through (294) one obtains the following nonzero norm squared transitions amplitudes $$|\langle 2S;-|\mu^+ \cdot E_R^{(+)}|1; 2\pi/3\rangle|^2 = \frac{1}{4}\mu^2 E_0^2 \tag{422}$$

$$|\langle 2-;-|\mu^+ \cdot E_L^{(+)}|1; 2\pi/3\rangle|^2 = \mu^2 E_0^2 \tag{423}$$

$$|\langle 2+;-|\mu^+ \cdot E_R^{(+)}|1; -2\pi/3\rangle|^2 = \mu^2 E_0^2 \tag{424}$$

$$|\langle 2S;-|\mu^+ \cdot E_L^{(+)}|1; -2\pi/3\rangle|^2 = \frac{1}{4}\mu^2 E_0^2. \tag{425}$$

17.2 the Case of Random Chromophore Orientation

From Eqs. (342) thought (365), keeping only nonzero quantities, one obtains $$\langle |\langle 2S;-|\mu^+ \cdot E_R^{(+)}|1; 2\pi/3\rangle|^2 |\langle 1; 2\pi/3|\mu^+ \cdot E_{Rp}^{(+)}|0\rangle|^2 \rangle = \tag{426}$$
$$\frac{3}{16}\mu^2 E_0^2 \frac{3}{16}\mu^2 E_p^2 \frac{4}{15}$$

$$\langle |\langle 2-;-|\mu^+ \cdot E_R^{(+)}|1; 2\pi/3\rangle|^2 |\langle 1; 2\pi/3|\mu^+ \cdot E_{Rp}^{(+)}|0\rangle|^2 \rangle = \tag{427}$$
$$\frac{3}{16}\mu^2 E_0^2 \frac{3}{16}\mu^2 E_p^2 \frac{8}{15} \cdot \frac{4}{3}$$

$$\langle |\langle 2S;-|\mu^+ \cdot E_L^{(+)}|1; 2\pi/3\rangle|^2 |\langle 1; 2\pi/3|\mu^+ \cdot E_{Rp}^{(+)}|0\rangle|^2 \rangle = \tag{428}$$
$$\frac{3}{16}\mu^2 E_0^2 \frac{3}{16}\mu^2 E_p^2 \frac{8}{15} \cdot \frac{1}{3}$$

$$\langle |\langle 2-;-|\mu^+ \cdot E_L^{(+)}|1; 2\pi/3\rangle|^2 |\langle 1; 2\pi/3|\mu^+ \cdot E_{Rp}^{(+)}|0\rangle|^2 \rangle = \tag{429}$$

-continued $$\langle |\langle 2S; -|\mu^+ \cdot E_R^{(+)}|1; -2\pi/3\rangle|^2 |\langle 1; -2\pi/3|\mu^+ \cdot E_{Rp}^{(+)}|0\rangle|^2\rangle = \frac{3}{16}\mu^2 E_0^2 \frac{3}{16}\mu^2 E_p^2 \frac{4}{5} \cdot \frac{4}{3} \quad (430)$$

$$\langle |\langle 2+; -|\mu^+ \cdot E_R^{(+)}|1; -2\pi/3\rangle|^2 |\langle 1; -2\pi/3|\mu^+ \cdot E_{Rp}^{(+)}|0\rangle|^2\rangle = \frac{3}{16}\mu^2 E_0^2 \frac{3}{16}\mu^2 E_p^2 \frac{4}{5} \cdot \frac{1}{3} \quad (431)$$

$$\langle |\langle 2S; -|\mu^+ \cdot E_L^{(+)}|1; -2\pi/3\rangle|^2 |\langle 1; -2\pi/3|\mu^+ \cdot E_{Rp}^{(+)}|0\rangle|^2\rangle = \frac{3}{16}\mu^2 E_0^2 \frac{3}{16}\mu^2 E_p^2 \frac{28}{15} \cdot \frac{4}{3} \quad (432)$$

$$\langle |\langle 2+; -|\mu^+ \cdot E_L^{(+)}|1; -2\pi/3\rangle|^2 |\langle 1; -2\pi/3|\mu^+ \cdot E_{Rp}^{(+)}|0\rangle|^2\rangle = \frac{3}{16}\mu^2 E_0^2 \frac{3}{16}\mu^2 E_p^2 \frac{28}{15} \cdot \frac{1}{3} \quad (433)$$

$$\frac{3}{16}\mu^2 E_0^2 \frac{3}{16}\mu^2 E_p^2 \frac{4}{5} \cdot \frac{4}{3}.$$

Example 2

To measure the circular dichroism (CD) and the response to different salt conditions of a chromophore monomer and chromophore dimer aggregate in solution, Cy5 was tethered to ssDNA or dsDNA on a linear, flexible, strand of nucleic acid and the salt conditions of the solution were altered to detect changes in the absorbance spectrum and CD.

Figure 6A:
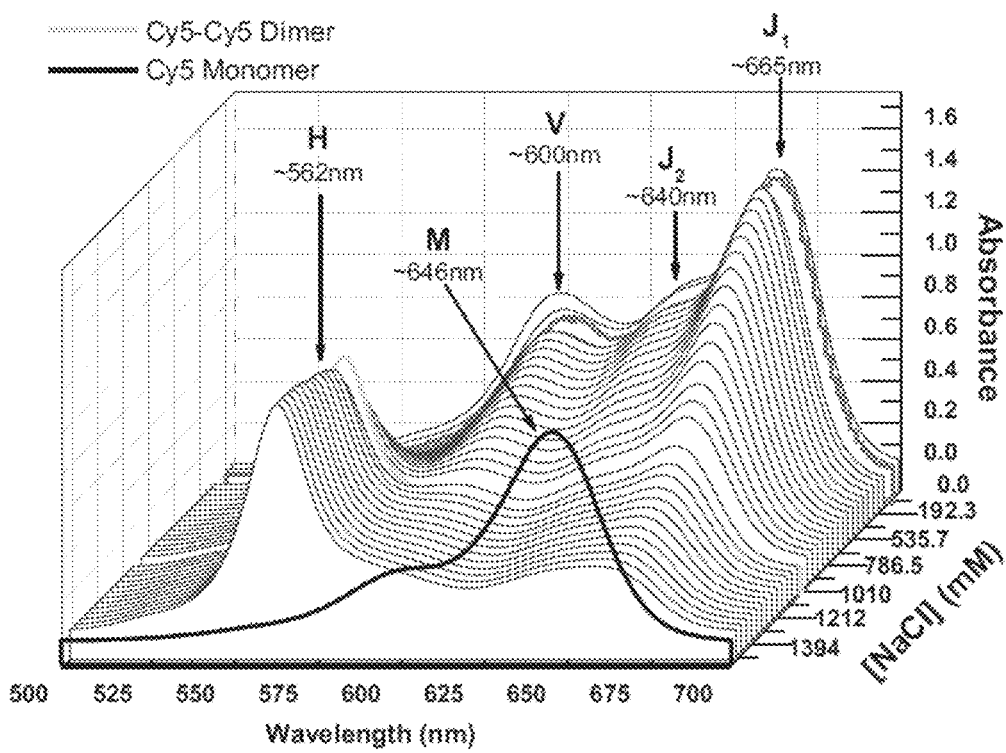
FIG. 6A is a graphical representation of changes in absorbance of the Cy5-Cy5 dimer and Cy5 monomer with changes to salt concentration.
Figure 6B:
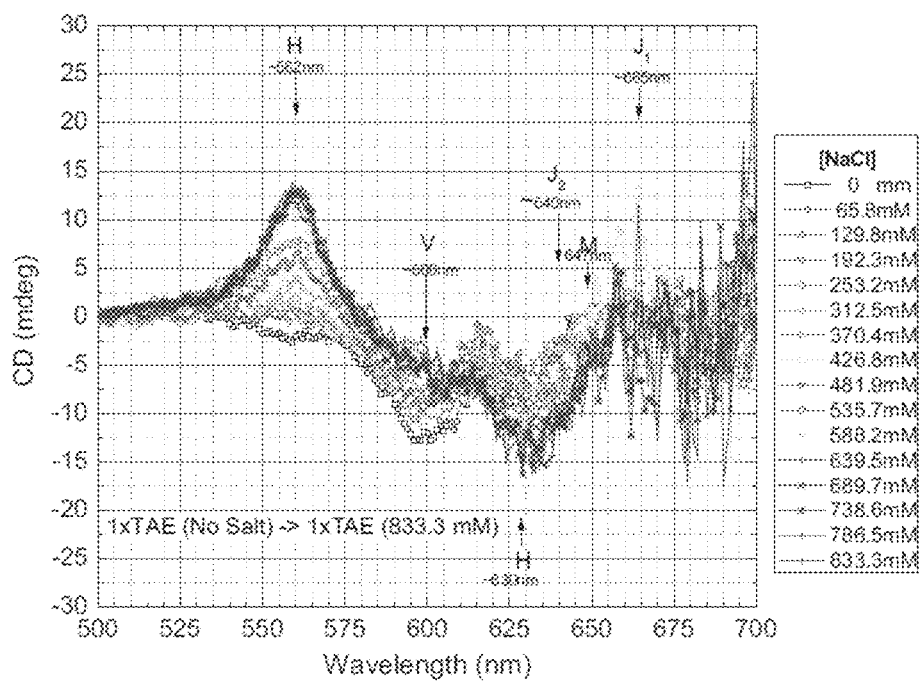
FIG. 6B is a graphical representation of changes in the circular dichroism of the Cy5-Cy5 dimer with changes to salt concentration.

The linear dsDNA-Cy5 strands were exposed to wavelengths of about 500 to about 700 nm. The salt concentrations were altered from 0 to about 1500 mM of NaCl. As shown in FIG. 6A, as the concentration of salt increased, dsDNA-Cy5 showed a reduction in Davydov splitting (J1-V peaks), and a loss of J-dimer characteristics (J1 peak). At about 1000 mM NaCl, dsDNA-Cy5 showed a loss of J-dimer characteristics, with a result of just H-dimer characteristics when compared to the ssDNA-Cy5 monomer. As shown in FIG. 6B, an increase in salt levels from 0 to about 909 mM NaCl showed the CD changed as well, with 0 mM salt showing Davydov splitting and J-dimer characteristics and 909 nM NaCl showing H-dimer characteristics. The change in CD shows that polarization and angle of the chromophore may also be optimized. This is important for stimulating specific chromophores, such as input chromophores, for quantum computing.

Due to the flexibility of the dsDNA-Cy5, it is possible for one skilled in the art to use salt and to fine tune the orientation of the chromophores on a linear oligomer to help force the formation of J-like stacking.

Example 3

Figure 7A:
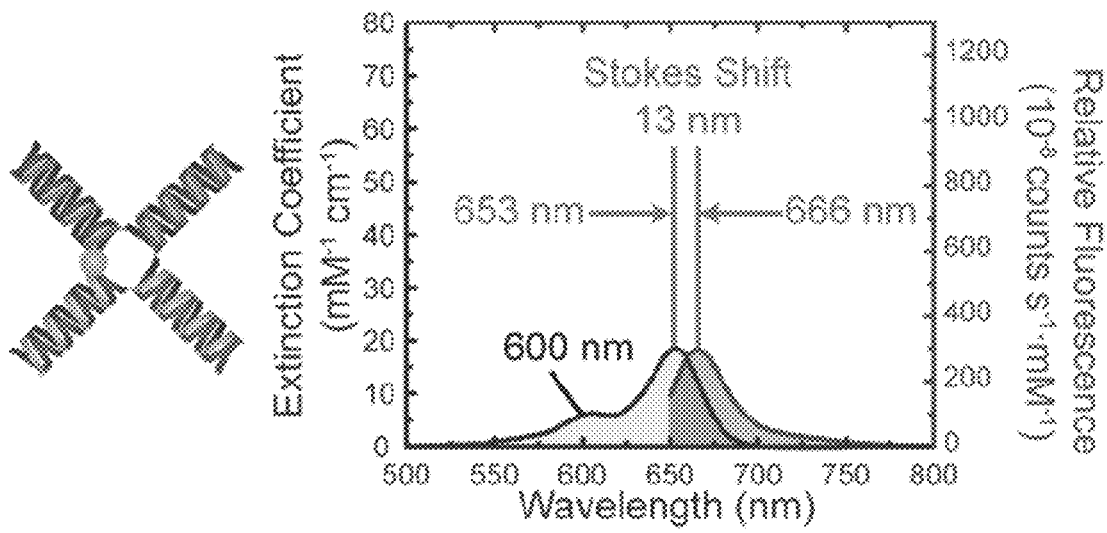
FIG. 7A is the fluorescence spectra of the monomer.
Figure 7B:
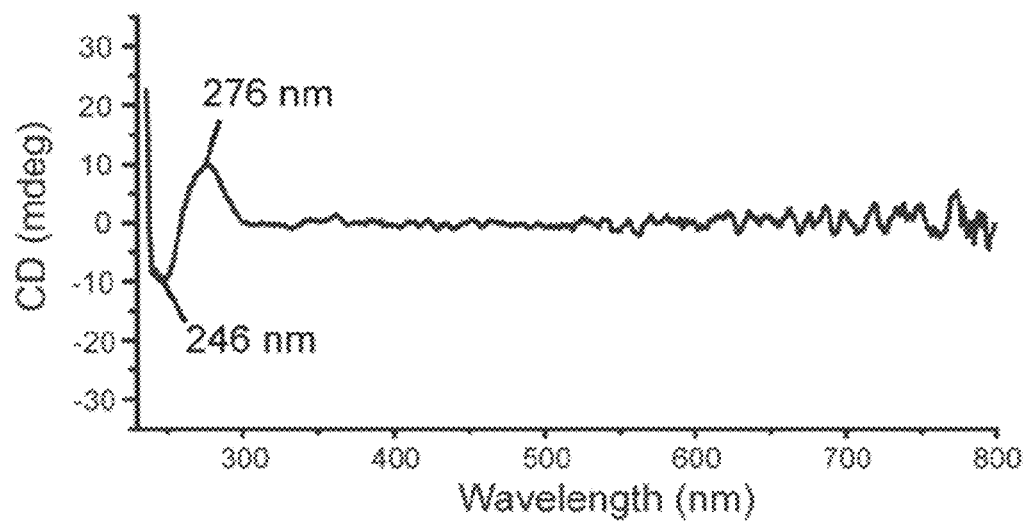
FIG. 7B is the CD of the monomer.
Figure 7C:
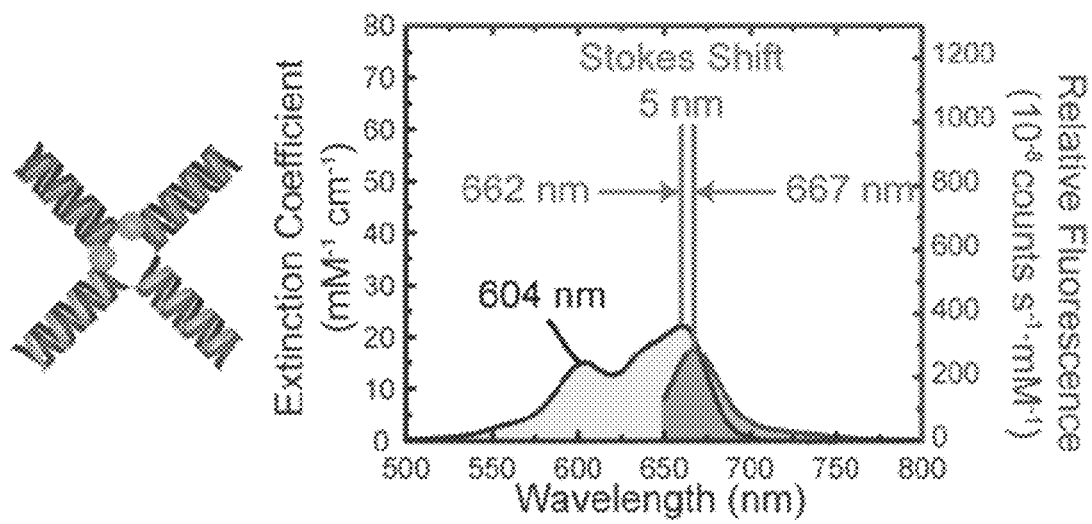
FIG. 7C is the fluorescence spectra of the adjacent dimer.
Figure 7D:
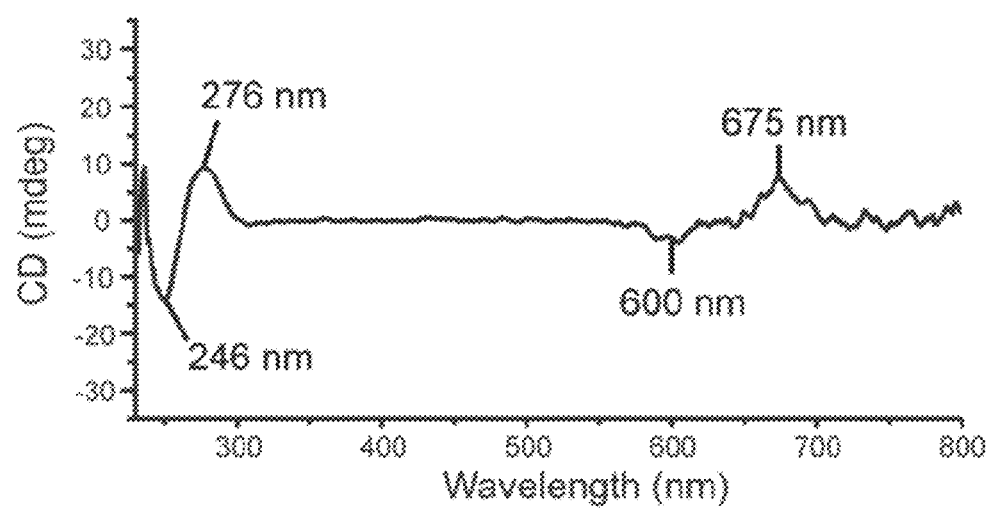
FIG. 7D is the CD of the adjacent dimer.
Figure 7E:
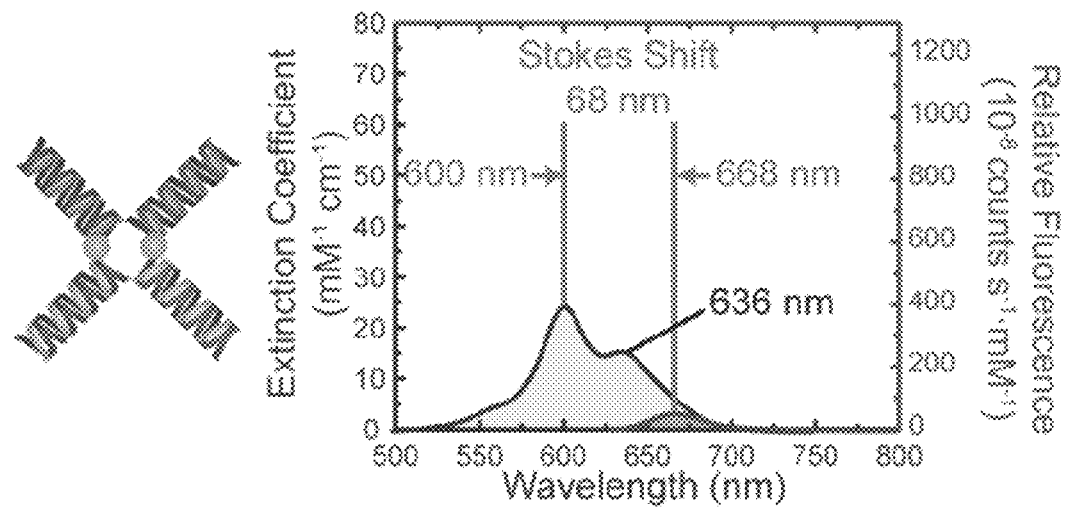
FIG. 7E is the fluorescence spectra of the transverse dimer.
Figure 7F:
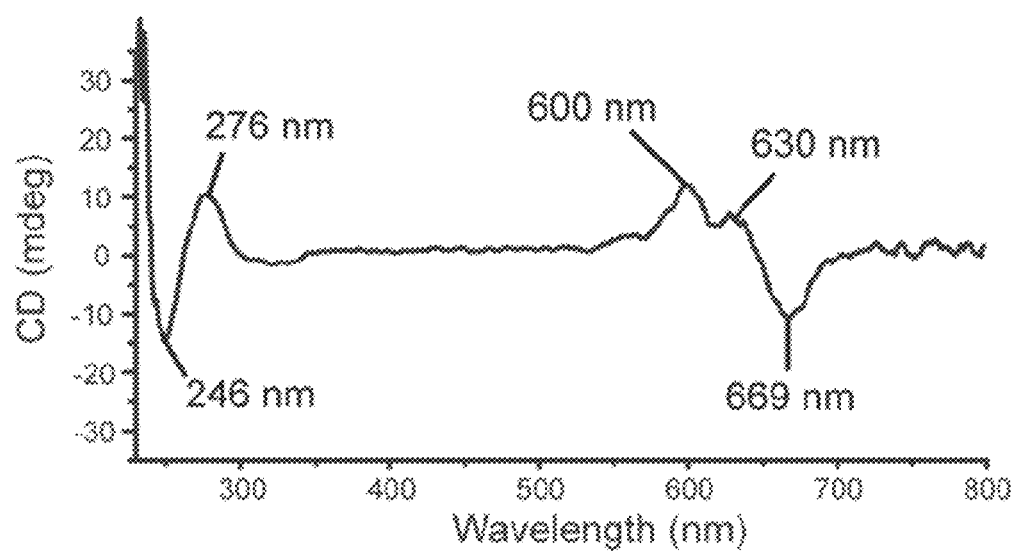
FIG. 7F is the CD of the traverse dimer.
Figure 7G:
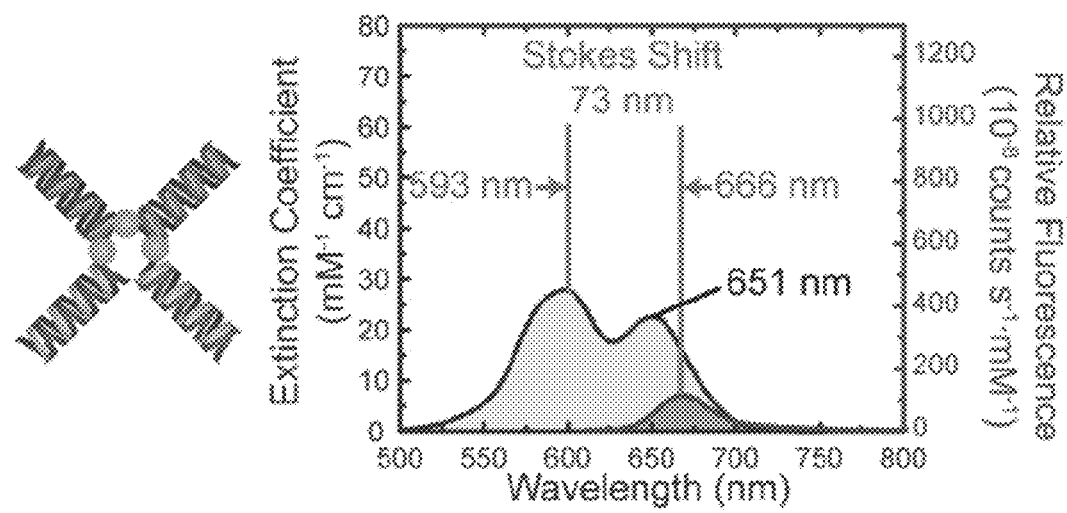
FIG. 7G is the fluorescence spectra of the trimer.
Figure 7H:
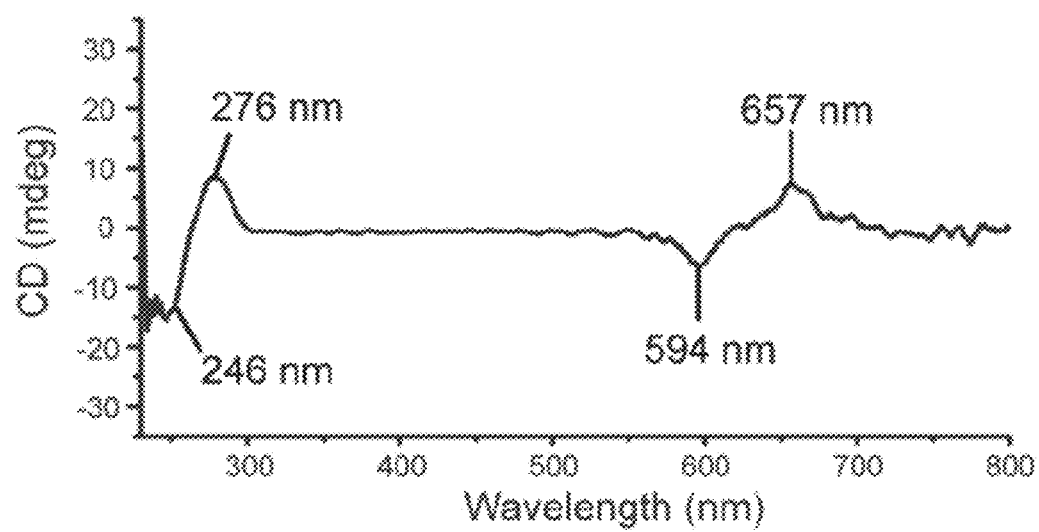
FIG. 7H is the CD of the trimer.
Figure 7I:
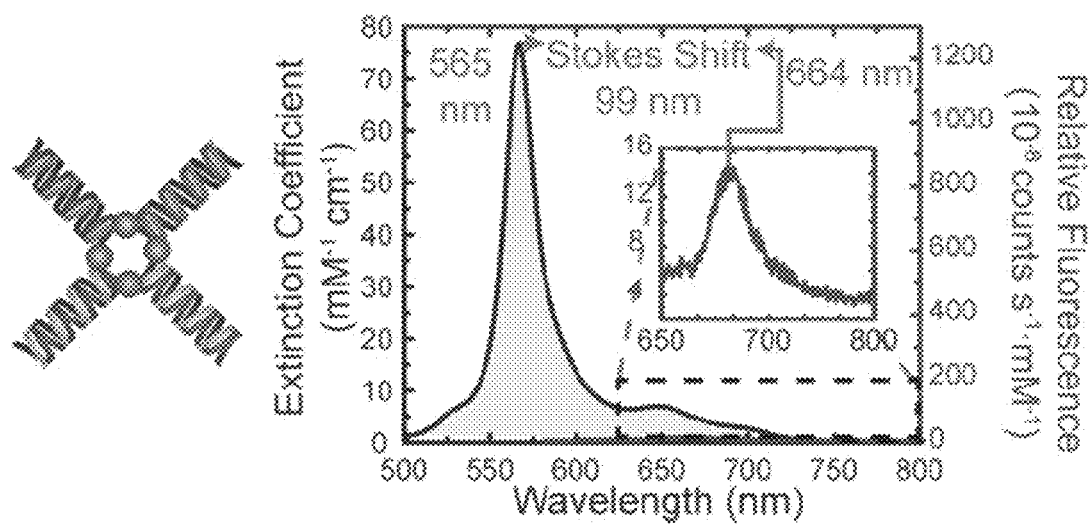
FIG. 7I is the fluorescence spectra of the tetramer.
Figure 7J:
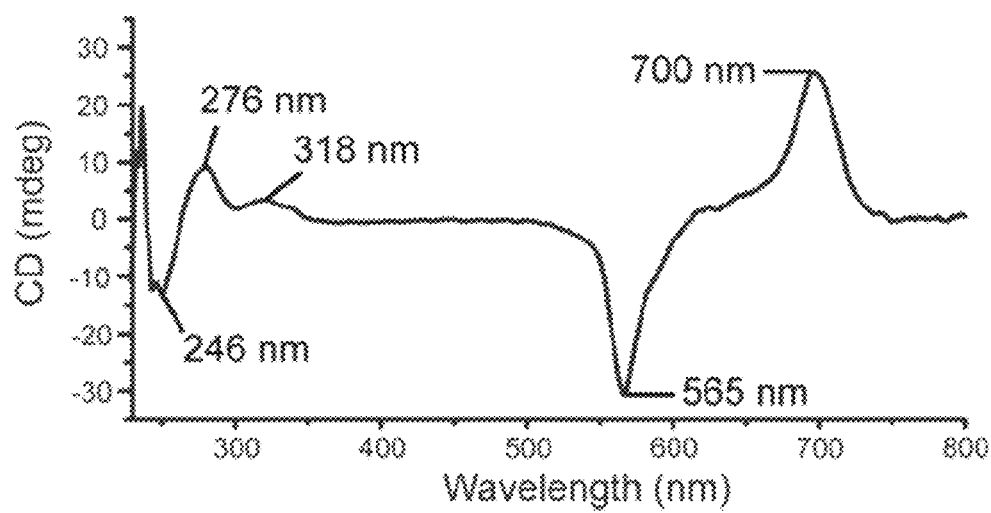
FIG. 7J is the CD of the tetramer. All samples were prepared at 10 µM DNA concentrations in 1×TAE buffer solution with 15 mM $MgCl_2$ added.

To further determine the CD of chromophores attached to a nucleotide template, in this example using an immobile 4AJ architecture, Cy5 chromophores were attached as a monomer (FIG. 7A) (no CD), a dimer where the monomers are adjacent to each other (FIGS. 7 B and 7C), a dimer where the monomers are opposite of each other (FIGS. 7D and 7E), a trimer (FIGS. 7F and 7G), and a tetramer (FIGS. 7H and 7I) (see Cannon et al., *Large Davydov Splitting and Strong Fluorescence Suppression: An Investigation of Exciton Delocalization in DNA-Templated Holliday Junction Dye Aggregates*, 2018, J. Phys. Chem. A, doi:10.1021/acs.jpca.7b12668, Supplemental Information, herein incorporated by reference in its entirety). Absorbance and circular dichroism (CD) were then measured. All measurements were performed with the architectures in a solution of 10 µM DNA, 1×TAE buffer with 15 mM MgCl2.

The monomer reveled a single absorbance and emission peak maxima at 653 and 666 nm, respectively. Although the monomer absorbance peak maximum is slightly red-shifted from the literature value, the shift is most likely due to increased rigidity of the 4AJ structure, chromophore-DNA interactions, and surrounding base sequences. As expected, the dye monomer did not produce a CD signal within the visible range, indicating the absence of molecular chirality and excitonic coupling. Likewise, the CD signals appearing in the UV range at 246 and 276 nm, respectively, result from the expected right-handed macromolecular structure of the β-DNA helix.

The adjacent dimer shows predominantly J-type aggregate behavior, with an absorbance peak maximum at 662 nm that is slightly red-shifted relative to the monomer. This red-shift in absorbance yields a small Stokes shift of 5 nm, which is near resonance florescence behavior. A second, smaller absorbance peak also appears at 602 nm. The appearance of the two peaks is indicative of a Davydov splitting of 58 nm. The adjacent dimer exhibits a split CD signal at 600 and 675 nm. The + of the CD peaks signifies right-handed chirality and is anticipated owing to the right-handed nature of the DNA helix. Because of the predominant J-type behavior and presence of Davydov splitting and CD signal, the chromophores are most likely arranged more or less head-to-tail with some break in planarity between the molecules that still favors J-aggregate stacking.

In contrast, the transverse dimer shows optical behavior that is roughly opposite that of the adjacent dimer. The primary absorbance peak is blue-shifted, with an absorbance maximum at 600 nm and a much smaller absorbance peak at 636 nm, corresponding to an even smaller 36 nm Davydov splitting. A 68 nm Stokes shift is observed when comparing the primary absorbance peak to the fluorescence peak at 668 nm, which is much reduced in intensity, about 97.6%. The blue-shifted primary absorbance peak, the large Stokes shift, and the reduced fluorescence intensity are all indicative of predominantly H-type aggregate behavior. The small Davydov splitting and a relatively strong ∓CD signal at 600 and 669 nm, respectively, of the transverse dimer indicates left-handed chirality and a stacking arrangement that does not stack in a perfectly parallel or H-type arrangement. A small CD signal at 630 and 669 nm shows excitonic coupling between the chromophores. The considerably decreased fluorescence emission is indicative of fluorescence suppression due to a forbidden optical transition from the higher energy excited state that is achieved with an H-like packing arrangement.

The trimer shows absorbance and fluorescence properties similar to the transverse dimer. Most notably, the trimer absorbance spectrum shows an absorbance peak at 593 nm that is blue-shifted from the monomer by 40 nm and a smaller peak at 651 nm that is slightly blue-shifted by 2 nm. The absorbance spectrum also reveals broadening of the primary peak by 15 nm compared to the monomer, as indicated by an increase in the full-width at half-maximum value. Without being bound to a particular theory, the broadening mostly likely arises from a distribution of trimer dye configurations (i.e., dye positions and orientations) within the sample population. In combination with the blue-shifted absorbance peak, the timer shows about an 85% suppression of the fluorescence emission intensity relative to the monomer, indicative of net H-aggregate behavior. Similar to the other aggregate configurations, the trimer has an observed excitonically coupled circular dichroism (EC-CD) signal that, though small, indicates a slightly imperfect stacking arrangement. Additionally, the aggregate displays right-handedness, similar to the adjacent dimer.

The tetramer dye aggregate configuration produces the most interesting optical spectra. A large Davydov splitting of 125 nm (397.5 meV), extensive enough to induce a visible color change in the solution, was observed. This is the largest reported splitting for DNA templated dye aggregates. The Davydov splitting is characterized by a significantly blue-shifted intense absorbance peak at 565 nm and a red-shifted much less intense peak at 690 nm. Though difficult to resolve in the absorption spectrum, the absorbance peak at 690 nm is further substantiated by a large signal in the CD spectrum at 700 nm. Note that the differences in extinction coefficients of the various dye aggregates result from two key effects: (1) the differences in dye number and (2) exciton delocalization and exciton-vibrational interactions. The tetramer also exhibits strong fluorescence suppression behavior at 664 nm, with a 97.6% decrease in the fluorescent emission relative to the monomer, as determined by peak area. The large Davydov splitting, strong fluorescence suppression, and 99 nm Stokes shift provide solid evidence of a dye assembly with predominantly H-type stacking. The pronounced $\mp$CD signal of the tetramer configuration indicates strong exciton coupling between the dyes and reveals that the dyes are oriented predominantly in a parallel manner that is supported by the absorbance peak at 690 nm. Comparing the optical spectra of the immobile 4AJ-templated tetramer presented here with the mobile 4AJ-templated tetramer observed in a prior study, the most notable difference is in the CD spectrum (see Cannon, B. L., et al., Coherent Exciton Delocalization in a Two-State DNA-Templated Dye Aggregate System, *J. Phys. Chem. A.*, 2017, 121:6905-16, herein incorporated by reference in its entirety). Interestingly, the immobile tetramer shows right-handedness, while the mobile tetramer shows left-handedness. Additionally, an absorbance peak at 665 nm was observed for the mobile 4AJ-templated tetramer. In contrast, for the immobile tetramer, a very subtle peak was observed at 690 nm that was further supported by a strong CD signal. These differences are most likely due to the base-pair stacking of the immobile tetramer locking the aggregate core such that the DNA junction does not undergo restacking. The mobile tetramer undergoes DNA breathing and base-pair restacking and was found to partition into two J-dimer pairs that are displaced either horizontally or vertically along the arms, which accounts for the observed 665 nm absorbance peak.

Therefore, each of the different arrangements shows unique absorbance and emittance properties that may be leveraged in the different embodiments.

The inventions being thus described, it will be obvious that the same may be varied in many ways. Such variations are not to be regarded as a departure from the spirit and scope of the inventions and all such modifications are intended to be included within the scope of the following claims.

What is claimed:

1. An optically active medium for a nonreciprocal optical device comprising a chromophore aggregate of two or more chromophores, wherein the two or more chromophores are coupled end-to-end forming a J-aggregate.

2. The optically active medium of claim 1, wherein the two or more chromophores are one or more of a xanthene, fluorescein, rhodamine, oregon green, eosin, Texas red, cyanine, indocarbocyanine, oxacarbocyanine, thiacarbocyanine, merocyanine, squaraine, Seta, SeTau, Square dyes, naphthalene, dansyl, prodan, coumarin, oxadiazole, pyridyloxazole, nitrobenzoxadiazole, benzoxadiazole, anthracene, anthraquinone, DRAQ5, DRAQ7, CyTRAK Orange, pyrene, cascade blue, oxazine, Nile red, Nile blue, cresyl violet, oxazine 170, acridine, proflavin, acridine orange, acridine yellow, arylmethine, auramine, crystal violet, malachite green, tetrapyrrole, porphin, phthalocyanine, and bilirubin, and/or a combination thereof.

3. The optically active medium of claim 1, wherein the chromophore aggregate is a dimer.

4. The optically active medium of claim 1, wherein the chromophore aggregate is a trimer.

5. The optically active medium of claim 4, wherein the trimer has a triangular configuration.

6. The optically active medium of claim 1, wherein the chromophore aggregate is a population of aggregates.

7. The optically active medium of claim 6, wherein the population of aggregates is configured randomly.

8. The optically active medium of claim 6, wherein up to about 1% of the population of aggregates are configured perpendicular to the propagation of light.

9. The optically active medium of claim 6, wherein up to about 50% of the population of aggregates are configured perpendicular to the propagation of light.

10. The optically active medium of claim 6, wherein up to about 90% of the population of aggregates are configured perpendicular to the propagation of light.

11. The optically active medium of claim 1, wherein at least one chromophore of the aggregate is configured to have increased steric hindrance.

12. The optically active medium of claim 11, wherein at least one chromophore of the aggregate is modified by a rotaxane ring.

13. The optically active medium of claim 12, wherein the rotaxane ring is further substituted.

14. The optically active medium of claim 1, further comprising a nucleotide oligomer, wherein the nucleotide oligomer holds the two or more chromophores end-to-end-like stacking.

15. The optically active medium of claim 14, wherein the nucleotide oligomer is made of RNA, DNA, BNA, LNA, PNA, and/or UNA, and/or a combination thereof.

16. The optically active medium of claim 15, wherein the nucleotide oligomer is made of DNA.

17. The optically active medium of claim 16, wherein said nucleotide oligomer is a nucleotide brick.

18. The optically active medium of claim 17, wherein the nucleotide brick is about 24 to 42 nucleotides in length.

19. The optically active medium of claim 16, wherein the number of nucleotide bricks is between 1 and about 5,000 bricks.

20. The optically active medium of claim 19, wherein the nucleotide bricks self-assemble into a nucleotide canvas.

21. The optically active medium of claim 1, wherein the two or more chromophores are covalently linked end-to-end.

22. A nonreciprocal optical device, comprising:
a signal light; and
the optically active medium of claim 1.

23. The nonreciprocal optical device of claim 22, wherein the device is an optical isolator.

24. The nonreciprocal optical device of claim 22, wherein the device is an optical circulator.

25. The nonreciprocal optical device of claim 22, wherein the device is an optical switch.

26. The nonreciprocal optical device of claim 22, further comprising a circularly polarized pump light.

27. The nonreciprocal optical device of claim 26, further comprising a dichroic mirror configured to collinearly combine the signal light with the circularly polarized pump light.

28. The nonreciprocal optical device of claim 26, further comprising a dichroic mirror configured to separate the signal light with the circularly polarized pump light.

29. The nonreciprocal optical device of claim 26, further comprising a first dichroic mirror and a second dichroic mirror, wherein the first dichroic mirror is configured to collinearly combine the circularly polarized pump light with the signal light and the second dichroic mirror is configured to separate the circularly polarized pump light with the signal light.

30. A method of preventing the backflow of a light, comprising:
introducing a circularly polarized light to an optically active medium of claim 1.

31. The method of claim 30, wherein the circularly polarized light is a signal light.

32. The method of claim 30, further comprising collinearly combining the circularly polarized light with a signal light before introducing the combined light to the optically active media.

33. The method of claim 32, wherein a dichroic mirror is configured to combine the circularly polarized light with the signal light.

34. The method of claim 30, further comprising separating the circularly polarized light with a signal light after introducing a combined light to the optically active media.

35. The method of claim 34, wherein a dichroic mirror is configured to separate the circularly polarized light with the signal light.

36. The method of claim 30, further comprising:
combining the circularly polarized light with a signal light before introducing the combined light to the optically active media; and
separating the circularly polarized light with a signal light after introducing the combined light to the optically active media.

37. The method of claim 36, wherein a first dichroic mirror is configured to combine the circularly polarized light with the signal light and a second dichroic mirror is configured to separate the circularly polarized light from the signal light.

\* \* \* \* \*

UNITED STATES PATENT AND TRADEMARK OFFICE
CERTIFICATE OF CORRECTION

| | | |
|---|---|---|
| PATENT NO. | : 12,292,668 B2 | Page 1 of 1 |
| APPLICATION NO. | : 17/443285 | |
| DATED | : May 6, 2025 | |
| INVENTOR(S) | : Bernard Yurke | |

It is certified that error appears in the above-identified patent and that said Letters Patent is hereby corrected as shown below:

In the Claims

In Claim 14, Column 48, Lines 39-40:
DELETE: "-like stacking"

In Claim 27, Column 49, Line 2:
DELETE: "collinearly"
INSERT: --colinearly--

In Claim 29, Column 49, Line 10:
DELETE: "collinearly"
INSERT: --colinearly--

In Claim 32, Column 49, Lines 20-21:
DELETE: "collinearly"
INSERT: --colinearly--

Signed and Sealed this
Tenth Day of June, 2025

Coke Morgan Stewart
*Acting Director of the United States Patent and Trademark Office*